(12) United States Patent
Haddach

(10) Patent No.: US 11,912,706 B2
(45) Date of Patent: Feb. 27, 2024

(54) CRYSTAL FORMS OF A POL1 INHIBITOR

(71) Applicant: PIMERA, INC., San Diego, CA (US)

(72) Inventor: Mustapha Haddach, San Diego, CA (US)

(73) Assignee: PIMERA, INC., San Diego, CA (US)

( * ) Notice: Subject to any disclaimer, the term of this patent is extended or adjusted under 35 U.S.C. 154(b) by 886 days.

(21) Appl. No.: 16/497,724

(22) PCT Filed: Mar. 28, 2018

(86) PCT No.: PCT/US2018/024898
§ 371 (c)(1),
(2) Date: Sep. 25, 2019

(87) PCT Pub. No.: WO2018/183540
PCT Pub. Date: Oct. 4, 2018

(65) Prior Publication Data
US 2023/0192694 A1    Jun. 22, 2023

Related U.S. Application Data

(60) Provisional application No. 62/491,635, filed on Apr. 28, 2017, provisional application No. 62/477,746, filed on Mar. 28, 2017.

(51) Int. Cl.
*C07D 471/14* (2006.01)

(52) U.S. Cl.
CPC ........ *C07D 471/14* (2013.01); *C07B 2200/13* (2013.01)

(58) Field of Classification Search
CPC .......................... C07D 471/14; C07D 2200/13
See application file for complete search history.

(56) References Cited

U.S. PATENT DOCUMENTS

| | | |
|---|---|---|
| 1,042,801 A | 10/1912 | Kitsee |
| 4,650,737 A | 3/1987 | Wiedemann et al. |
| 5,624,677 A | 4/1997 | El-Rashidy et al. |
| 7,141,565 B1 | 11/2006 | Whitten et al. |
| 7,326,702 B2 | 2/2008 | Whitten et al. |
| 7,354,916 B2 | 4/2008 | Whitten et al. |
| 7,381,720 B2 | 6/2008 | Whitten et al. |
| 7,402,579 B2 | 7/2008 | Whitten et al. |
| 7,507,727 B2 | 3/2009 | Whitten et al. |
| 7,612,063 B2 | 11/2009 | Whitten et al. |
| 7,652,134 B2 | 1/2010 | Whitten et al. |
| 7,816,406 B2 | 10/2010 | Whitten et al. |
| 7,816,524 B2 | 10/2010 | Chua et al. |
| 7,928,100 B2 | 4/2011 | Nagasawa et al. |
| 7,998,978 B2 | 8/2011 | Huang et al. |
| 8,142,909 B2 | 3/2012 | Beers et al. |
| 8,518,952 B2 | 8/2013 | Braganza et al. |
| 8,637,529 B2 | 1/2014 | Woller et al. |
| 9,512,123 B2 | 12/2016 | Haddach |
| 9,688,697 B2 | 6/2017 | Achiron et al. |
| 9,758,518 B2 * | 9/2017 | Haddach ............ A61K 31/4353 |
| 9,951,066 B2 | 4/2018 | Haddach |
| 10,745,403 B2 | 8/2020 | Haddach |
| 2011/0218184 A1 | 9/2011 | Nagasawa et al. |
| 2012/0007069 A1 | 1/2012 | Lee et al. |
| 2015/0284410 A1 | 10/2015 | Achiron et al. |
| 2016/0257678 A1 | 9/2016 | Haddach et al. |
| 2017/0143737 A1 | 5/2017 | Soong et al. |
| 2018/0079750 A1 | 3/2018 | Haddach |
| 2019/0233422 A1 | 8/2019 | Haddach |
| 2020/0361937 A1 | 11/2020 | Haddach |
| 2021/0094952 A1 | 4/2021 | Haddach |
| 2021/0317120 A1 | 10/2021 | Haddach |

FOREIGN PATENT DOCUMENTS

| | | |
|---|---|---|
| CN | 101781312 A | 7/2010 |
| CN | 101888780 A | 11/2010 |
| CN | 106349244 A | 1/2017 |
| DE | 2929414 A1 | 2/1981 |
| EP | 1325009 B1 | 3/2006 |
| EP | 2414355 A2 | 2/2012 |
| JP | S5333227 A | 3/1978 |
| JP | S61175647 A | 8/1986 |
| JP | H08245540 A | 9/1996 |
| KR | 20120061056 A | 6/2012 |
| KR | 20130090726 A | 8/2013 |
| WO | WO-0228860 A2 | 4/2002 |
| WO | WO-2007038215 A1 | 4/2007 |
| WO | WO-2008060693 A2 | 5/2008 |
| WO | WO-2009046383 A1 | 4/2009 |
| WO | WO-2010135751 A2 | 11/2010 |
| WO | WO-2013059559 A2 | 4/2013 |
| WO | WO-2015172123 A1 | 11/2015 |

(Continued)

OTHER PUBLICATIONS

Akira Ogata. Chemical Experimental Procedures, Nankodo Co., Ltd., pp. 366 to 399 (1963).
Hirayama Yoshinaki. Handbook of organic compound crystal—Principle and know-how, Marzen Co., Ltd., p. 57-84 (Jan. 25, 2008).
Takata. API form Screening and selection in the stage of drug development. Pharm Stage 6(10):20-25 (2007).
U.S. Appl. No. 16/739,354 Office Action dated Apr. 8, 2021.
U.S. Appl. No. 16/925,220 Office Action dated Sep. 27, 2021.
Jaworska et al. SAR applicability domain. Review of methods for assessing the applicability domains of SARS and QSARS. Paper 4: SAR applicability domain. 9 pages, 2004.
U.S. Appl. No. 16/925,220 Office Action dated May 13, 2022.

(Continued)

*Primary Examiner* — Michael Barker
*Assistant Examiner* — Jed A Kucharczk
(74) *Attorney, Agent, or Firm* — Wilson Sonsini Goodrich & Rosati

(57) ABSTRACT

The present invention relates to novel solid crystalline form of N-methyl-2-(4-methyl-1,4-diazepan-1-yl)benzo [4,5]imidazo[1,2-a][1,8]naphthyridine-6-carbaxomide, processes for the preparation thereof, compositions thereof and method of use thereof.

8 Claims, 67 Drawing Sheets

(56) References Cited

FOREIGN PATENT DOCUMENTS

| WO | WO-2016141042 A2 | 9/2016 |
|---|---|---|
| WO | WO-2018183540 A1 | 10/2018 |

OTHER PUBLICATIONS

Achiron et al. RAM-589.555 a new Polymerase-1 inhibitor as innovative targeted-treatment for multiple sclerosis. Journal of Neuroimmunology 302:41-48 (2017).

Babichev et al. Unexpected O →N-migration of methyl group in 5-methoxy-6-cyanobenzimidazo[1,2-a][1,8]naphthyridine. Chem Heterocycl Compd 25:230 (1989).

Balduzzi et al. Trastuzumab-containing regimens for metastatic breast cancer (Review). Cochrane Database of Systematic Reviews pp. 1-4 (2014).

Hranjec et al. Novel Cyano- and Amidino-Substituted Derivatives of Styryl-2-Benzimidazoles and Benzimidazo[1,2-a]quinolines. Synthesis, Photochemical Synthesis, DNA Binding, and Antitumor Evaluation, Part 3. J Med Chem 50(23):5696-711 (2007).

Huang et al. An efficient one-pot synthesis of benzo[4,5]imidazo[1,2-a]quinoxalines via copper-catalyzed process. Org Lett. 15(21):5480-3 (2013).

Kato et al. Novel Strategy for Synthesis of Substituted Benzimidazo[1,2-a]quinolines. Organic Letters 15:3794-3797 (2013).

Shvedov et al. Synthesis of derivatives of pyrazino[1,2-a]benzimidazole, aza analogs ofβ-carboline. Pharmaceutical Chemistry Journal 3(10):566-570 (1969) (Translated from Khimiko-Farmatsevticheskii Zhurnal 10, pp. 15-20 Oct. 1969) (English translation).

Agrawal et al. Synthesis, Analytical Analysis and Medicinal Aspect of Novel Benzimidazoles and their Megal Complexes. Chem Biol Drug Des 82:630-634 (2013).

Andaloussi et al., Novel imidazo[1,2-a]naphthyridinic systems (part 1): synthesis, antiproliferative and DNA-intercalating activities. European Journal of Medicinal Chemistry 43(11):2505-2517 (2008).

Augustine et al. gem-Dibromomethylarenes: a convenient substitute for noncommercial aldehydes in the knoevenagel-doebner reaction for the synthesis of alpha,beta-unsaturated carboxylic acids. J Org Chem 72:9854-9856 (2007).

Beaulieu et al., Synthesis and biological evaluation of 4-amino derivatives of benzimidazoquinoxaline, benzimidazoquinoline, and benzopyrazoloquinazoline as potent IKK inhibitors. Bioorg Med Chem Lett. 17(5):1233-1237 (2007).

Berge et al. Pharmaceutical Salts. Journal of Pharmaceutical Sciences 66(1):1-19 (Jan. 1977).

Bundgaard. Chapter 5: Design and Application of Prodrugs. A Textbook of Drug Design and Development. (pp. 113-191) (1991).

Bundgaard. Means to Enhance Penetration: Prodrugs as a Means to Improve the Delivery of Peptide Drugs. Advanced Drug Delivery Review 8:1-38 (1992).

Cai et al. Synthesis of Aza-Fused Polycyclic Quinolines through Copper-Catalyzed Cascade Reactions. Organic Letters 12(7):1500-1503 (2010).

Chemical Abstract Compounds, STN Registry entry for RN 183858-23-3 (1996).

Chemical Abstract Compounds, STN Registry entry for RN 183858-24-4 (1996).

Chemical Abstract Compounds, STN Registry entry for RN 93438-49-4 (1984).

Chen et al. Overexpression of 5-lipoxygenase in rat and human esophageal adenocarcinoma and inhibitory effects of zileuton and celecoxib on carcinogenesis. Clin Cancer Res. 10(19):6703-9 (2004).

Cortes et al. Effect of Low Doses of Actinomycin D on Neuroblastoma Cell Lines. Molecular Cancer 15:1 (2016).

Ding et al. A novel anti-pancreatic cancer agent, LY293111. Anticancer Drugs 16(5):467-473 (2005).

Drygin et al. Anticancer activity of CX-3543: a direct inhibitor of rRNA biogenesis. Cancer Res 69:7653-7661 (2009).

Drygin et al. RNA Polymerase I Transcription. Encyclopedia of Cancer pp. 1-5 (2014).

Ebitani et al. Reconstructed hydrotalcite as a highly active heterogeneous base catalyst for carbon-carbon bond formations in the presence of water. J Org Chem 71:5440-5447 (2006).

Hranjec et al. Benzimidazole Derivatives related to 2,3-acrylonitriles, benzimidazo [1,2-a] Quinolines and Fluorenes: Synthesis, Antitumor Evaluation in vitro and crystal structure determination. European Journal of Medicinal Chemistry 45:2405-2417 (2010).

Hranjec et al. Synthesis of novel benzimidazolyl-substituted acrylonitriles and amidino-substituted benzimidazo[1,2-a]quinolines. Molecules 12:1817-1828 (2007).

Hudis. Trastuzumab—Mechanism of Action and Use in Clinical Practice. The New England Journal of Medicine 357(1):39-51 ((Jul. 5, 2007).

Kim et al. Genetic Requirement for Mycl and Efficacy of Rna Pol I inhibition in Mouse Models of Small Cell Lung Cancer. Genes Develop 30:1289-1299 (2016).

Leung et al. Copper-CX-5461: A novel liposomal formulation for small molecule rRNA synthesis inhibitor. Journal of Controlled Release 286:1-9 (2018).

Lu et al. Organocatalytic Decarboxylative Doebner-Knoevenagel Reactions between Arylaldehydes and Monoethyl Malonate Mediated by a Bifunctional Polymeric Catalyst. Synlett 2011(12):1723-1726 (2011).

Mase et al. Organocatalytic Knoevenagel condensations by means of carbamic acid ammonium salts. Org Lett 15:1854-1857 (2013).

Mogilaiah et al. Synthesis of Some Novel Bridgehead Nitrogen Heterocyclic Systems Containing 1,8-Naphthyridine Moiety. Indian Journal of Chemistry 42B:192-194 (2003).

Mohite et al. A practical and convenient protocol for the synthesis of (E)-α,β-unsaturated acids. Org Lett 15:4564-4567 (2013).

PCT/US2015/030046 International Search Report and Written Opinion dated Sep. 10, 2015.

PCT/US2016/020418 International Search Report and Written Opinion dated Aug. 30, 2016.

PCT/US2018/024898 International Search Report and Written Opinion dated Aug. 9, 2018.

Perin et al. Novel biologically active nitro and amino substituted benzimidazo[1,2-a]quinolines. Bioorg Med Chem. 19(21):6329-39 (2011).

Perin et al. Synthesis, Antiproliferative Activity and DNA Binding Properties of Novel 5-Aminobenzimidazo [1,2-a] quinoline-6-carbonitriles. European Journal of Medicinal Chemistry 80:218-227 (2014).

Perin et al., Biological Activity and DNA Binding Studies of 2-Substituted Benzimidazo [1,2-a]quinolines bearing different amino side chains. Medicinal Chemistry Communication 4:1537 (2013).

Ranu et al. Ionic Liquid as Catalyst and Reaction Medium—A Simple, Efficient and Green Procedure for Knoevenagel Condensation of Aliphatic and Aromatic Carbonyl Compounds Using a Task-Specific Basic Ionic Liquid. Eur J Org Chem 2006(16):3767-3770 (2006).

Rebello et al. The Dual Inhibition of RNA Pol I Transcription and PIM Kinase as a New Therapeutic Approach to Treat Advanced Prostate Cancer. American Association for Cancer Research 22:5539-5552 (2016).

Schwaebe et al. Facile and Efficient Generation of Quinolone Amides from Esters Using Aluminum Chloride. Tetrahedron Letters 52:1096-1100 (2011).

Shvedov et al., Synthesis of derivatives of pyrazino[1,2-a]benzimidazole, aza analogs of β-carboline. Pharmaceutical Chemistry Journal 3(10:)566-570 (1969).

Su et al. Organic Reactions in Ionic Liquids: Knoevenagel Condensation Catalyzed by Ethylenediammonium Diacetate. Synthesis 2003(4):0555-0559 (2003).

U.S. Appl. No. 14/708,230 Office Action dated Feb. 25, 2016.

U.S. Appl. No. 14/935,155 Office Action dated Jan. 27, 2017.

U.S. Appl. No. 15/485,106 Office Action dated Oct. 31, 2017.

U.S. Appl. No. 15/661,770 Office Action dated Jun. 12, 2018.

U.S. Appl. No. 15/864,965 Office Action dated May 31, 2018.

U.S. Appl. No. 16/430,129 Office Action dated Nov. 5, 2019.

(56) References Cited

OTHER PUBLICATIONS

Widder et al. Section III: Prodrugs Kinetics. Method in Enzymology. 112:309-396 (1985).

Wolfgang-R. Knappe, Photochemie des 10-phenylisoalloxazins: intramolekulare singulett- und intermolekulare triplett-reaktionen. Chemische Berichte 107:1614-1636 (1974).

Yadav et al. Phosphane-Catalyzed Knoevenagel Condensation: A Facile Synthesis of α-Cyanoacrylates and α-Cyanoacrylonitriles. Eur J Org Chem 2004(3):546-551 (2004).

Zanzoul et al., A benzimidazopyridoquinoxaline as promising scaffold for G-quadruplex DNA targeting. Medicinal Chemistry Research Sep. 2014, vol. 23:4042-4049 (2014).

* cited by examiner

CRYSTAL FORMS OF A POL1 INHIBITOR

CROSS-REFERENCE TO RELATED APPLICATIONS

This application is the National Stage of International Application No. PCT/US2018/024898, filed Mar. 28, 2018, which claims priority to U.S. Provisional Patent Application No. 62/477,746, filed Mar. 28, 2017; and U.S. Provisional Patent Application No. 62/491,635, filed Apr. 28, 2017, each of which are hereby incorporated by reference in their entirety.

FIELD OF THE INVENTION

The present invention relates in part to novel crystalline forms of N-methyl-2-(4-methyl-1,4-diazepan-1-yl)benzo[4,5]imidazo[1,2-a][1,8]naphthyridine-6-carbaxomide having certain biological activities that include, but are not limited to, inhibiting cell proliferation and/or inducing cell apoptosis. The invention also relates in part to methods for using such forms, processes for their preparation, and compositions thereof.

BRIEF SUMMARY OF THE INVENTION

In one aspect is provided a solid form of Compound (I):

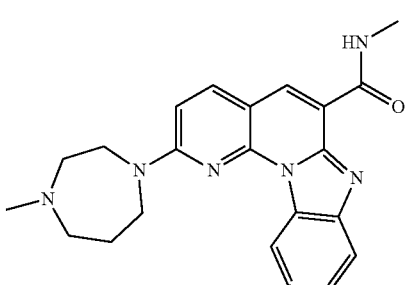

(I)

N-methyl-2-(4-methyl-1,4-diazepan-1-yl)benzo[4,5]imidazo[1,2-a][1,8]naphthyridine-6-carboxamide In one variation, the solid form is a crystalline form. In one variation, the crystalline form is specifically described herein (e.g., Forms 1-5).

The specific crystal forms described herein can be advantageous over the known solid form of Compound (I) by virtue of improved handling characteristics, lower tendency to aggregate, improved suitability for forming cohesive solid forms (tablets), improved stability for long term storage, better solubility, and/or improved solubility profiles.

Crystalline Forms

Form 1

In one variation, the crystalline form of Compound (I) is a crystalline form of Form 1. In particular embodiments, the crystalline Form 1 is advantageous because it can be prepared consistently, while other crystal forms can convert to the crystalline Form 1 upon storage or handling. Indeed, some of the other forms can be converted into the crystalline Form 1 readily. Conditions for such interconversion are described herein. Consistent physical properties greatly facilitate handling, and preparation of solid dosage forms on production scale; thus it is advantageous to use a crystalline form that is stable under normal handling conditions. Thus in one embodiment, the crystalline Form 1 is utilized.

In some embodiments, the crystalline Form 1 is characterized by having a powder X-ray diffraction pattern comprising peaks of 2-theta at about 10.0° and 20.7°.

In some embodiments, the crystalline Form 1 is characterized as having any one or combination of powder X-ray diffraction pattern peaks of 2-theta at about 6.7°, 8.6°, 10.0°, 11.2°, 16.2°, 20.7°, 22.7°, 25.6° and 27.6°(±0.2° 2θ). In some embodiments, the crystalline Form 1 is characterized by having a powder X-ray diffraction pattern substantially as shown in FIG. 81.

In some embodiments, the crystalline Form 1 is characterized by having an endothermic peak at about 212-216° C. as shown by differential scanning calorimetry. In some embodiments, the crystalline Form 1 is characterized by having a differential scanning calorimetry substantially as shown in FIG. 22.

In some embodiments, the crystalline Form 1 is characterized by having a thermogravimetric analysis substantially as shown in FIG. 21.

Form 2

In one variation, the crystalline form of Compound (I) is a crystalline form of Form 2. In some embodiments, the crystalline Form 2 is characterized by having a powder X-ray diffraction pattern comprising peaks of 2-theta at about 20.3° and 26.4°.

In some embodiments, the crystalline Form 2 is characterized by having a powder X-ray diffraction pattern comprising peaks of 2-theta at about 6.7°, 11.2°, 17.5°, 19.5°, 20.3°, 21.7° and 26.4°(±0.2° 2θ). In some embodiments, the crystalline Form 2 is characterized by having a powder X-ray diffraction pattern substantially as shown in FIG. 82.

In some embodiments, the crystalline Form 2 is characterized by having a differential scanning calorimetry substantially as shown in FIG. 29.

In some embodiments, the crystalline Form 2 is characterized by having a thermogravimetric analysis substantially as shown in FIG. 28.

Form 3

In one variation, the crystalline form of Compound (I) is a crystalline form of Form 3. In some embodiments, the crystalline Form 3 is characterized by having a powder X-ray diffraction pattern comprising peaks of 2-theta at about 6.4° and 13.5°.

In some embodiments, the crystalline Form 3 is characterized by having a powder X-ray diffraction pattern comprising peaks of 2-theta at about 6.4°, 9.3°, 9.7°, 13.5°, 19.1°, 23.7° and 28.0° (±0.2° 2θ). In some embodiments, the crystalline Form 3 is characterized by having a powder X-ray diffraction pattern substantially as shown in FIG. 83.

In some embodiments, the crystalline Form 3 is characterized by having a differential scanning calorimetry substantially as shown in FIG. 37.

In some embodiments, the crystalline Form 3 is characterized by having a thermogravimetric analysis substantially as shown in FIG. 36.

Form 4

In one variation, the crystalline form of Compound (I) is a crystalline form of Form 4. In some embodiments, the crystalline Form 4 is characterized by having a powder X-ray diffraction pattern comprising peaks of 2-theta at about 7.0° and 11.4°.

In some embodiments, the crystalline Form 4 is characterized by having a powder X ray diffraction pattern comprising peaks of 2-theta at about 6.3°, 7.0°, 9.3°, 9.7°, 11.4°, 19.1°, 25.6° and 27.9° (±0.2° 2θ). In some embodiments, the crystalline Form 4 is characterized by having a powder X ray diffraction pattern substantially as shown in FIG. 84.

In some embodiments, the crystalline Form 4 is characterized by having a differential scanning calorimetry substantially as shown in FIG. 43.

In some embodiments, the crystalline Form 4 is characterized by having a thermogravimetric analysis substantially as shown in FIG. 42.

Form 5

In one variation, the crystalline form of Compound (I) is the crystalline Form 5. In some embodiments, the crystalline Form 5 is characterized by having a powder X-ray diffraction pattern comprising peaks of 2-theta at about 9.2° and 10.3°.

In some embodiments, the crystalline Form 5 is characterized by having a powder X-ray diffraction pattern comprising peaks of 2-theta at about 9.2°, 10.3°, 11.2°, 18.1°, 19.7°, 21.2°, 23.6° and 25.8° (±0.2° 2θ). In some embodiments, the crystalline Form 5 is characterized by having a powder X-ray diffraction pattern substantially as shown in FIG. 85.

In some embodiments, the crystalline Form 5 is characterized by an endothermic peak at about 212-213.5° C. as shown by differential scanning calorimetry. In some embodiments, the crystalline Form 5 is characterized by having a differential scanning calorimetry substantially as shown in FIG. 49.

In some embodiments, the crystalline Form 5 is characterized by having a thermogravimetric analysis substantially as shown in FIG. 48.

Methods of Manufacture

In one aspect is provided a process for producing a crystalline form of Compound (I). In one variation, the crystalline form of Compound (I) is any crystalline form described herein (e.g. the crystalline Forms 1, 2, 3, 4, and 5). In specific aspects, the crystalline form of Compound (I) is the crystalline Form 1 or the crystalline Form 5.

Form 1

In one variation is provided a process for producing the crystalline Form 1 comprising preparing a mixture (e.g., slurry) of multiphase Compound (I) in acetone. In some embodiments, the mixture is temperature cycled (e.g., from about 5° C. to 25° C. for a period of about 72 hours).

Form 2

In one variation is provided a process for producing the crystalline Form 2 comprising preparing a mixture (e.g., slurry) of Compound (I) in 1,4-dioxane. In some embodiments, the mixture is temperature cycled (e.g., from about 5° C. to 25° C. for a period of about 72 hours).

Form 3

In one variation is provided a process for producing the crystalline Form 3 comprising preparing a mixture (e.g., slurry) of Compound (I) in dichloromethane. In some embodiments, the mixture is temperature cycled (e.g., from about 5° C. to 25° C. for a period of about 72 hours).

Form 4

In one variation is provided a process for producing the crystalline Form 4 comprising dissolving Compound (I) in dichloromethane. In some embodiments, the resulting suspension is filtered and allowed to go evaporative crystallization at ambient conditions in an uncapped vial.

Form 5

In one variation is provided a process for producing the crystalline Form 5 comprising dissolving Compound (I) in dichloromethane. In some embodiments, heptane is added to the resulting suspension to precipitate material back out of the solution.

Compositions

In one aspect is provided a composition comprising a crystalline form of Compound (I) described herein. In one variation is provided a crystalline form described herein (e.g., crystalline Form 1, 2, 3, 4, and 5), and a pharmaceutically acceptable carrier. In some embodiments, the composition comprises an effective amount of the crystalline form and a pharmaceutically acceptable carrier.

Methods of Treatment

In one aspect is provided a method for inhibiting cell proliferation comprises contacting cells with an effective amount of a form of Compound (I), wherein the form is derived from a crystalline form (e.g., the crystalline Forms 1, 2, 3, 4, and 5) of Compound (I). In some embodiments, the cells are a cancer cell line. In some embodiments, the cancer cell line is a breast cancer, prostate cancer, pancreatic cancer, lung cancer, hemopoietic cancer, colorectal cancer, skin cancer, ovary cancer cell line. In some embodiments, the cells are in a tumor in a subject. In some embodiments, contacting cells induces cell apoptosis.

In one aspect is provided a method for treating a condition related to aberrant cell proliferation, the method comprising administering to an individual in need thereof an effective amount of a crystalline form described herein (e.g., the crystalline Forms 1, 2, 3, 4, and 5). In some embodiments, the cell proliferative condition is a tumor-associated cancer. In some embodiments, the cancer is of the breast, prostate, pancreas, lung, colorectal, skin, or ovary. In some embodiments, the cell proliferative condition is a non-tumor cancer. In some embodiments, the non-tumor cancer is a hematopoietic cancer.

In one aspect is provided a method of inhibiting angiogenesis in an individual in need thereof, comprising administering to the individual an effective amount of a crystalline form described herein (e.g., the crystalline Forms 1, 2, 3, 4, and 5).

In one aspect is provided a method of treating cancer or an inflammatory disorder in individual in need thereof, comprising administering to the individual an effective amount of a crystalline form described herein (e.g., the crystalline Forms 1, 2, 3, 4, and 5); and administering an additional pharmaceutical agent, additional treatment modality, or combination thereof.

In some embodiments, the crystalline form and the additional pharmaceutical agent are combined into one pharmaceutical composition. In some embodiments, administering the additional pharmaceutical agent, additional treatment modality, or combination thereof is performed concurrently with administering the crystalline form. In some embodiments, administering the additional pharmaceutical agent, additional treatment modality, or combination thereof is performed after administering the crystalline form. In some embodiments, administering the additional pharmaceutical agent, additional treatment modality, or combination thereof is performed prior to administering the crystalline form.

Kits

In one aspect is provided a kit for the treatment or prevention in an individual with cancer, comprising a crystalline form of Compound (I) described herein (e.g., the crystalline Forms 1, 2, 3, 4, and 5) and packaging.

In one variation is provided a kit for the treatment or prevention in an individual with cancer, comprising a composition of the crystalline forms described herein and packaging.

BRIEF DESCRIPTION OF THE FIGURES

Further objectives and advantages will become apparent from a consideration of the description, drawings, and examples.

DETAILED DESCRIPTION OF THE INVENTION

Figure 1:
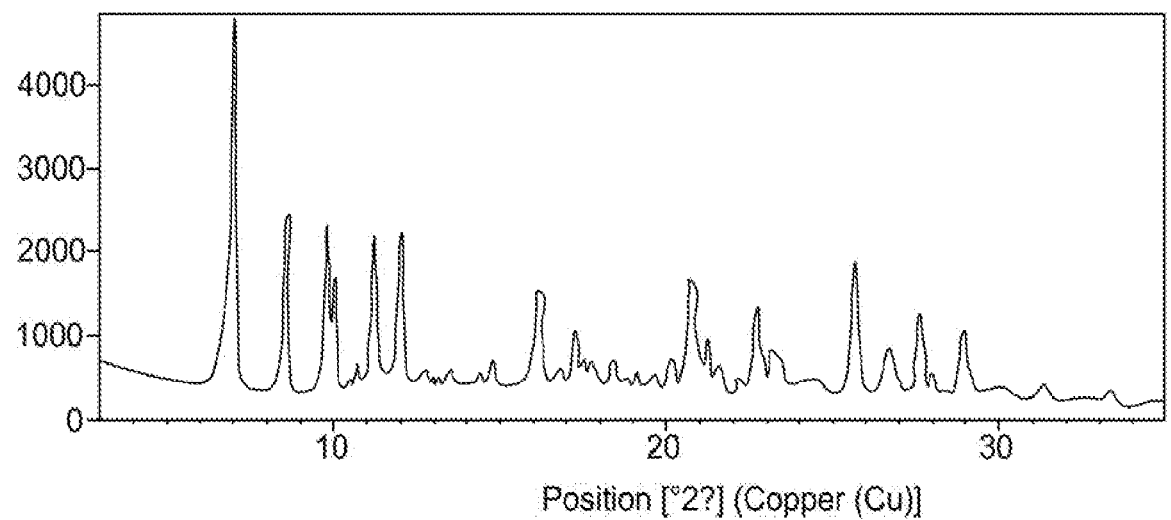
FIG. 1 depicts the powder X-ray diffraction pattern (PXRD) of N-methyl-2-(4-methyl-1,4-diazepan-1-yl)benzo[4,5]imidazo[1,2-a][1,8]naphthyridine-6-carbaxomide (Compound (I)) in multiphasic form.

Other objects, features and advantages of the Compounds, methods and compositions described herein will become apparent from the following detailed description. It should be understood however, that the detailed description and the specific examples, while indicating specific embodiments, are given by way of illustration only, since various changes and modifications within the spirit and scope of the instant disclosure will become apparent to those skilled in the art from this detailed description.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Described herein are crystalline forms of Compound (I):

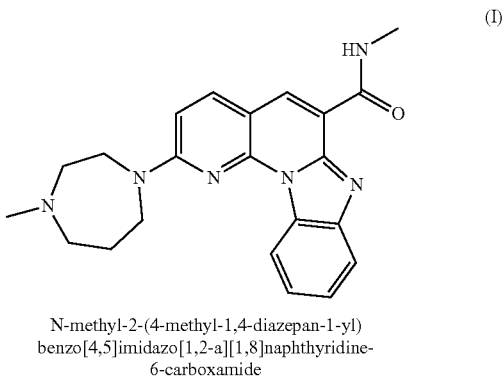

N-methyl-2-(4-methyl-1,4-diazepan-1-yl)
benzo[4,5]imidazo[1,2-a][1,8]naphthyridine-
6-carboxamide (I)

Compound (I) has certain biological activities that include, but are not limited to inhibiting cell proliferation and/or inducing cell apoptosis. Compound (I) and pharmaceutically acceptable salts, prodrugs, active metabolites, co-crystal and pharmaceutically acceptable solvates thereof can inhibit ribosome biogenesis by inhibiting POL1 transcription.

Also provided are methods for preparing novel crystalline forms of Compound (I) and methods of using thereof. Also provided are compositions comprising the above-described forms of Compound (I) in combination with other agents (e.g., one or more additional pharmaceutical agents), and methods for using such in combination with other agents.

As is well known to the skilled artisan, variations in the salt form and/or crystal structure of a pharmaceutical drug substance often affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product, particularly when formulated in a solid oral dosage form.

Experimentation with a plethora of crystallization conditions (e.g., various solvents, solvent mixtures, varying cooling rates, etc.) revealed that the production of particular crystalline forms described herein was unpredictable, thus, specific processes for consistently producing these crystalline forms were developed. These methods allowed the preparation and characterization of the novel crystalline forms disclosed herein. The processes for the preparation of and characterization of these forms are described in greater detail below. These crystalline forms of Compound (I) may have particularly desirable characteristics in the solid form, such as dissolution rate, absorption and stability.

For example, certain crystalline forms exhibit higher intrinsic solubility and/or faster dissolution rates than others, which may be advantageous for handling and formulation purposes.

In another aspect is provided crystalline forms of Compound (I), namely, the crystalline Forms 1, 2, 3, 4, and 5. Each of these is a crystalline version of Compound (I). These crystal forms of Compound (I) are useful for the preparation of solid dosage forms of a pharmaceutical composition that exhibits the biological activities of Compound (I), including efficacy for treating proliferative disorders discussed herein. The novel crystalline forms may be more stable than the multiphasic or amorphous forms of Compound (I).

In another aspect, the invention provides a method to make specific crystal forms of the salts of Compound (I), as further described herein.

In another aspect are provided methods of treating a condition that is responsive to Compound (I) using a crystalline form described herein (e.g., the crystalline Form 1, 2, 3, 4, and 5). Such conditions include pain, inflammation, angiogenesis, and cell proliferation (e.g., cancer).

In one aspect, described herein is a method for treating or preventing cancer in a mammal comprising administering a therapeutically effective amount of a crystalline form of Compound (I) described herein, or a pharmaceutically acceptable salt, co-crystal, or solvate thereof, to the mammal in need thereof. In another aspect, described herein is a method for treating or preventing an inflammatory disease in a mammal comprising administering a therapeutically effective amount of a crystalline form of Compound (I) described herein, or a pharmaceutically acceptable salt, co-crystal or solvate thereof, to the mammal in need thereof.

In still another aspect, described herein is a method for treating or preventing a proliferative disorder in a mammal comprising administering a therapeutically effective amount of a crystalline form of Compound (I) described herein, or a pharmaceutically acceptable salt, co-crystal, or solvate thereof, to the mammal in need thereof. In another aspect, described herein is a method for treating or preventing a disease or disorder in a mammal comprising administering a therapeutically effective amount of a crystalline form of Compound (I) described herein.

In some embodiments, the methods, crystalline forms of Compound (I) and compositions described herein can be used as a mixture of two or more of these crystal forms; mixtures of crystal forms are sometimes useful. In some embodiments, the methods and compositions described herein can be used as a mixture of one or more of these crystal forms with an additional pharmaceutical agent, as described herein.

Also provided are kits, compositions, combination therapies and unit dosage forms of the crystal forms described herein.

Abbreviations and Definitions

Nomenclature of some compounds described herein may be identified using ChemDraw Ultra Version 10.0, available from CambridgeSoft®.

As used herein, "amorphous" refers to a material that contains too little crystal content to yield a discernable pattern by PXRD or other diffraction techniques. Glassy materials are contemplated to be amorphous. Amorphous materials do not have a true crystal lattice, and are consequently glassy rather than true solids, technically resembling very viscous non-crystalline liquids. Rather than true solids, glasses may better be described as quasi-solid amorphous material. Thus an amorphous material refers to a quasi-solid glassy material. Precipitation of a compound from solution, often affected by rapid evaporation of solvent, may favor amorphous forms of a compound.

As used herein, "crystalline" refers to a material that contains a specific compound, which may be hydrated and/or solvated, or in the form of a co-crystal and has sufficient crystal content to exhibit a discernable diffraction pattern by powder X-ray diffraction (PXRD) or other diffraction techniques. Crystalline material may be characterized by a number of additional analytical techniques, including infrared spectra (e.g., Fourier Transform-IR (FTIR), differential scanning calorimetry (DSC), density, crystal group, and solubility. A crystalline material that is obtained from a solvent by direct crystallization of a compound dissolved in a solution or interconversion of crystals obtained under different crystallization conditions, may have crystals that contain the solvent. The specific solvent composition and physical properties of crystallization (e.g., rate of crystallization, temperature) collectively termed crystallization conditions, may cause one crystal form to dominate and may result in crystalline material having physical and chemical properties that are unique to the crystallization conditions.

The salt forms of the invention can be formed from the parent compound, i.e., Compound (I), due to the ionizable groups of the parent compound. These salts may be acid addition salts involving inorganic or organic acids or the salts may, in the case of acidic forms of the parent compound of the invention be prepared from inorganic or organic bases. Frequently, the salts are prepared or used as pharmaceutically acceptable salts prepared as addition products of pharmaceutically acceptable acids or bases. Suitable pharmaceutically acceptable acids and bases are well-known in the art, such as hydrochloric, sulfuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.; P. Heinrich Stahl, Camille G. Wermuth, Pharmaceutical Salts: Properties, Selection, and Use, Edition 2.

Furthermore, the present salt forms may be anhydrous or contain solvent(s), such as water. In some embodiments, the present salt forms comprise solvate, such as hydrate.

"Solvate", as used herein, means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate". Examples of hydrates include, but are not limited to, hemihydrate, monohydrate, dihydrate, trihydrate, hexahydrate, etc. It should be understood by one of ordinary skill in the art that the pharmaceutically acceptable salt, and/or prodrug of the present salt form may also exist to include a solvate. The solvate is typically formed via hydration which is either part of the preparation of the present salt form or through natural absorption of moisture by the anhydrous salt form of the present invention.

The terms "administer," "administering", "administration," and the like, as used herein, refer to the methods that may be used to enable delivery of a compound/composition to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed. In some embodiments, the Compounds and compositions described herein are administered orally.

As used herein, "co-crystal" refers to solids that are crystalline single phase materials composed of two or more different molecular and/or ionic compounds generally in a stoichiometric ratio which are neither solvates nor simple salts. As used herein, the term co-crystal can encompass hydrates, solvates and clathrates.

As used herein, "treatment", "treating", or "treat" is an approach for obtaining beneficial or desired results, including clinical results. For purposes herein, beneficial or desired results include, but are not limited to, one or more of the following: decreasing one more symptoms resulting from the condition (e.g., cancer), diminishing the extent of the disease, stabilizing the condition (e.g., preventing or delaying the worsening of the condition, such as cancer), delay or slowing the progression of the condition, ameliorating the disease state, decreasing the dose of one or more other medications required to treat the condition, increasing the quality of life of an individual who has been or is suspected of having the condition, and/or prolonging survival (including overall survival and progression free survival). Also encompassed by "treatment" is a reduction of pathological consequence of cancer. The methods described herein contemplate any one or more of these aspects of treatment.

As used herein, "delaying" with respect to a condition means to defer, hinder, slow, retard, stabilize, and/or postpone development of, and/or one or more symptoms of the condition (e.g., cancer). This delay can be of varying lengths of time, depending on the history of the disease and/or individual being treated. As is evident to one skilled in the art, a sufficient or significant delay can, in effect, encompass prevention, in that the individual does not develop the condition (e.g., cancer). A method that "delays" development of cancer is a method that reduces the probability of disease development in a given time frame and/or reduces the extent of the condition in a given time frame, when compared to not using the method. Such comparisons are typically based on clinical studies, using a statistically significant number of subjects. Cancer development can be detectable using standard methods, such as routine physical exams or X-ray. Development may also refer to disease progression that may be initially undetectable and includes occurrence and onset.

As used herein, an "at risk" individual with respect to a condition is an individual who is at risk of developing a condition (e.g., cancer). An individual "at risk" may or may not have a detectable condition, and may or may not have displayed symptoms associated with a detectable condition prior to the treatment methods described herein. "At risk" denotes that an individual has one or more so-called risk factors, which are measurable parameters that correlate with development of the condition. An individual having one or more of these risk factors has a higher probability of developing the condition than an individual without these risk factor(s).

As used herein, "pharmaceutically acceptable" with respect to a material refers to a material that is not biologically or otherwise unsuitable, e.g., the material may be incorporated (e.g., at the time of manufacturing or administration) into a pharmaceutical composition administered to an individual without causing any significant undesirable biological effects or interacting in a deleterious manner with any of the other components of the composition in which it is contained. As used herein, the term "pharmaceutically acceptable carrier," refers to, for example, solvents, stabilizers, pH-modifiers, tonicity modifiers, adjuvants, binders, diluents, etc., known to the skilled artisan that are suitable for administration to an individual (e.g., a human). Combinations of two or more carriers are also contemplated. The pharmaceutically acceptable carrier(s) and any additional components, as described herein, should be compatible for use in the intended route of administration (e.g., oral) for a particular dosage form. Such suitability will be easily recognized by the skilled artisan, particularly in view of the teaching provided herein. Pharmaceutically acceptable carriers or excipients have preferably met the required standards of toxicological and manufacturing testing and/or are included on the Inactive Ingredient Guide prepared by the U.S. Food and Drug administration.

With respect to treatment, an "effective amount," as used herein refers to an amount that results in a desired pharmacological and/or physiological effect for a specified condition (e.g., cancer) or one or more of its symptoms and/or to completely or partially prevent the occurrence or recurrence of the condition or symptom thereof and/or may be therapeutic in terms of a partial or complete cure for the condition and/or adverse effect attributable to the condition (e.g., cancer). In reference to conditions described herein (e.g., cancer), a pharmaceutically or therapeutically effective amount may comprise an amount sufficient to, among other things, reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; prevent growth and/or kill existing cancer cells; be cytostatic and/or cytotoxic; restore or maintain vasculostasis or prevention of the compromise or loss or vasculostasis; reduction of tumor burden; reduction of morbidity and/or mortality; and/or relieve to some extent one or more of the symptoms associated with the cancer.

The effective amount may extend progression free survival (e.g. as measured by Response Evaluation Criteria for Solid Tumors, RECIST, or CA-125 changes), result in an objective response (including a partial response or a complete response), increase overall survival time, and/or improve one or more symptoms of cancer (e.g. as assessed by FOSI). In certain embodiments, the pharmaceutically effective amount is sufficient to prevent the condition, as in being administered to an individual prophylactically. Effective amount includes the eradication or amelioration of the underlying condition being treated and/or eradication or amelioration of one or more of the symptoms associated with the underlying condition such that the individual reports an improvement in feeling or condition (e.g., decreased pain intensity and/or duration), notwithstanding that the individual may still be afflicted with the underlying disease. Effective amount also includes halting or slowing the progression of the disease (e.g., cancer), regardless of whether improvement or the disease or condition is realized.

The "effective amount" may vary depending on the composition being administered, the condition being treated/prevented (e.g., the type of cancer), the severity of the condition being treated or prevented, the age, body size, weight, and relative health of the individual, the route and form of administration, the judgment of the attending medical or veterinary practitioner (if applicable), and other factors appreciated by the skilled artisan in view of the teaching provided herein. An effective amount may be assessed, for example, by using data from one or more clinical, physiological, biochemical, histological, electrophysiological, and/or behavioral evaluations.

As is understood in the art, an "effective amount" may be administered in one or more doses, i.e., a single dose or multiple doses may be required to achieve the desired treatment endpoint. An effective amount may be considered in the context of administering one or more additional pharmaceutical agents, and a crystalline may be considered to be given in an effective amount if, in conjunction with one or more additional pharmaceutical agents, one or more desirable or beneficial result(s) may be or are achieved.

When used with respect to methods of treatment/prevention and the use of the crystal forms and compositions thereof described herein, an individual "in need thereof" may be an individual who has been diagnosed with, previously treated for, and/or suspected of having the condition to be treated (e.g., a proliferative disease such as cancer). With respect to prevention, the individual in need thereof may also be an individual who is at risk for a condition (e.g., a family history of the condition, life-style factors indicative of risk for the condition, etc.).

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children, infants, and preemies. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. In some embodiments, the individual is a non-mammal, including, but not limited to, birds, and the like. The term "individual" does not denote a particular age or sex.

With respect to the crystal forms described herein, "combination therapy" means a first therapy that includes a crystalline in conjunction with a second therapy (e.g., surgery and/or an additional pharmaceutical agent) useful for treating, stabilizing, preventing, and/or delaying the disease or condition. Administration in "conjunction with" another compound includes administration in the same or different composition(s), either sequentially, simultaneously, or continuously, through the same or different routes. In some embodiments, the combination therapy optionally includes one or more pharmaceutically acceptable carriers or excipients, non-pharmaceutically active compounds, and/or inert substances.

As used herein, the term "additional pharmaceutical agent," with respect to the crystal forms described herein refers to an active agent other than the specified crystal form, (e.g., a drug and/or a different crystalline form), which is administered to elicit a therapeutic effect. The pharmaceutical agent(s) may be directed to a therapeutic effect related to the condition that the crystalline is intended to treat or prevent (e.g., cancer) or, the pharmaceutical agent may be intended to treat or prevent a symptom of the underlying condition (e.g., tumor growth, hemorrhage, ulceration, pain, enlarged lymph nodes, cough, jaundice, swelling, weight loss, cachexia, sweating, anemia, paraneoplastic phenomena, thrombosis, etc.) or to further reduce the appearance or severity of side effects of the crystalline form.

Reference to "about" a value or parameter herein includes (and describes) variations that are directed to that value or parameter per se. For example, a description referring to "about Y" includes the description of "Y". When used in combination with measured values, "about" includes a range that encompasses at least the uncertainty associated with the method of measuring the particular value, and can include a range of plus or minus one or two standard deviations around the stated value. When used to describe estimated values or compound dosages, it includes a range of plus or minus 10% of the stated value, or in some embodiments a range of plus or minus 5% around the stated value. In particular, when used to describe results from PXRD, the term "about" refers to a data variation of +/−0.2 degrees (i.e. ° 2θ). When used to describe results from DSC, the term about refers to data variations of +/−3 degrees (i.e. ° C.).

As used herein and in the appended claims, the singular forms "a," "or," and "the" include plural referents unless the context clearly dictates otherwise. It is understood that aspect and variations described herein include "consisting" and/or "consisting essentially of" aspects and variations. The terms "a" and "an" do not denote a limitation of quantity, but rather denote the presence of at least one of the referenced item. The terms "a" and "an" are used interchangeable with "one or more" or "at least one". The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

The terms "salt form(s) of the invention", "these salt forms", "such salt form(s)", "the salt form(s)", and "the present salt form(s)" refer to salt forms described herein, such as an amorphous salt form or crystalline salt form. Furthermore, the present salt forms can modulate, i.e., inhibit or enhance, the biological activity of a CK2 protein, a Pim protein or both, and thereby is also referred to herein as a "modulator(s)" or "CK2 and/or Pim modulator(s)".

Unless defined otherwise or clearly indicated by context, all technical and scientific terms and abbreviations used herein have the same meaning as commonly understood by one of ordinary skill in the art to which this invention belongs.

Multiphasic Form of N-Methyl-2-(4-Methyl-1,4-Diazepan-1-Yl)Benzo[4,5]Imidazo[1,2-A][1,8]Naphthyridine-6-Carbaxomide (Compound I)

2-(4-methyl-[1,4]diazepan-1-yl)-1,7,11 b-triazabenzo[c]fluorene-6-carboxylic acid sodium salt (1A, 99 mg, 0.25 mmol), methylamine hydrochloride (25 mg, 0.38 mmol, 1.5 eq.), 1-[bis(dimethylamino)methylene]-1H-1,2,3-triazolo[4,5-b]pyridinium 3-oxide hexafluorophosphate (HATU, 144 mg, 0.38 mmol, 1.5 eq.) and diisopropylethylamine (49 mg, 0.38 mmol, 1.5 eq.) in N,N-dimethylformamide (5.0 mL) were combined and stirred at room temperature for 1 hour.

The reaction mixture was then poured into water (8 mL) and cooled to 4° C. for 16 h. The precipitate was collected and washed with 4:1 water: N,N-dimethylformamide (1 mL) and water (1 mL). The solid was suspended in water (200 μL) and 20% aqueous sodium carbonate (200 μL) was added. The mixture was stirred at room temperature for 1 hour. The solid was then collected and washed with water (3×1 mL) to give the multiphasic form of Compound (I) (16 mg, 0.041 mmol, 16%) as a yellow crystalline solid.

LCMS: 100%, Rt: 1.678 min, ESMS m/z 389.1 (M+H)$^+$.
$^1$H NMR (300 MHz, CDCl$_3$-d) δ 10.56-10.34 (m, 1H), 8.99 (d, J=8.1 Hz, 1H), 8.64 (s, 1H), 7.96 (d, J=9.0 Hz, 2H), 7.95 (d, J=7.8 Hz, 1H), 7.57 (t, J=7.8 Hz, 1H), 7.47 (t, J=7.8 Hz, 1H), 6.71 (d, J=9.0 Hz, 1H), 4.41-3.69 (m, 4H), 3.21 (d, J=4.8 Hz, 3H), 3.00-2.81 (m, 2H), 2.74-2.58 (m, 2H), 2.44 (s, 3H), 2.27-2.07 (m, 2H).

Multiphasic Form of N-Methyl-2-(4-Methyl-1,4-Diazepan-1-Yl)Benzo[4,5]Imidazo[1,2-A][1,8]Naphthyridine-6-Carbaxomide (Compound I)

Compound (I) is highly crystalline as shown by PXRD analysis (See, FIG. 1).

Figure 2:
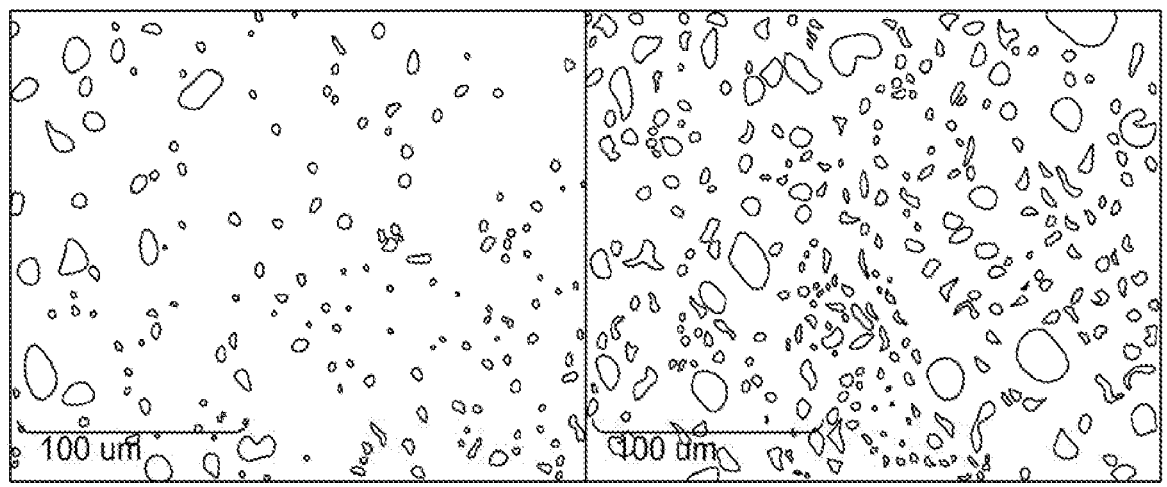
FIG. 2 depicts Polarized Light Microscopy (PLM) results of N-methyl-2-(4-methyl-1,4-diazepan-1-yl)benzo[4,5]imidazo[1,2-a][1,8]naphthyridine-6-carbaxomide (Compound (I)) in multiphasic form.

Polarized Light Microscopy shows Compound (I) consists of small birefringent particles of no defined morphology (See, FIG. 2).

Figure 3:
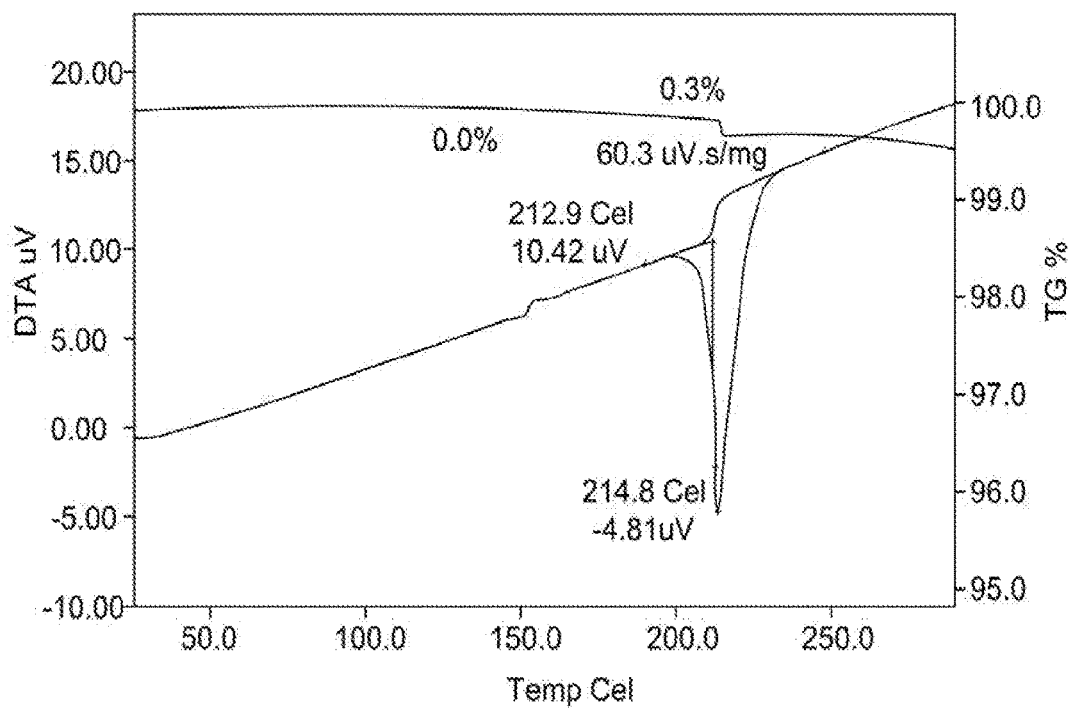
FIG. 3 depicts the Thermogravimetric Analysis (TGA) and Differential Scanning Calorimetry (DSC) thermogram of N-methyl-2-(4-methyl-1,4-diazepan-1-yl)benzo[4,5]imidazo[1,2-a][1,8]naphthyridine-6-carbaxomide (Compound (I)) in multiphasic form.

Thermogravimetric Analysis (TGA) shows no mass loss up to 150° C. while DT trace shows a sharp endotherm with an onset at 212.9° C. peaking at 214.8° C. (See, FIG. 3). No significant degradation is noted up to 200° C.

Figure 4:
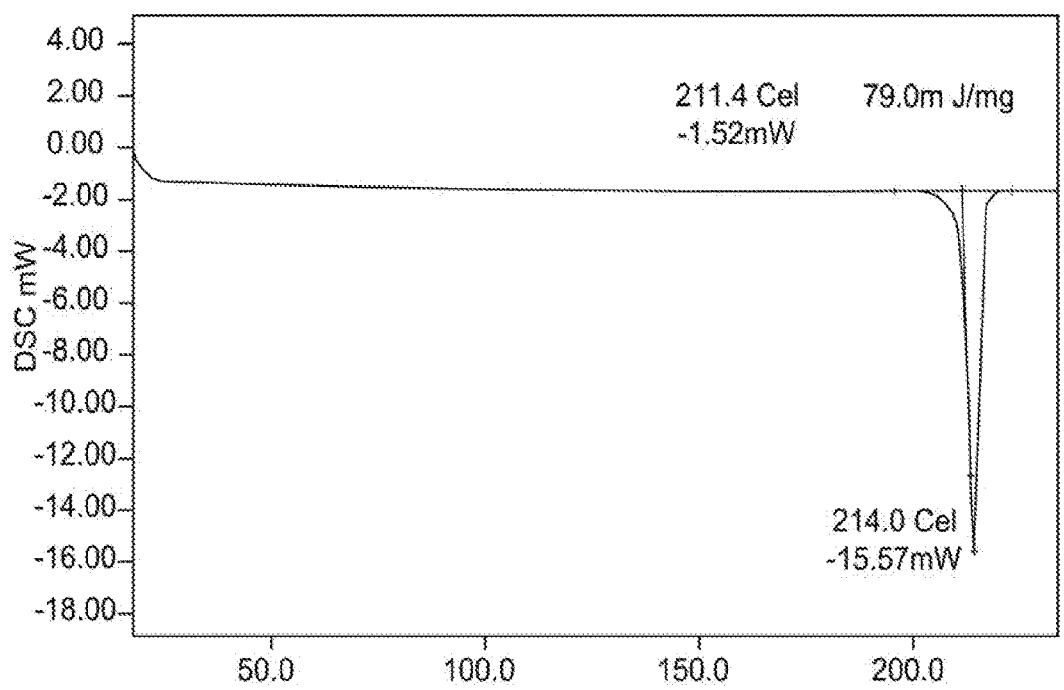
FIG. 4 depicts the Differential Scanning Calorimetry (DSC) thermogram (first heating cycle) of N-methyl-2-(4-methyl-1,4-diazepan-1-yl)benzo[4,5]imidazo[1,2-a][1,8]naphthyridine-6-carbaxomide (Compound (I)) in multiphasic form.
Figure 5:
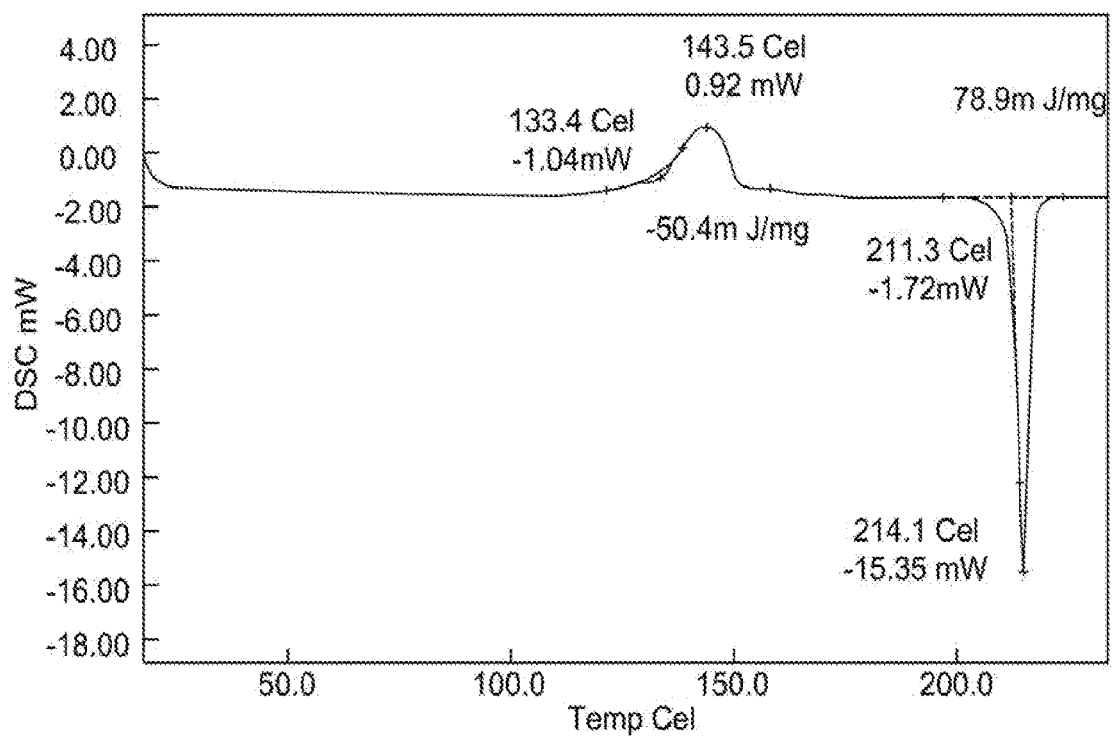
FIG. 5 depicts the Differential Scanning Calorimetry (DSC) thermogram (second heating cycle) of N-methyl-2-(4-methyl-1,4-diazepan-1-yl)benzo[4,5]imidazo[1,2-a][1,8]naphthyridine-6-carbaxomide (Compound (I)) in multiphasic form.

Differential Scanning Calorimetry (DSC) analysis shows a sharp, well defined endothermic peak on first heating cycle with an onset at 211.4° C. peaking at 214° C. (See, FIG. 4). A small exothermic peak is also observed on the second heating cycle beginning at 133.4° C. and peaking at 143.5° C., and may represent re-crystallization (See, FIG. 5). An endothermic peak is observed to follow this, with an onset at 211.3° C. and a peak at 214.1° C., indicative of a melting event.

Figure 6:
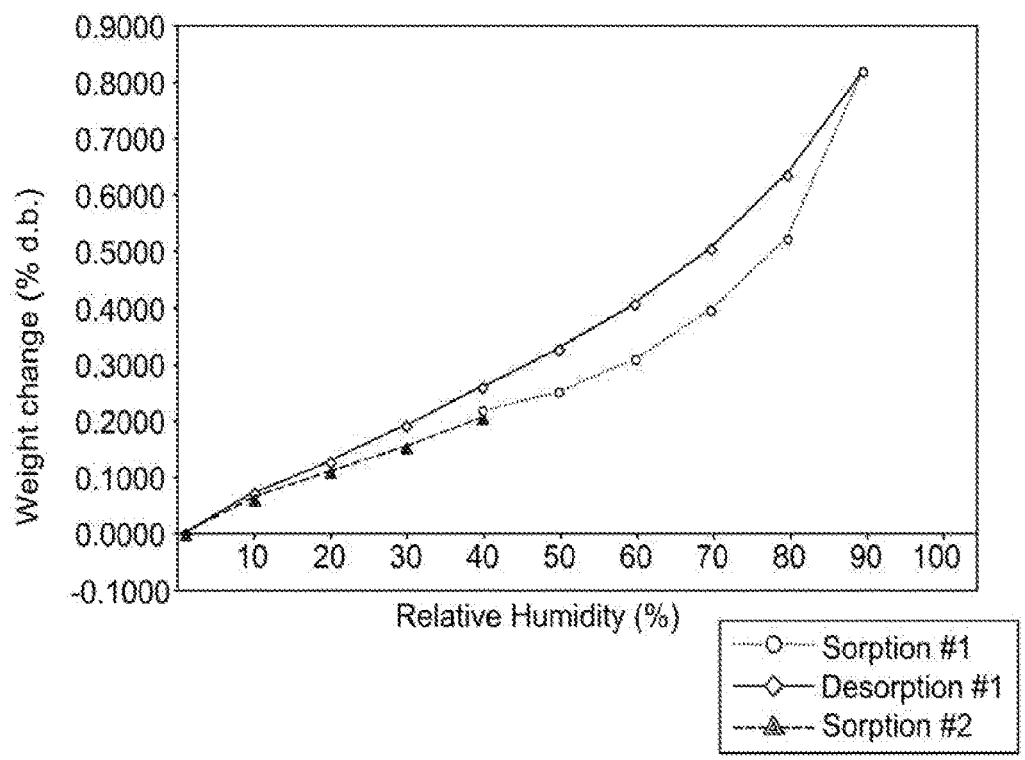
FIG. 6 depicts Gravimetric Vapor Sorption (GVS) data of N-methyl-2-(4-methyl-1,4-diazepan-1-yl)benzo[4,5]imidazo[1,2-a][1,8]naphthyridine-6-carbaxomide (Compound (I)) in multiphasic form.

Gravimetric Vapor Sorption (GVS) analysis also demonstrates that Compound (I) exhibits a mass uptake of 0.8% up to 90% relative humidity (RH), thereby suggesting Compound (I) is non-hygroscopic (See, FIG. 6).

Crystalline Form 1 of N-Methyl-2-(4-Methyl-1,4-Diazepan-1-Yl)Benzo[4,5]Imidazo[1,2-A][1,8]Naphthyridine-6-Carbaxomide (Compound I)

Crystalline Form 1 of Compound (I) was made by preparing a mixture (e.g., slurry) of Compound (I) in acetone by adding 200 mg of Compound (I) to 2.4 mL of acetone. The resultant slurry was then temperature cycled from about 5° C. to 25° C. for a period of about 72 hours. This procedure was repeated using acetone, acetonitrile, tBME, dimethylformamide, ethanol, ethyl acetate, heptane, methanol, propan-2-ol, tetrahydrofuran and toluene as the solvent for the slurry (See, FIG. 8).

Figure 18:
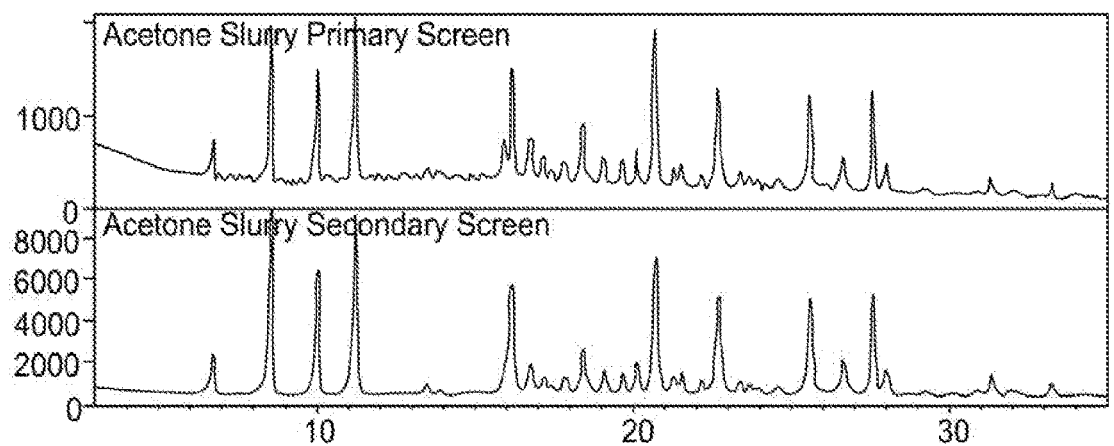
FIG. 18 depicts the powder X-ray diffraction pattern (PXRD) of Form 1 from the acetone slurry in the primary crystal form screen (top); and the powder X-ray diffraction pattern (PXRD) of Form 1 from the acetone slurry in the secondary crystal form screen (bottom).

Form 1 was also reproduced on a larger scale from an acetone slurry. PXRD analysis shows the clean formation of Form 1 to be reproducible. The PXRD 2θ diffractogram is observed to be similar to the multiphasic starting material with multiple peak differences, most notably the absence of the peak at 2θ=ca. 12° (See, FIG. 18).

Figure 19:
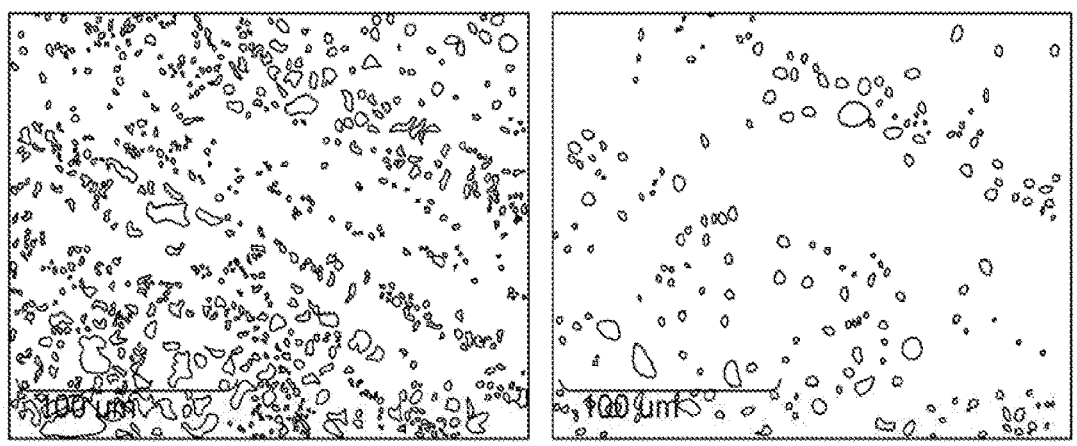
FIG. 19 depicts Polarized Light Microscopy (PLM) results of Form 1 pre-drying.
Figure 20:
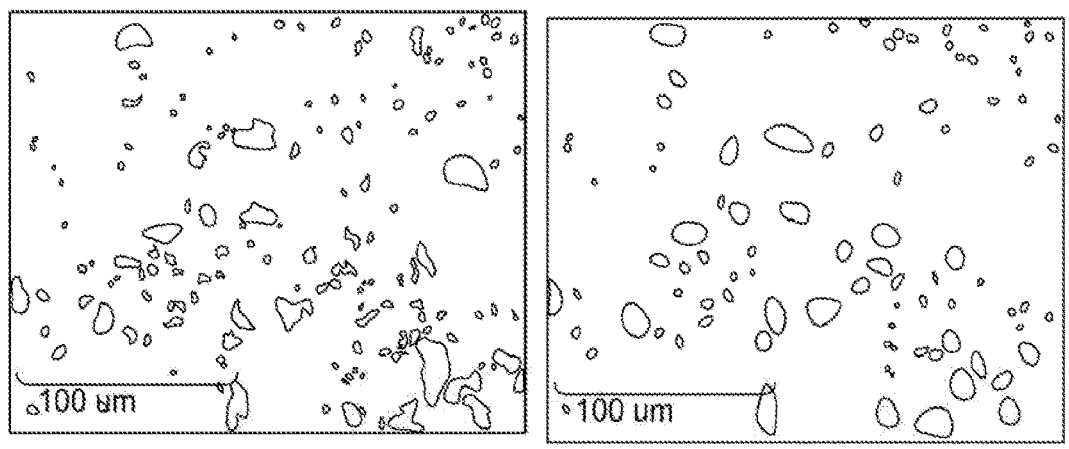
FIG. 20 depicts Polarized Light Microscopy (PLM) results of Form 1 post-drying.

PLM analysis shows particles which exhibit birefringence with no defined morphology both pre and post drying (See, FIG. 19 and FIG. 20).

Figure 21:
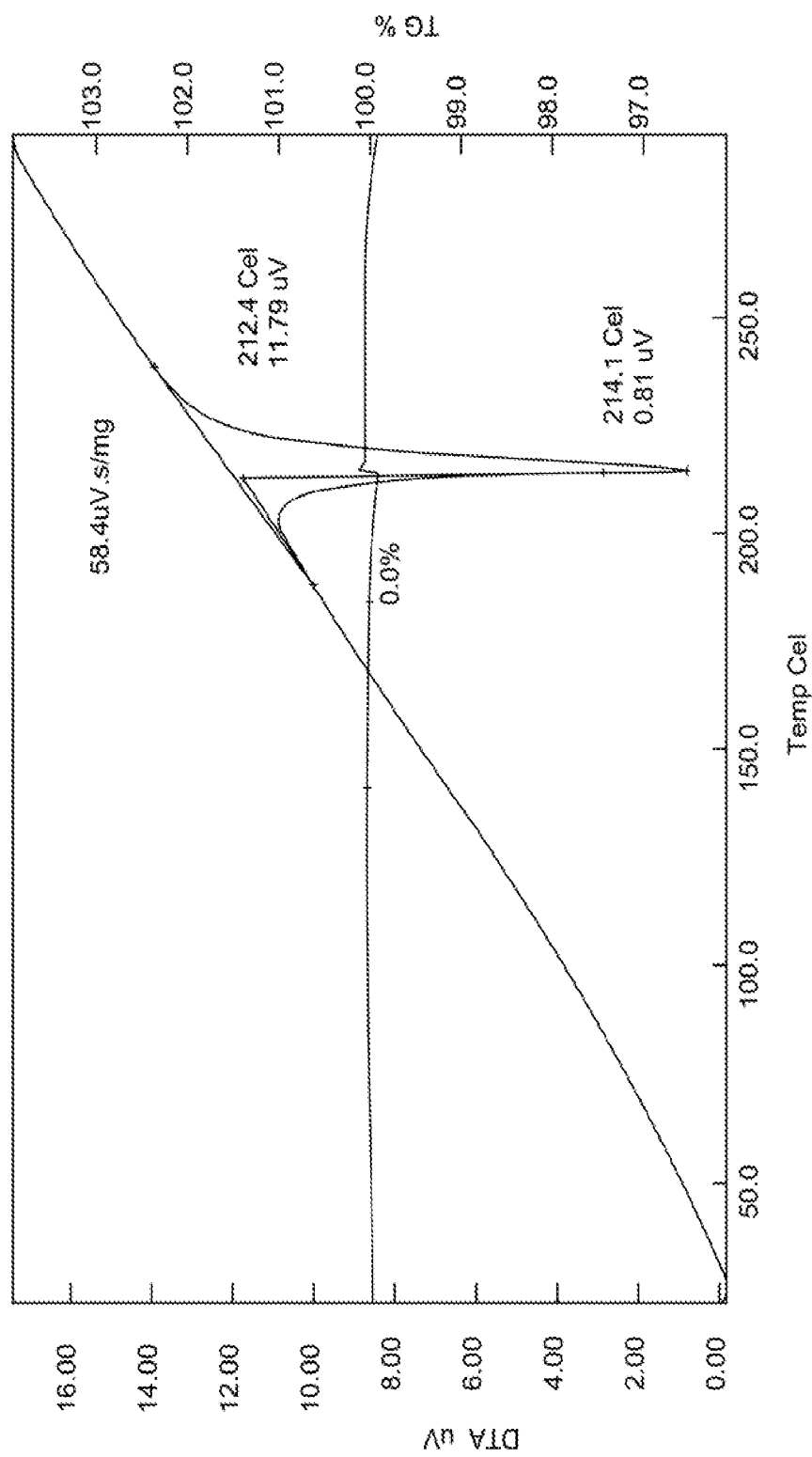
FIG. 21 depicts the Thermogravimetric Analysis (TGA) and Differential Thermal Analysis (DTA) of Form 1.

TGA (See, FIG. 21) shows no mass loss up to up to an endothermic event with peak at 214.1° C. (DTA trace). A small increase in mass is observed around this endotherm.

DSC analysis (first heating cycle) shows an endotherm with onset at 211.6° C. and peak at 214.9° C. (See, FIG. 22). This endothermic event is likely associated with melting of the crystallized Compound (I) with associated enthalpy of 82.6 mJ/mg.

Figure 23:
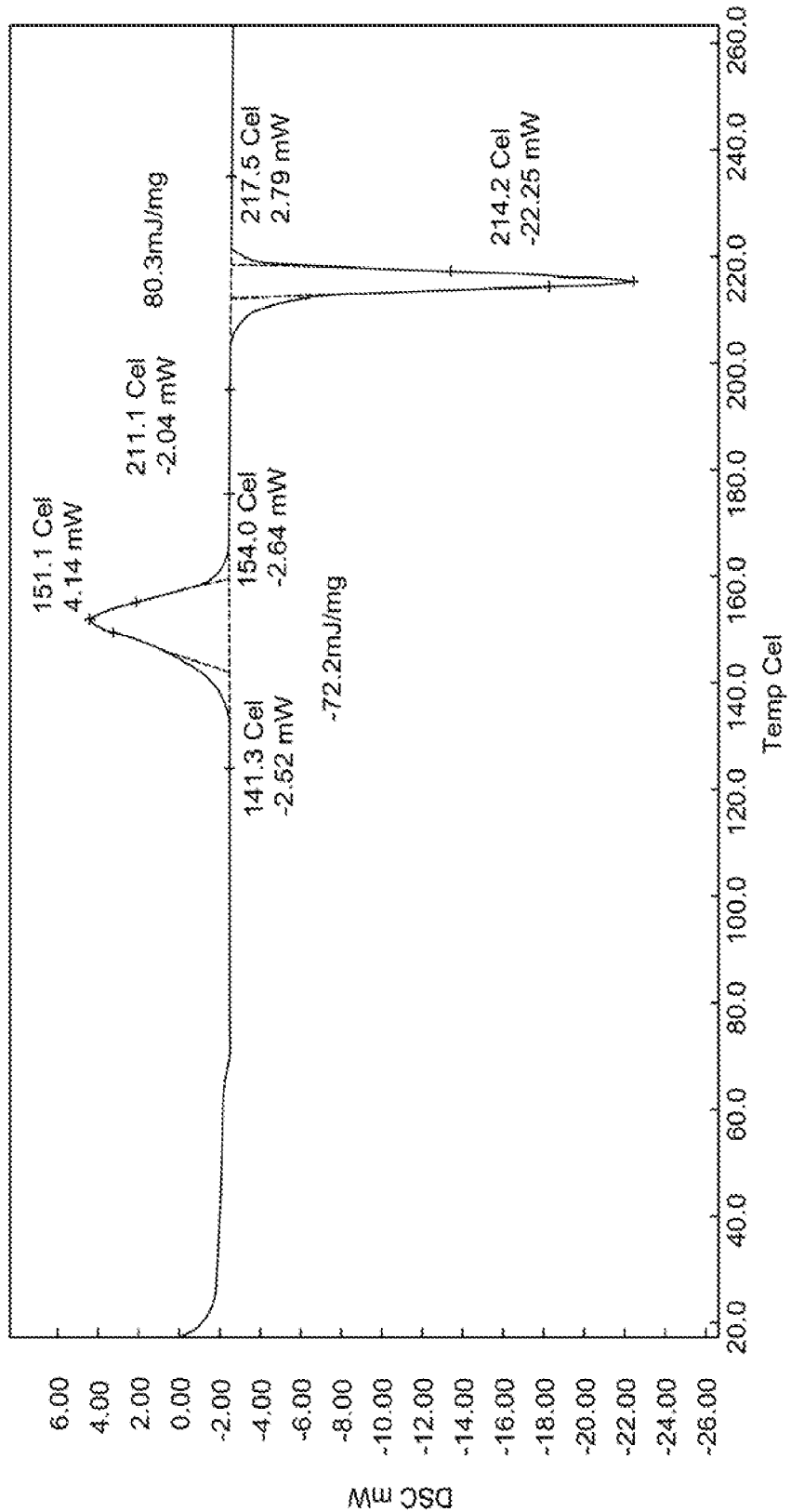
FIG. 23 depicts the Differential Scanning Calorimetry (DSC) thermogram ($2^{nd}$ heating cycle) of Form 1.

On the second heating cycle, an exothermic event is also observed with onset of 141.3° C. and peak at 151.1° C., this is attributed to the re-crystallization of Form 1. A second endothermic event was observed, with onset at 211.1° C. and peak at 214.2° C. (See, FIG. 23). This correlates closely to the endothermic event on the first heating cycle, and is likely associated with the melt of the crystallized Compound (I).

Figure 24:
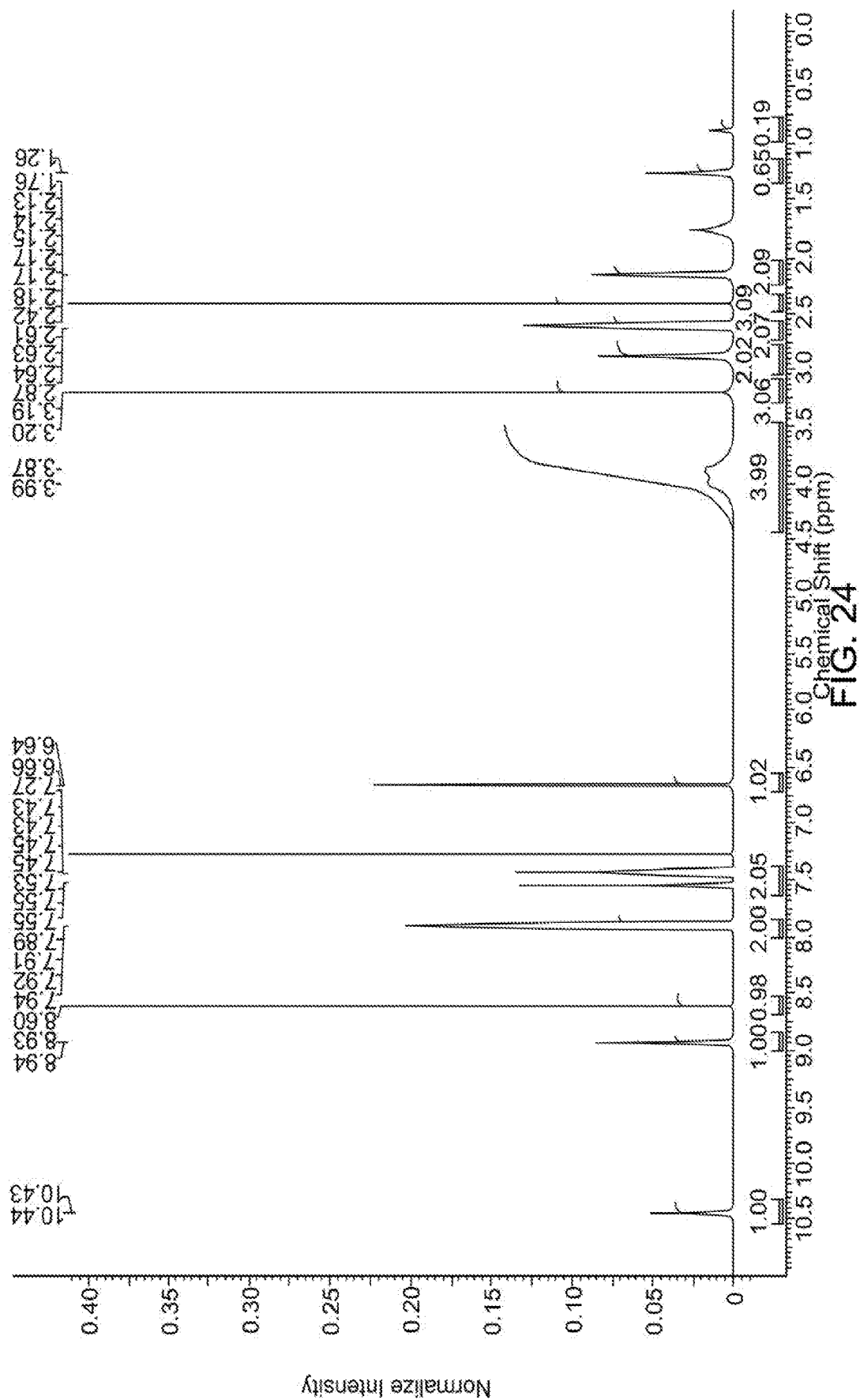
FIG. 24 depicts the $^1$H Nuclear Magnetic Resonance (NMR) analysis (CDCl$_3$, 500 MHz) of Form 1.

$^1$H NMR analysis confirmed structural integrity of Compound (I) when crystallized as Form 1 (See, FIG. 24).

Figure 61:
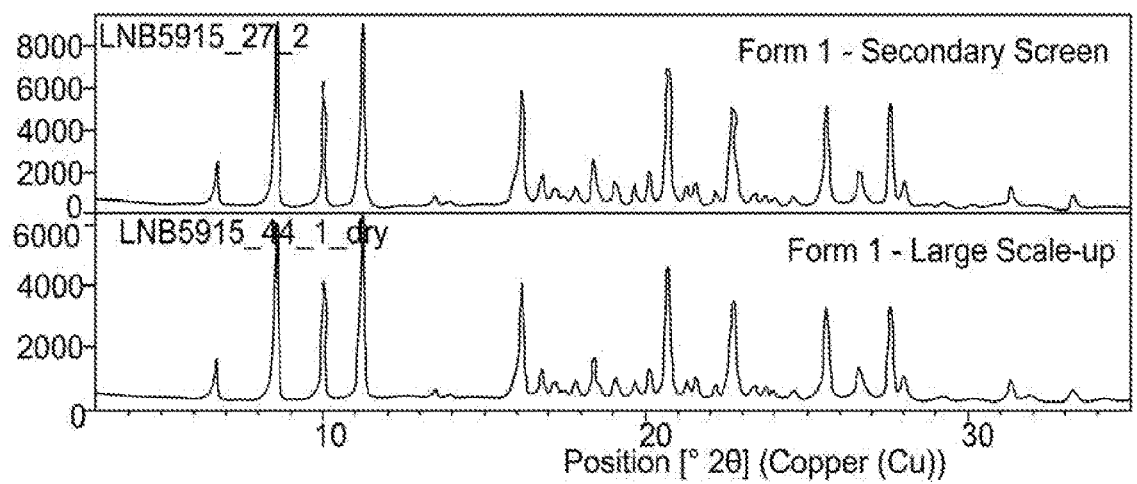
FIG. 61 depicts the powder X-ray diffraction pattern (PXRD) of Form 1 from the secondary screen (top) and the large scale-up (bottom).

Form 1 was reproduced on a 1 g scale by acetone slurry. PXRD analysis confirmed Form 1 was reproducible on a 1 g scale (See, FIG. 61).

Figure 62:
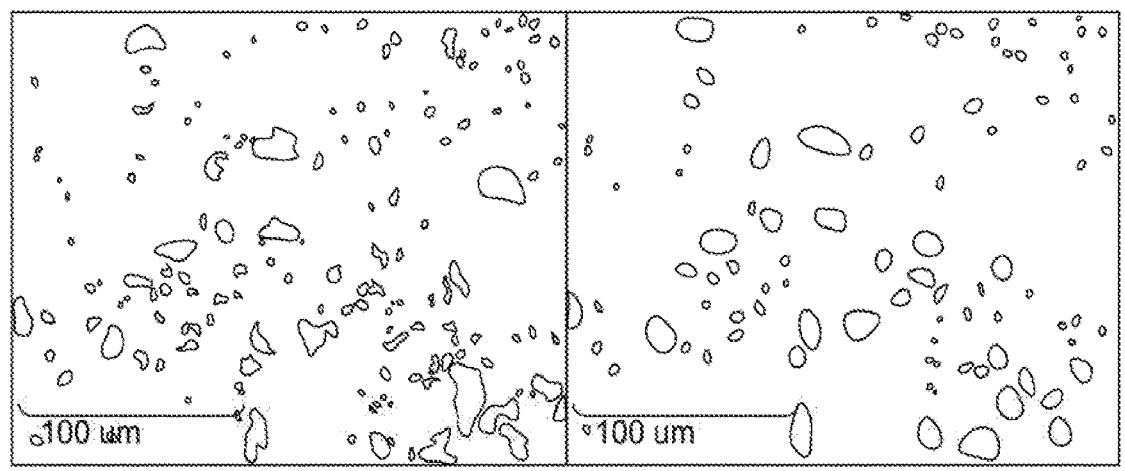
FIG. 62 depicts Polarized Light Microscopy (PLM) results of Form 1 from the large scale-up post-drying.

PLM analysis shows the presence of small birefringent particles of no defined morphology (See, FIG. 62).

Figure 63:
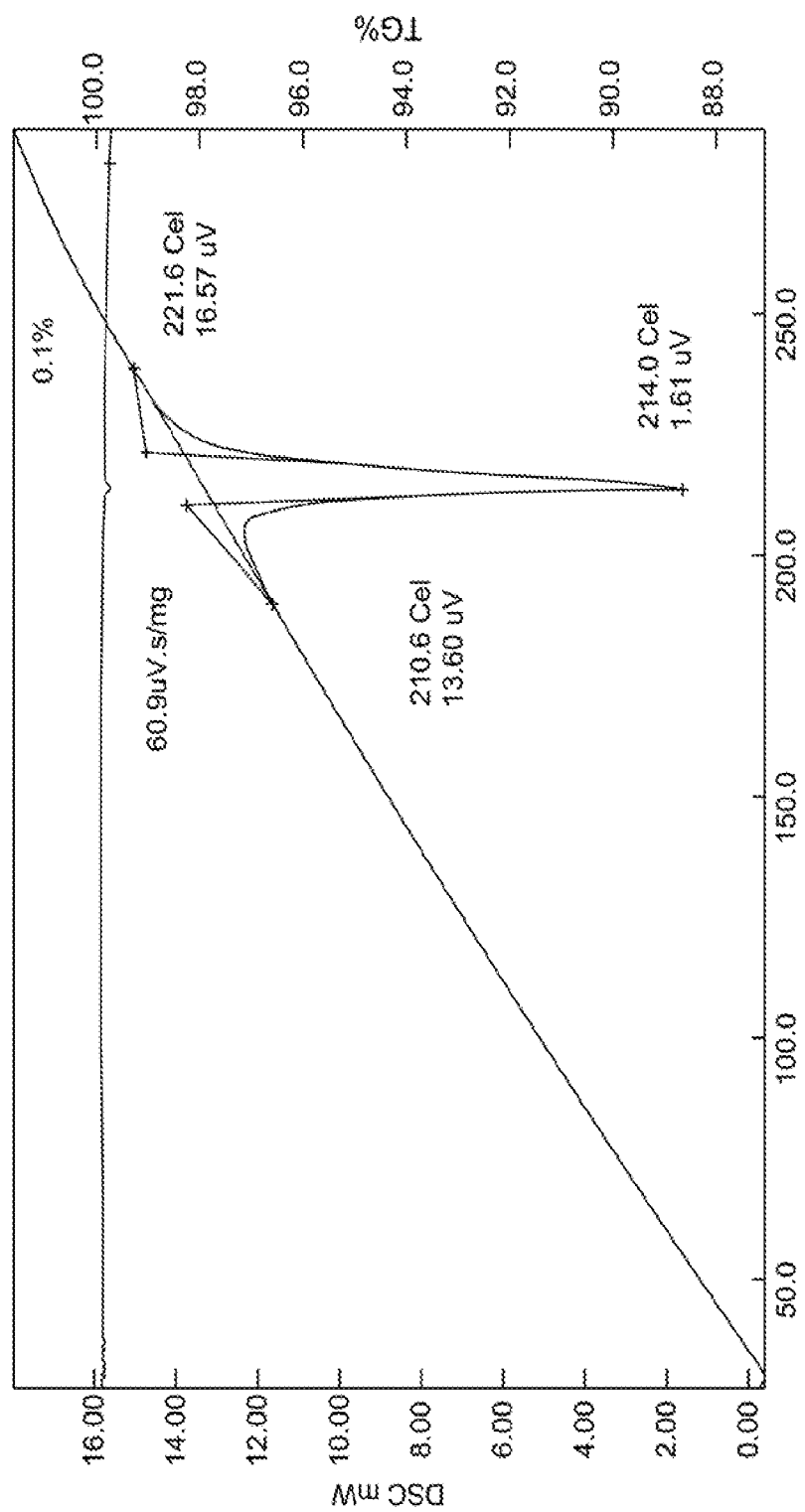
FIG. 63 depicts the Thermogravimetric Analysis (TGA) and Differential Thermal Analysis (DTA) of Form 1 from the large scale-up.

TGA shows no mass loss up to up to an endothermic event with peak at 214.1° C. (DTA trace) (See, FIG. 63). A small decrease in mass is observed around this endotherm.

Figure 64:
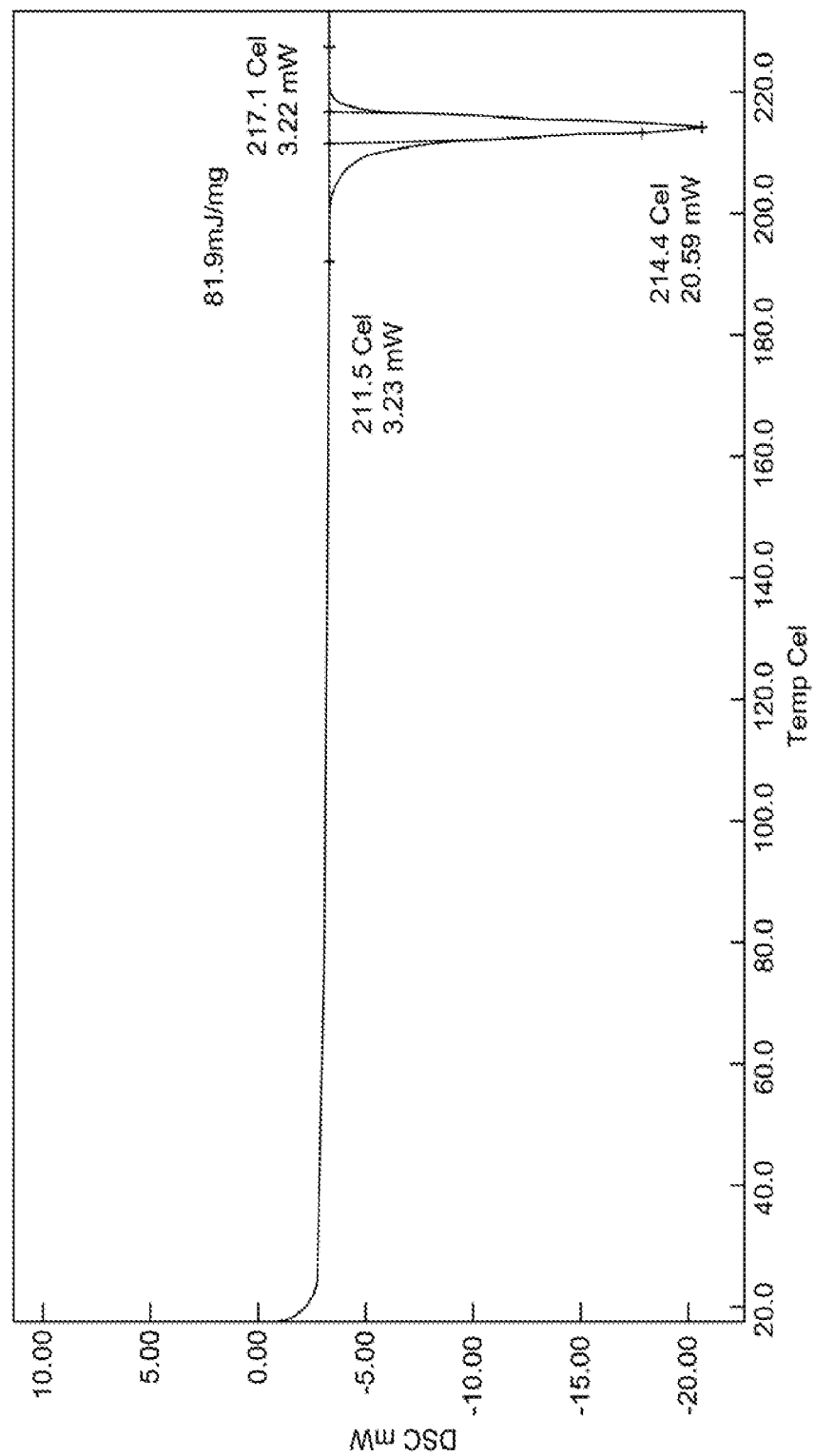
FIG. 64 depicts the Differential Scanning Calorimetry (DSC) thermogram (1$^{st}$ heating cycle) of Form 1 from a large scale-up.

DSC analysis of the first heating cycle shows an endotherm with onset of 211.5° C. and peak at 214.4° C. (See, FIG. 64). This endothermic event is likely associated with melting of Compound (I).

Figure 65:
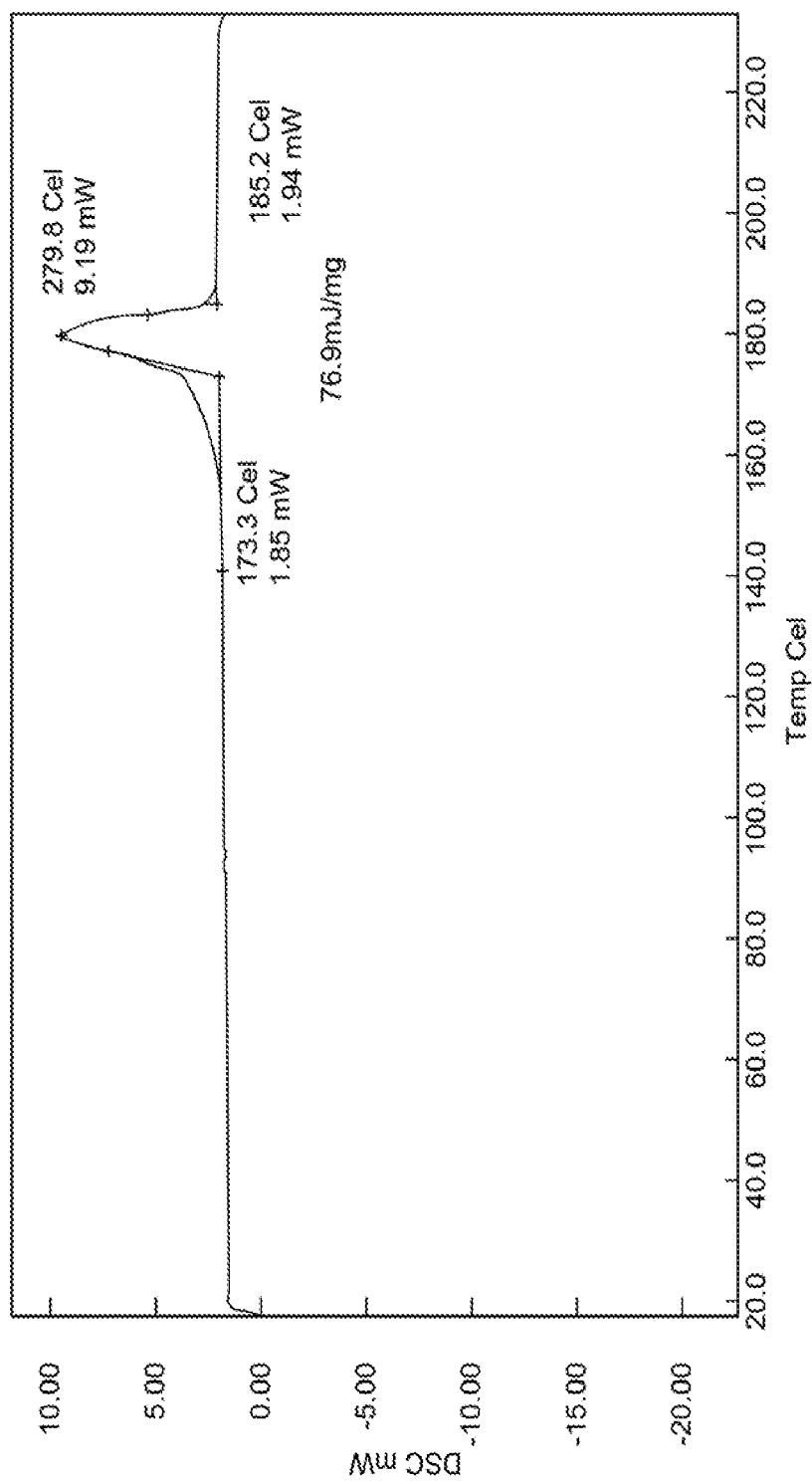
FIG. 65 depicts the Differential Scanning Calorimetry (DSC) thermogram (cooling cycle) of Form 1 from a large scale-up.

On the cooling cycle an exothermic event is observed with onset of 185.2° C., and peak at 179.8° C. (See, FIG. 65). This is likely due to re-crystallization of Compound (I).

Figure 66:
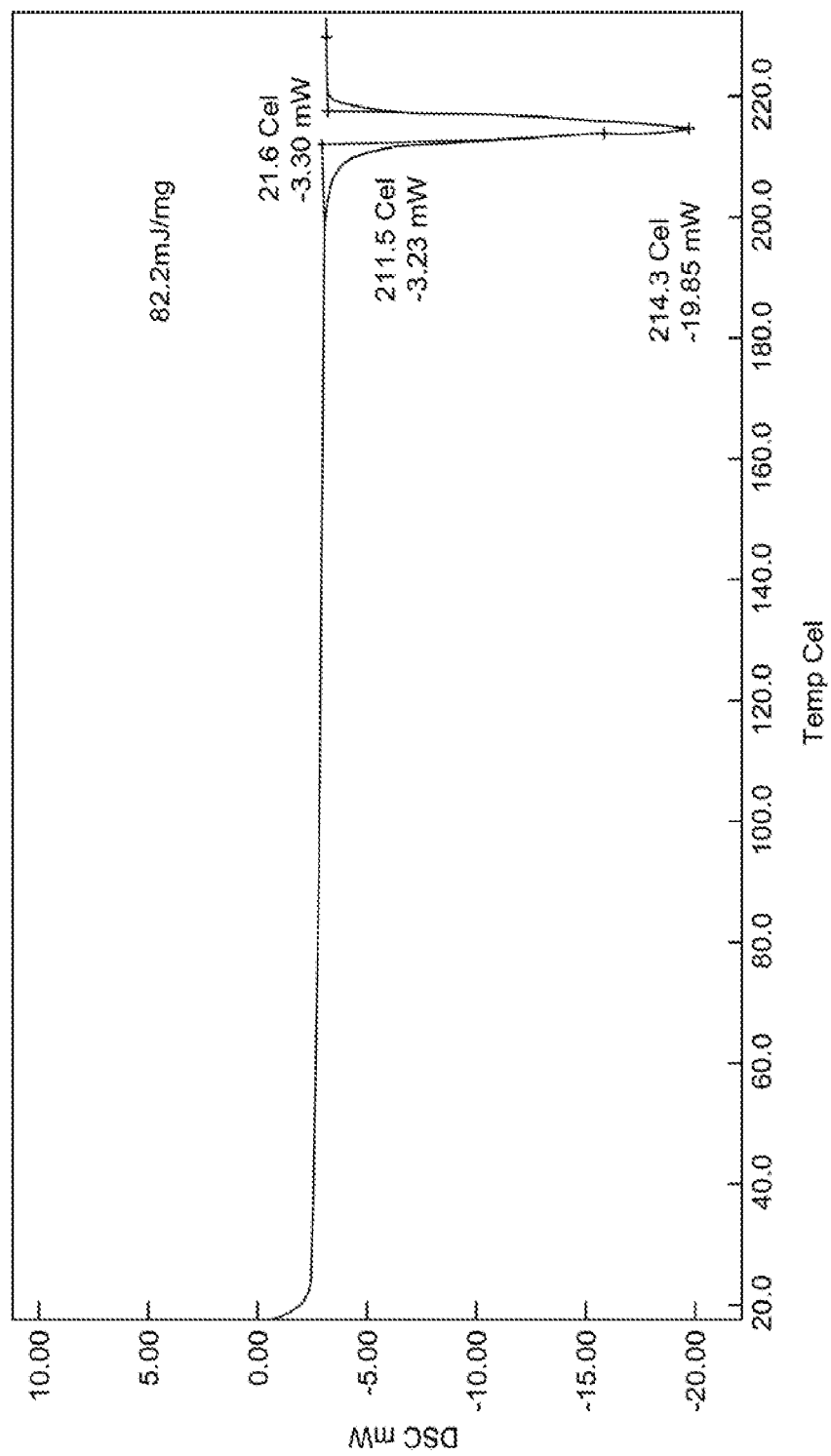
FIG. 66 depicts the Differential Scanning Calorimetry (DSC) thermogram (2$^{nd}$ heating cycle) of Form 1 from a large scale-up.

On the second heating cycle an endotherm is observed with onset of 211.5° C., and peak at 214.3° C. This is likely due to melting of the re-crystallized Compound (I) (See, FIG. 66).

Figure 67:
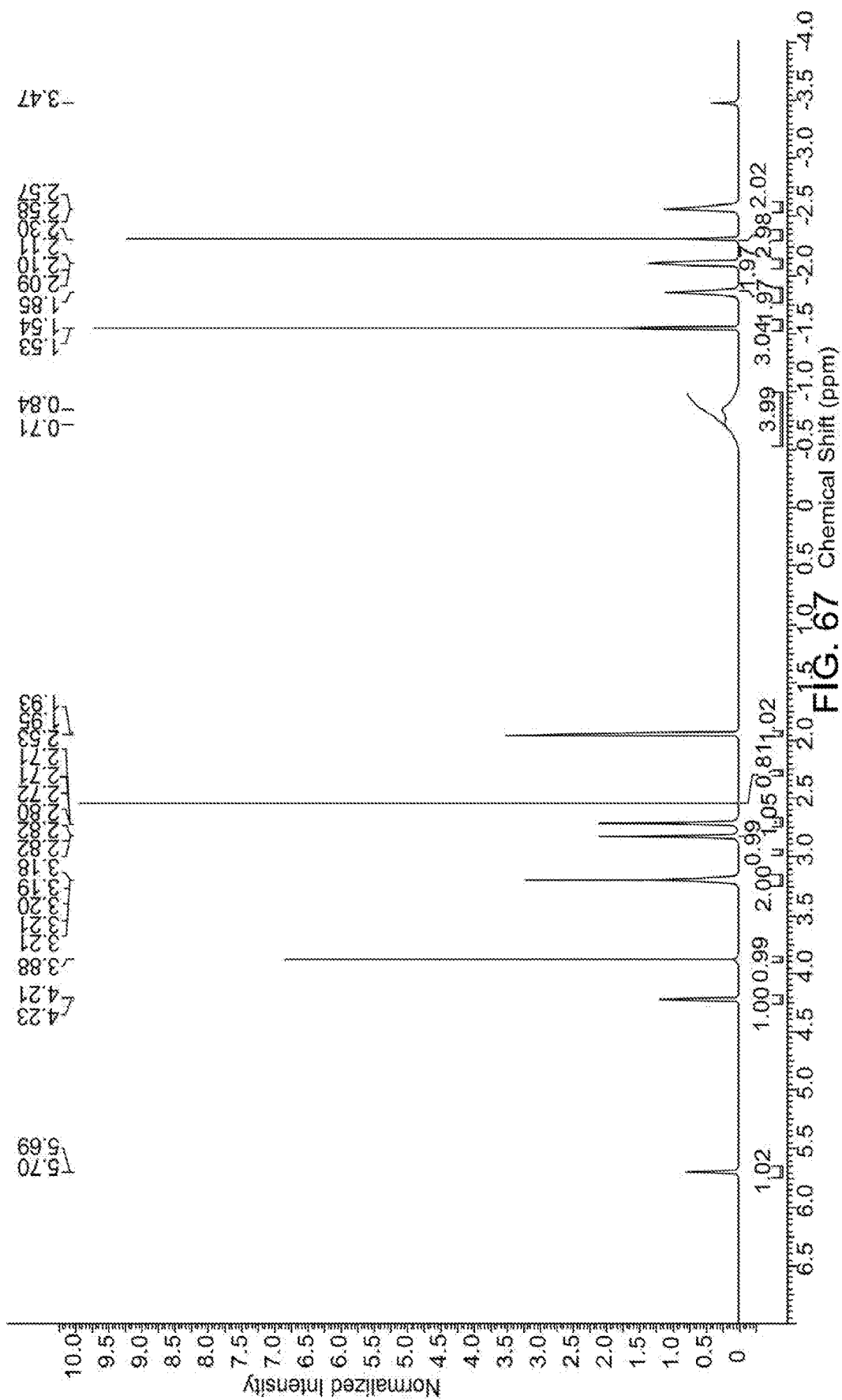
FIG. 67 depicts the $^1$H NMR analysis (CDCl$_3$, 500 MHz) of Form 1 from a large scale-up.

FIG. 67 provides results from $^1$H NMR analysis (CDCL$_3$ 500 MHz) of Form 1 from the large scale-up.

Form 1 is stable and maintains its form after 7-day storage under ambient conditions (closed vial) and 40° C./75% RH (closed vial). Results of a post-storage PXRD analysis of Form 1 are provided in FIG. 52.

Figure 68:
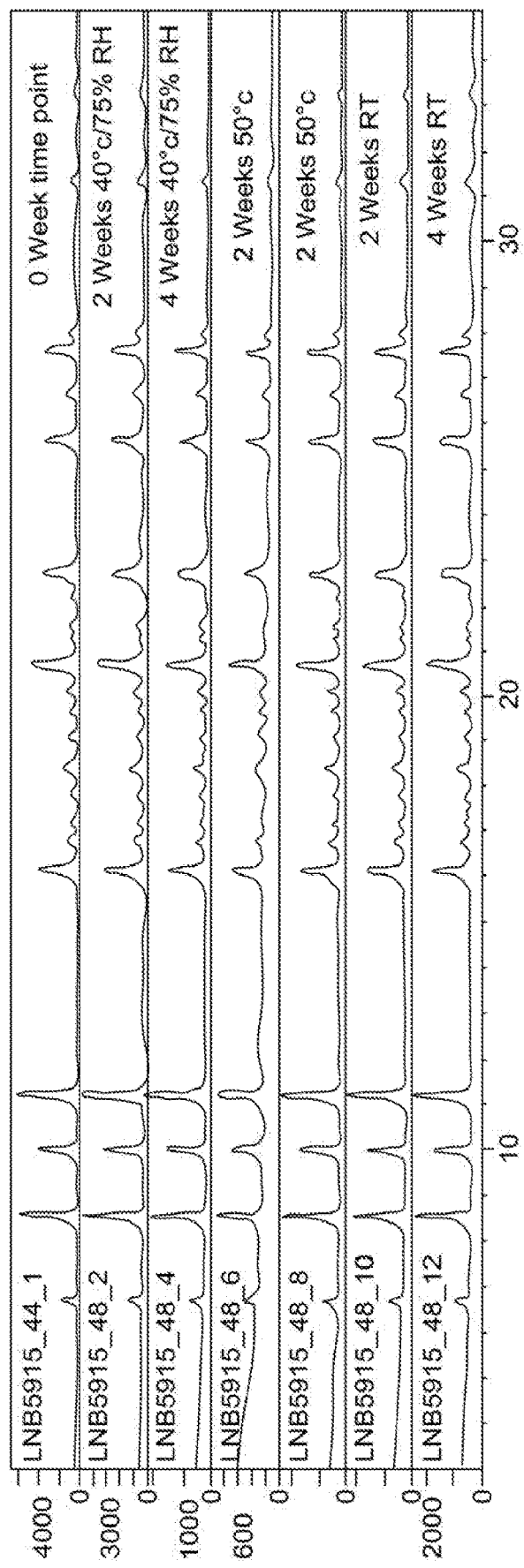
FIG. 68 depicts the powder X-ray diffraction pattern (PXRD) of Form 1 at the 0 week time point (top); after 2 weeks at 40° C. and 75% relative humidity (2$^{nd}$ from top); after 4 weeks at 40° C. and 75% relative humidity (3$^{rd}$ from top); after 2 weeks at 50° C. (4$^{th}$ and 5$^{th}$ from top); after 2 weeks at room temperature (6$^{th}$ from top); and after 4 weeks at room temperature (7$^{th}$ from top, i.e, bottom).

Form 1 is stable and maintains its form after 2 weeks and after 4 weeks of storage under 40° C./75% RH, 50° C. and RT. PXRD diffractograms show Form 1 does not change form nor undergo a change in crystallinity post stability testing (See, FIG. 68).

The NMR analysis (CDCl$_3$ 500 MHz) provided in FIGS. 69-74 demonstrates that Form 1 maintains its structural integrity and does not degrade post further stability testing.

Figure 69:
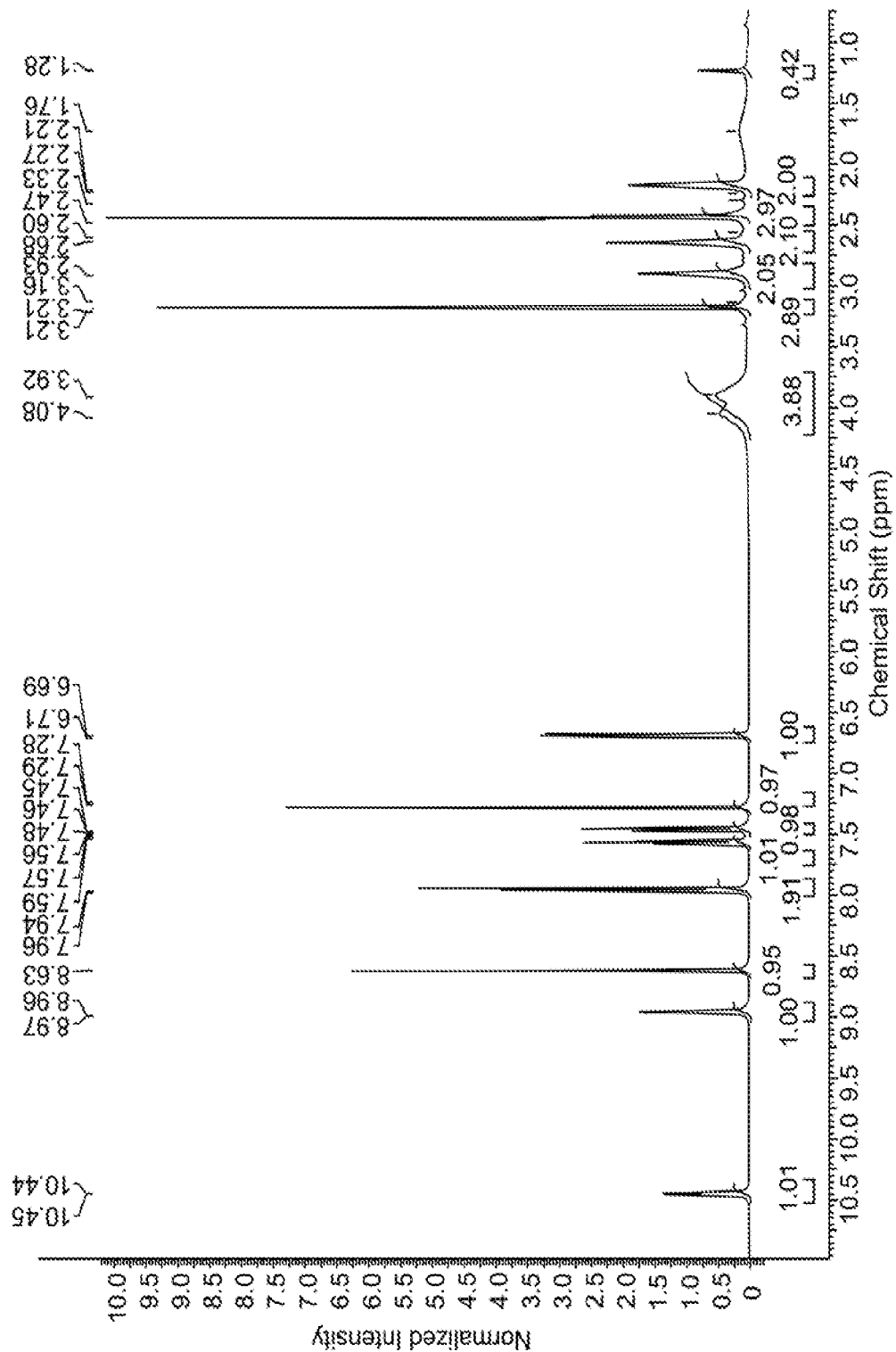
FIG. 69 depicts the $^1$H NMR analysis (CDCl$_3$, 500 MHz) of Form 1 after two (2) weeks of storage at 40° C. and 75% relative humidity.
Figure 70:
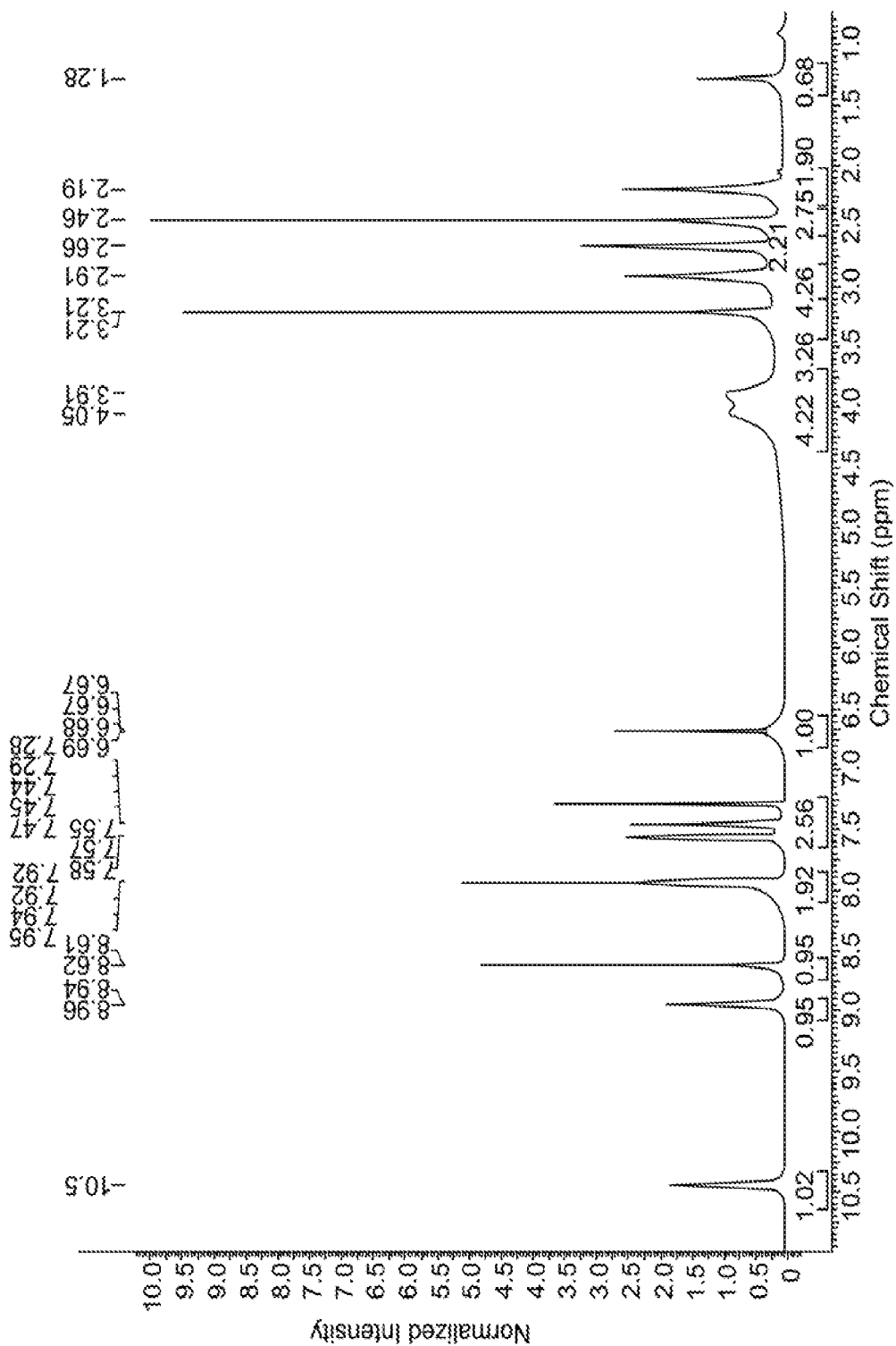
FIG. 70 depicts the $^1$H NMR analysis (CDCl$_3$, 500 MHz) of Form 1 after four (4) weeks of storage at 40° C. and 75% relative humidity.
Figure 71:
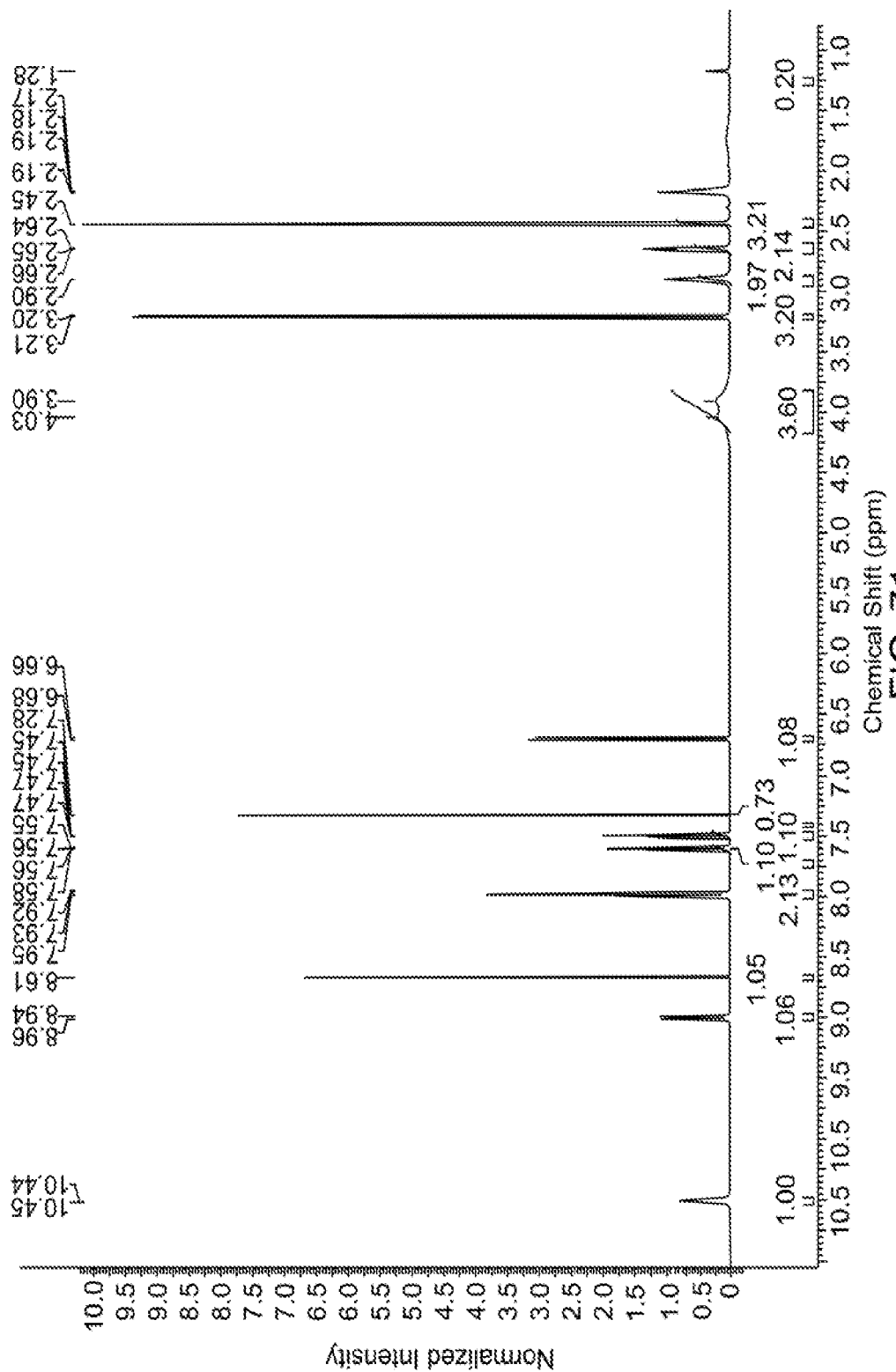
FIG. 71 depicts the $^1$H NMR analysis (CDCl$_3$, 500 MHz) of Form 1 after two (2) weeks of storage at 50° C.
Figure 72:
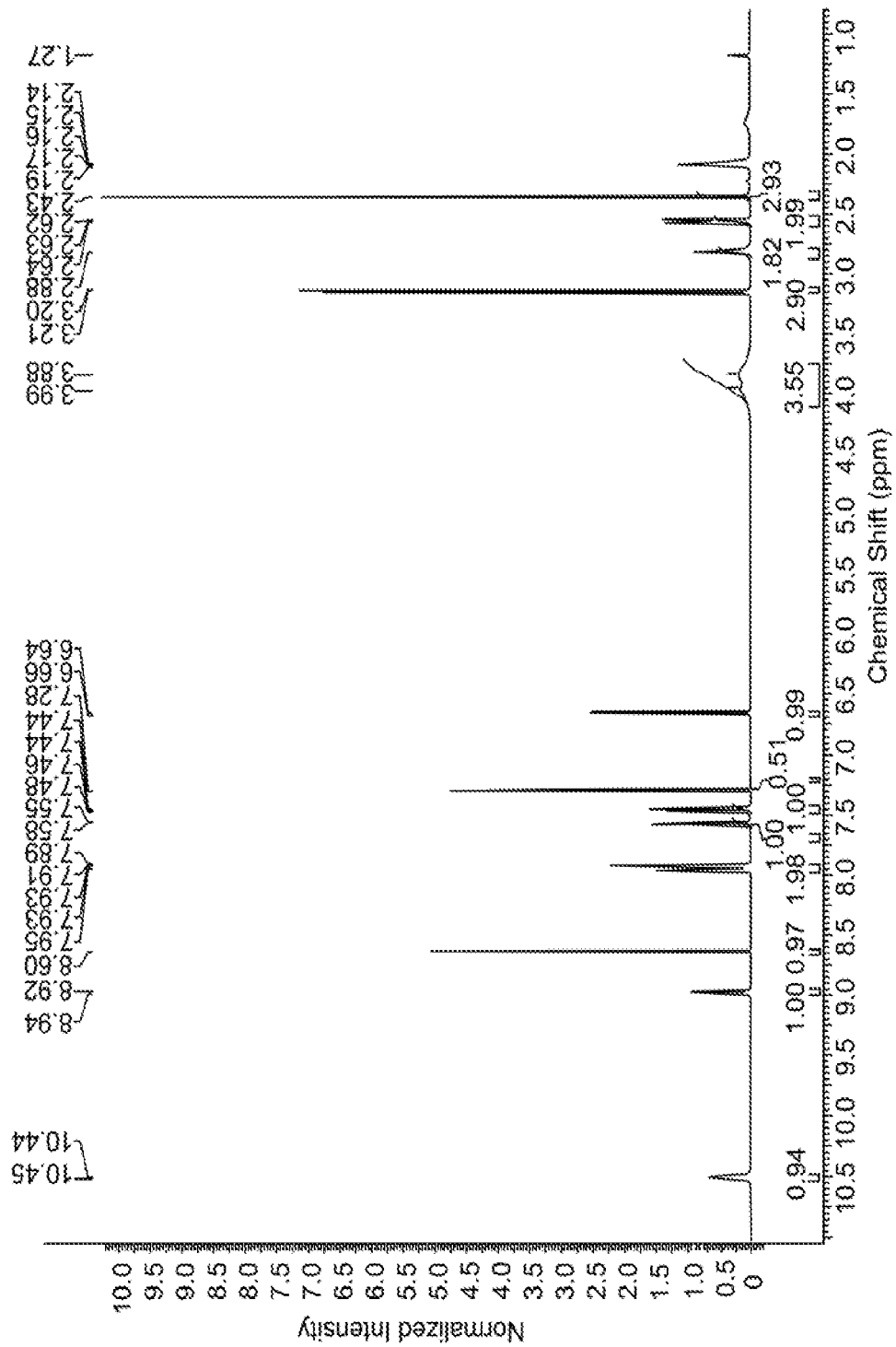
FIG. 72 depicts the $^1$H NMR analysis (CDCl$_3$, 500 MHz) of Form 1 after four (4) weeks of storage at 50° C.
Figure 73:
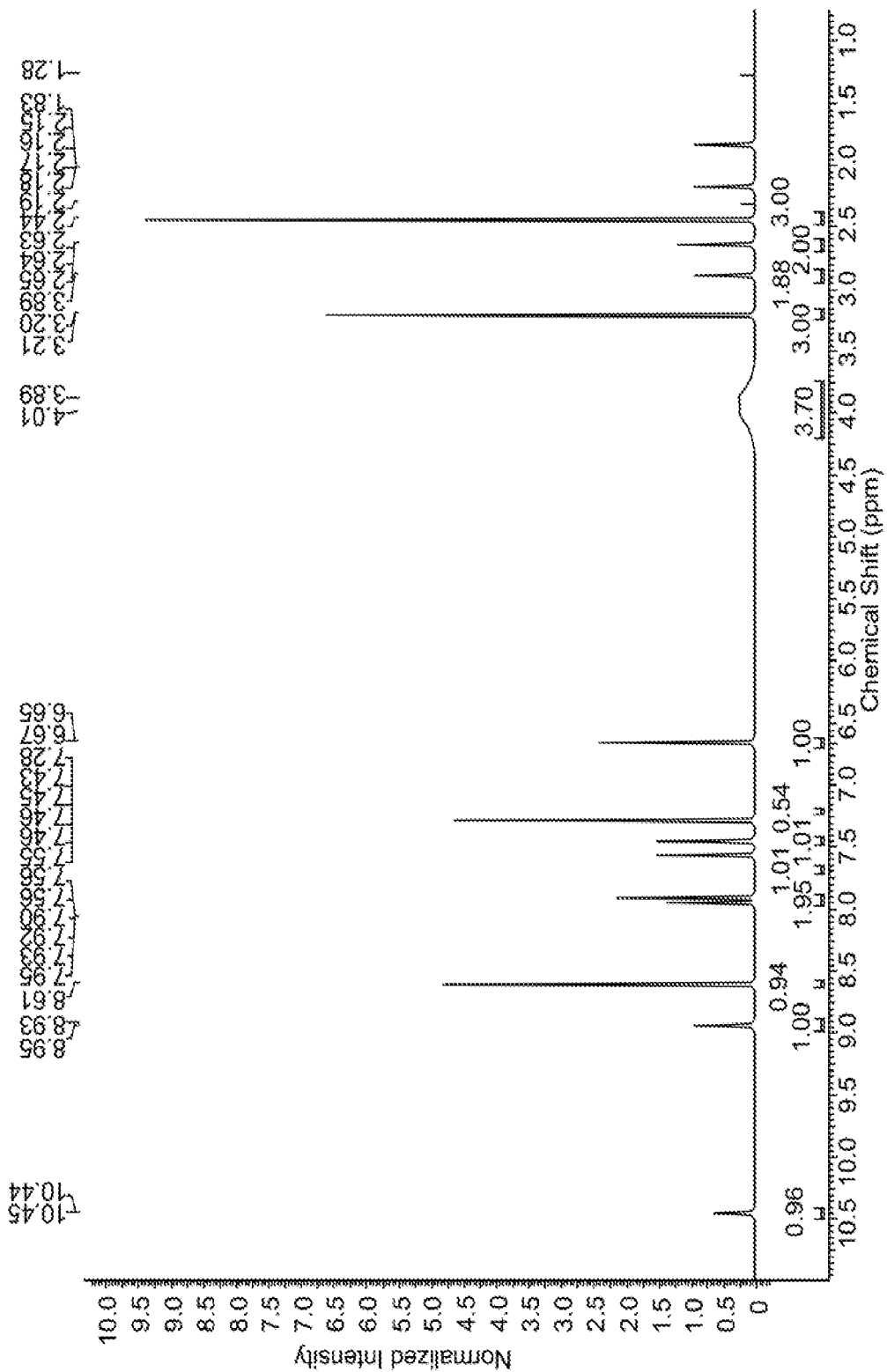
FIG. 73 depicts the $^1$H NMR analysis (CDCl$_3$, 500 MHz) of Form 1 after two (2) weeks of storage at room temperature.
Figure 74:
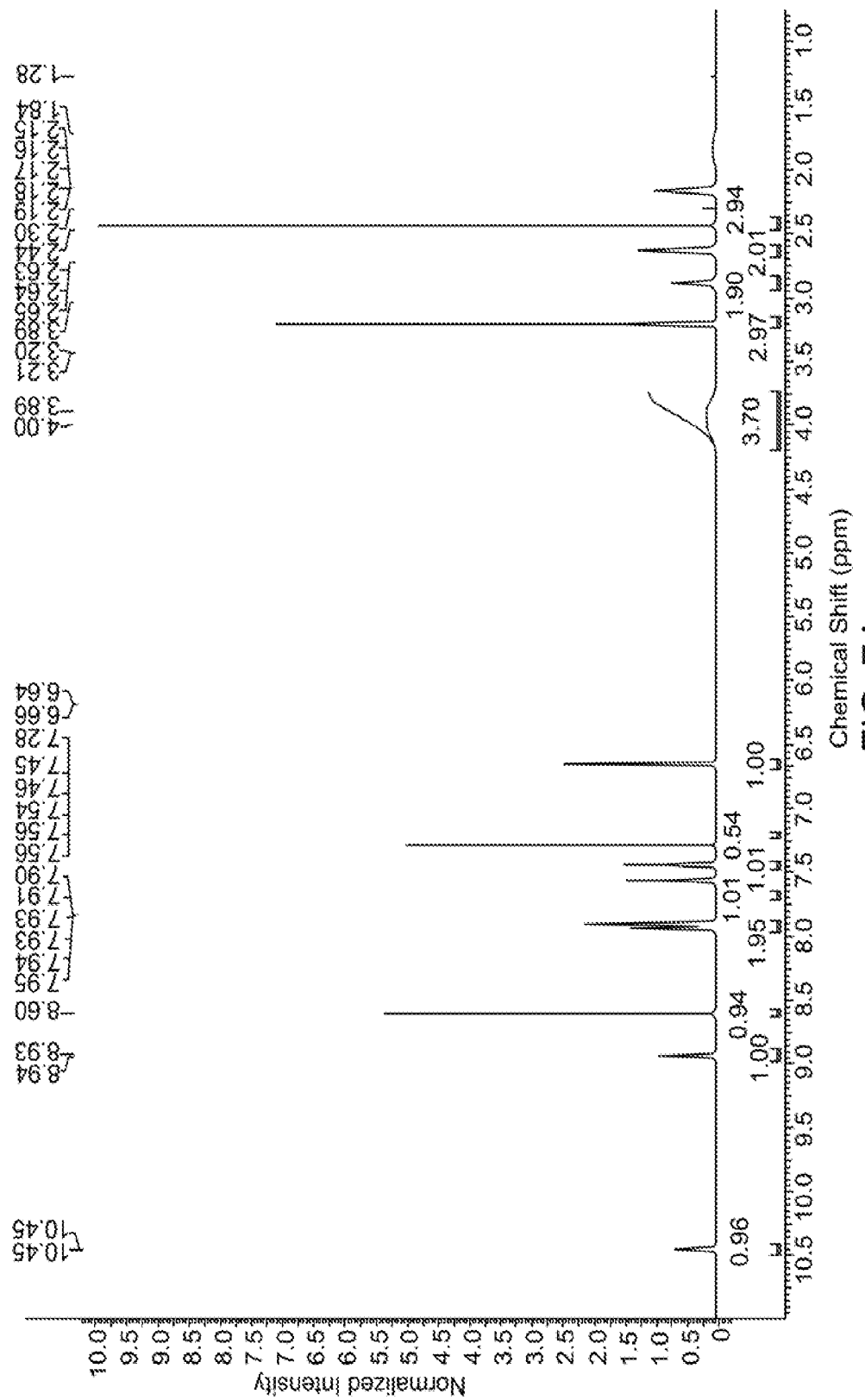
FIG. 74 depicts the $^1$H NMR analysis (CDCl$_3$, 500 MHz) of Form 1 after four (4) weeks of storage at room temperature.

Specifically, FIG. 69 shows $^1$HMR analysis of Form 1 after 2 weeks of storage at 40° C. and 75% Relative Humidity; FIG. 70 shows $^1$HMR analysis of Form 1 after 4 weeks of storage at 40° C. and 75% Relative Humidity; FIG. 71 shows $^1$HMR analysis of Form 1 after 2 weeks of storage at 50° C.; FIG. 72 shows $^1$HMR analysis of Form 1 after 4 weeks of storage at 50° C.; FIG. 73 shows $^1$HMR analysis of Form 1 after 2 weeks of storage at room temperature; and FIG. 74 shows $^1$HMR analysis of Form 1 after 4 weeks of storage at room temperature.

The High Performance Liquid Chromatography (HPLC) analysis provided in Table 5 and FIGS. 75-80 demonstrate that Form 1 maintains high levels of purity at 40° C. and 75% Relative Humidity; at 50° C. and room temperature at both 2 and 4 week time points.

Figure 75:
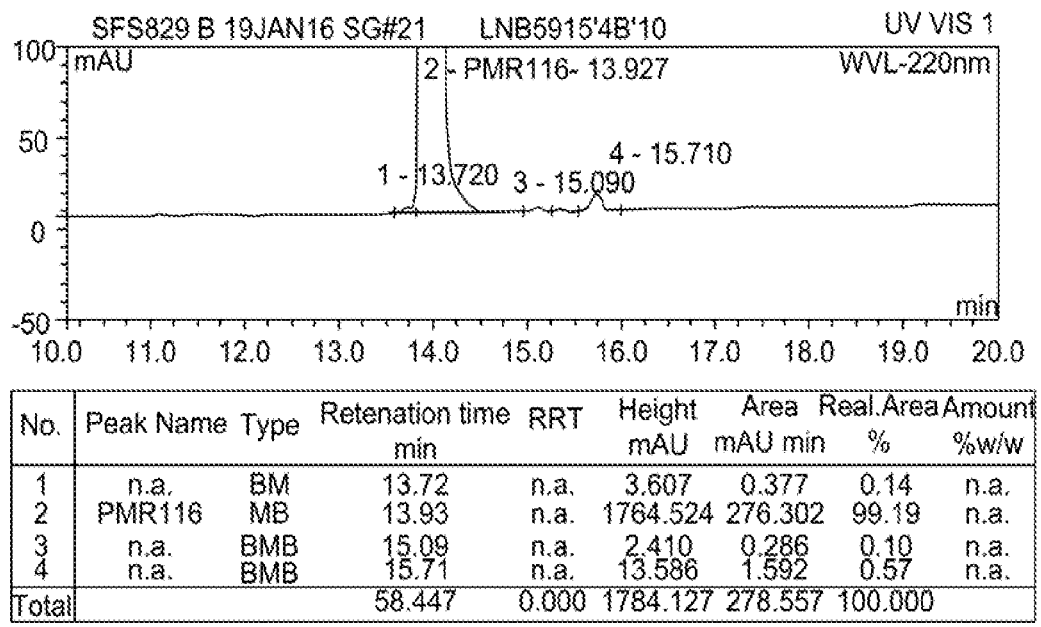
FIG. 75 depicts the High Performance Liquid Chromatography (HPLC) purity analysis of Form 1 after two (2) weeks at room temperature.
Figure 76:
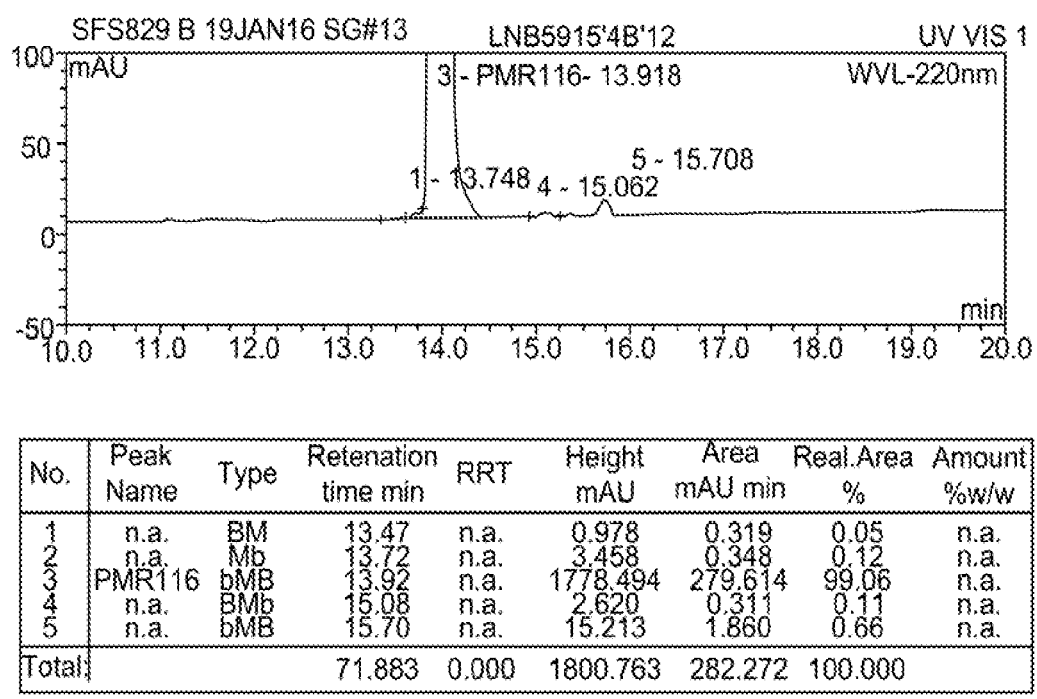
FIG. 76 depicts the High Performance Liquid Chromatography (HPLC) purity analysis of Form 1 after four (4) weeks at room temperature.
Figure 77:
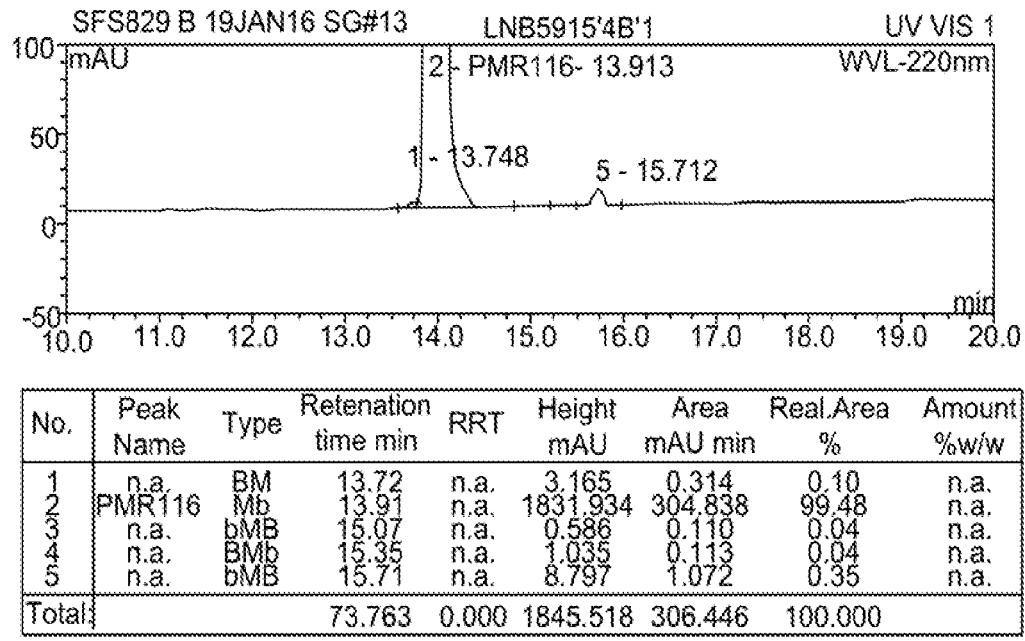
FIG. 77 depicts the High Performance Liquid Chromatography (HPLC) purity analysis of Form 1 after two (2) weeks at 40° C. and 75% relative humidity.
Figure 78:
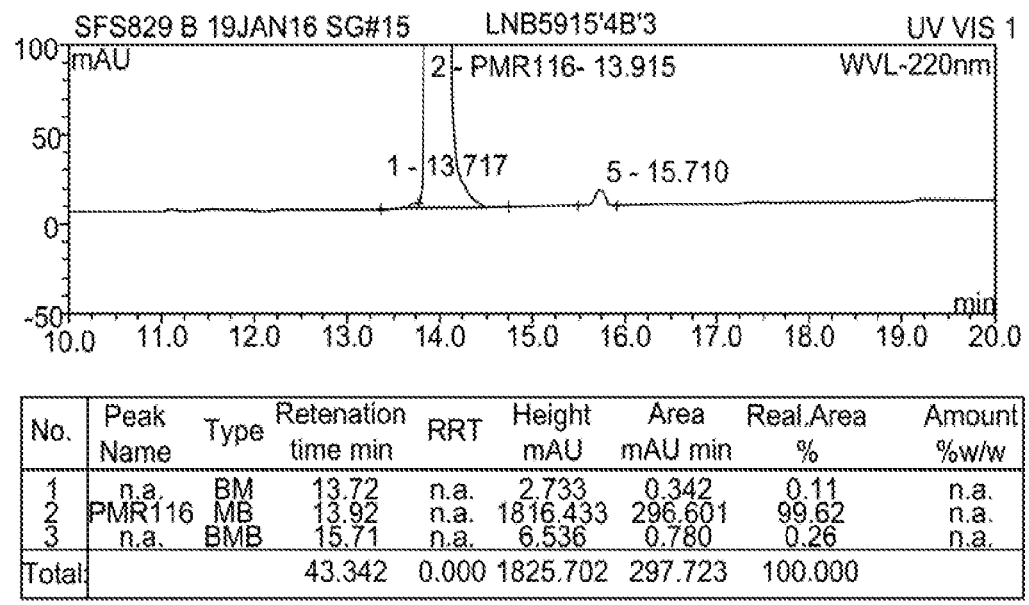
FIG. 78 depicts the High Performance Liquid Chromatography (HPLC) purity analysis of Form 1 after four (4) weeks at 40° C. and 75% relative humidity.
Figure 79:
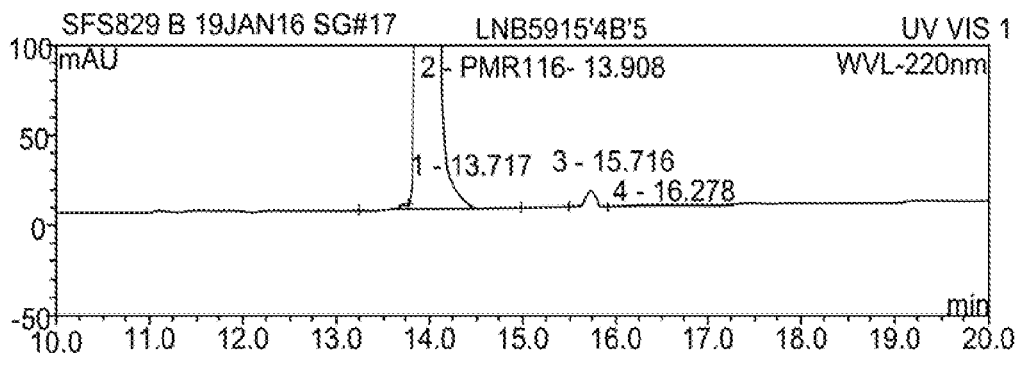
FIG. 79 depicts the High Performance Liquid Chromatography (HPLC) purity analysis of Form 1 after two (2) weeks at 50° C.
Figure 80:
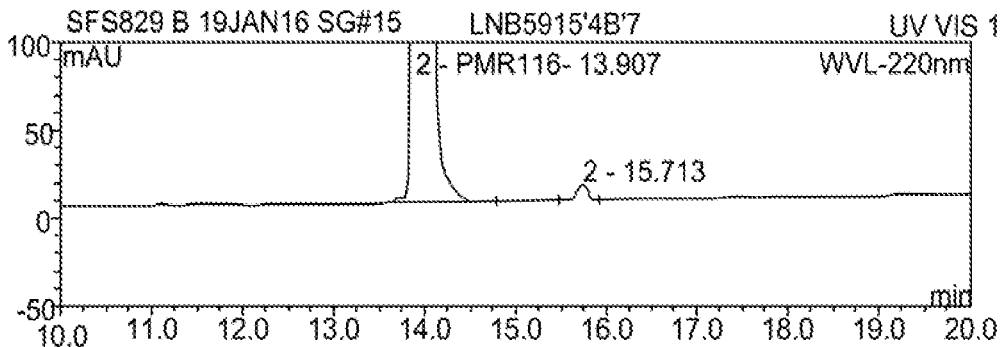
FIG. 80 depicts the High Performance Liquid Chromatography (HPLC) purity analysis of Form 1 after four (4) weeks at 50° C.

Specifically, FIG. 75 shows HPLC purity analysis of Form 1 after 2 weeks of storage at room temperature; FIG. 76 shows HPLC purity analysis of Form 1 after 4 weeks of storage at room temperature; FIG. 77 shows HPLC purity analysis of Form 1 after 2 weeks of storage at 40° C. and 75% relative humidity; FIG. 78 shows HPLC purity analysis of Form 1 after 4 weeks of storage at 40° C. and 75% relative humidity; FIG. 79 shows HPLC purity analysis of Form 1 after 2 weeks of storage at 50° C.; and FIG. 80 shows HPLC purity analysis of Form 1 after 4 weeks of storage at 50° C.

TABLE 5

HPLC Purities of Form 1 Post Stability Studies

| Sample | % Purity | |
| --- | --- | --- |
| | 2 weeks | 4 weeks |
| Room Temperature | 99.2 | 99.1 |
| 40° C./75% Relative Humidity | 99.3 | 99.6 |
| 50° C./Ambient % RH | 99.4 | 99.7 |

Crystalline Form 2 of N-Methyl-2-(4-Methyl-1,4-Diazepan-1-Yl)Benzo[4,5]Imidazo[1,2-A][1,8]Naphthyridine-6-Carbaxomide (Compound I)

Figure 9:
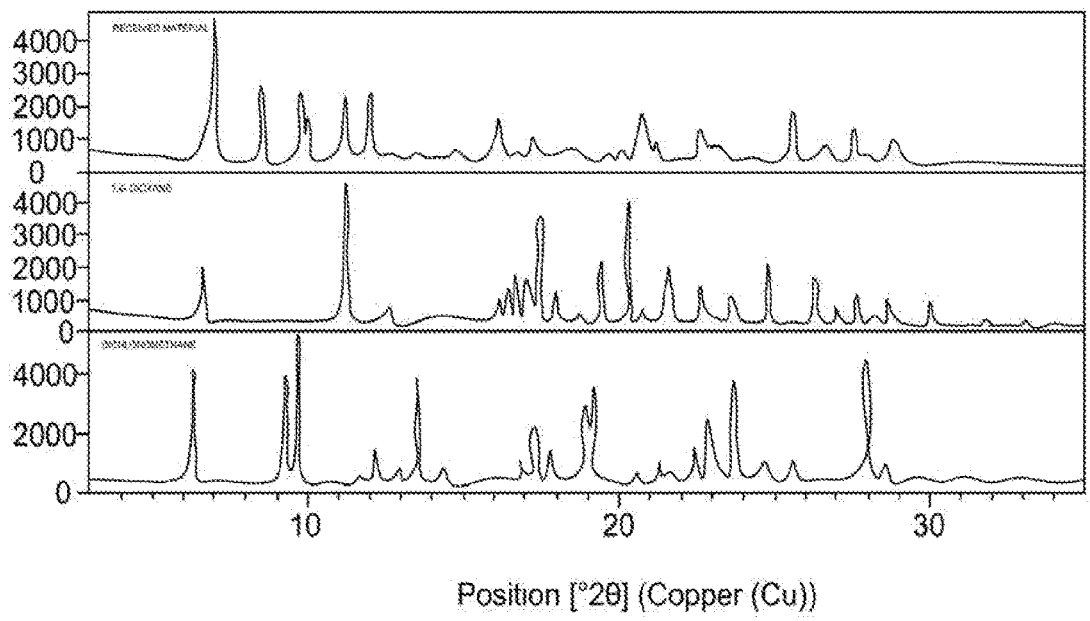
FIG. 9 depicts the powder X-ray diffraction pattern (PXRD) of N-methyl-2-(4-methyl-1,4-diazepan-1-yl)benzo[4,5]imidazo[1,2-a][1,8]naphthyridine-6-carbaxomide (Compound (I)) in multiphasic form (starting material); Form 2 as produced in the 1,4-dioxane slurry; and Form 3 as produced in the dichloromethane slurry.

The Form 2 of Compound (I) was made by preparing a mixture (e.g., slurry) of Compound (I) in 1,4-dioxane by adding 200 mg of Compound (I) to 2.4 mL of 1,4-dioxane. This slurry is then temperature cycled from 5° C. to 25° C. for a period of 72 hours. PXRD analysis of Form 2 is shown in FIG. 9.

Figure 25:
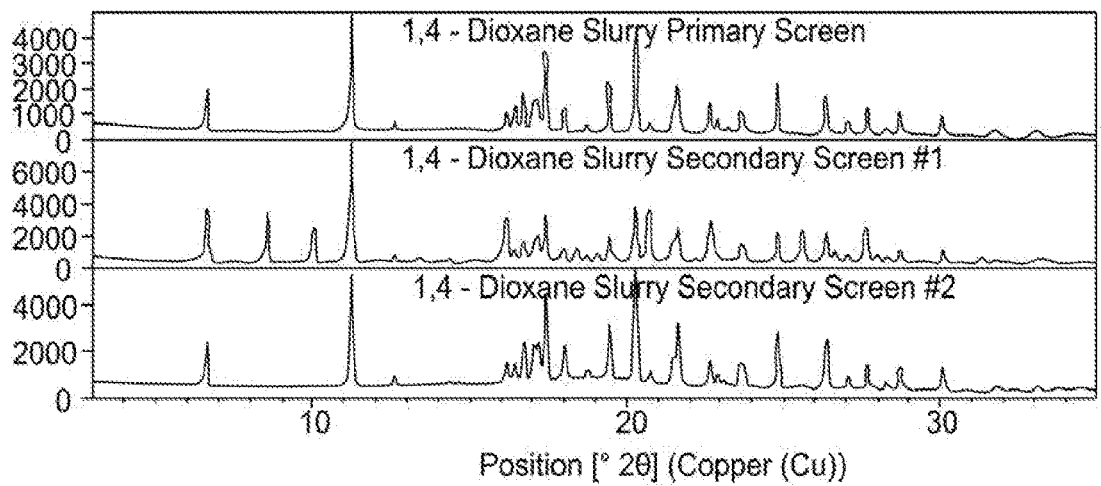
FIG. 25 depicts the powder X-ray diffraction pattern (PXRD) of Form 2 from the primary crystal form screen (top); the powder X-ray diffraction pattern (PXRD) of Form 2, 72 hours post slurrying (middle); and the powder X-ray diffraction pattern (PXRD) of Form 2, 144 hours post slurrying (bottom).

Form 2 was reproduced on a large scale from a 1,4-dioxane slurry. PXRD analysis shows Form 2 is not initially reproducible (FIG. 25, Secondary screen crystallization #1) after analysis 72 hours post slurrying However, after an additional 72 hours Form 2 is produced (See, FIG. 25, Secondary screen crystallization #2).

Figure 26:
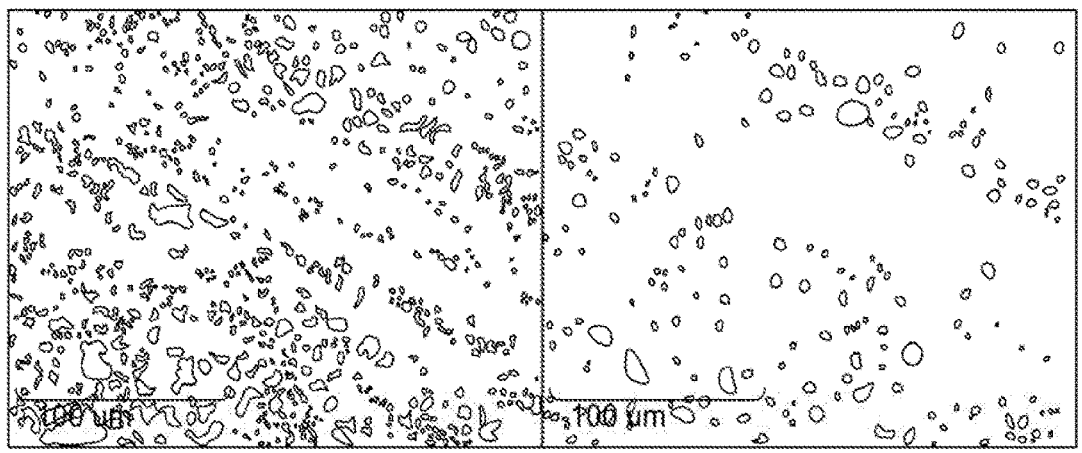
FIG. 26 depicts Polarized Light Microscopy (PLM) results of Form 2 pre-drying.
Figure 27:
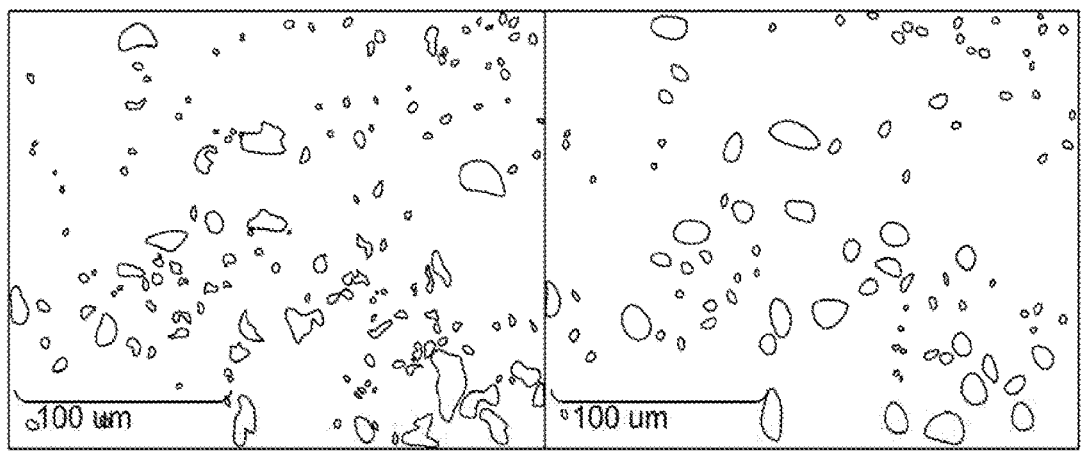
FIG. 27 depicts Polarized Light Microscopy (PLM) results of Form 2 post-drying.

PLM analysis illustrates that Form 2 consists of small birefringent particles of no defined morphology, both prior-to and post drying (See, FIG. 26 and FIG. 27).

Figure 28:
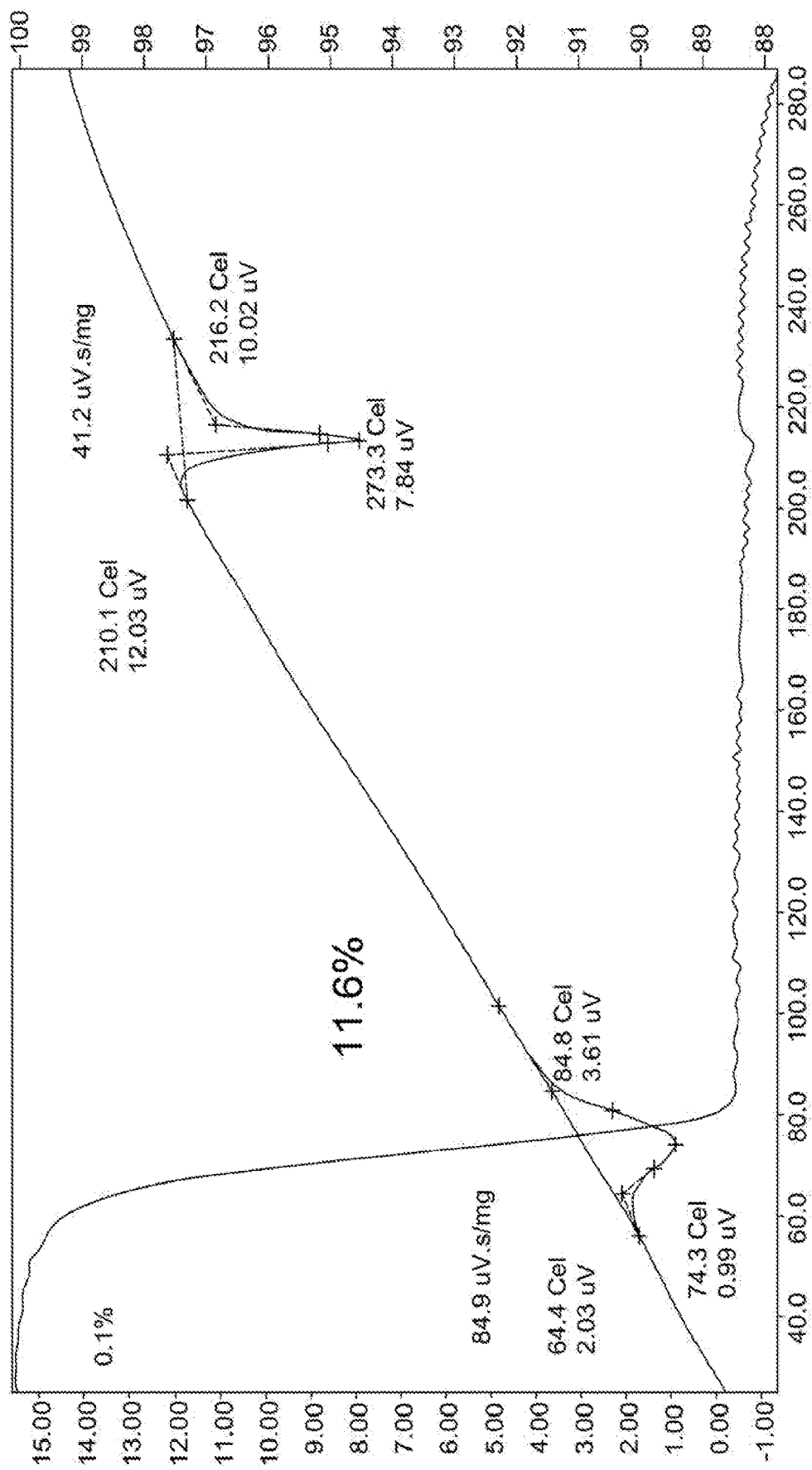
FIG. 28 depicts the Thermogravimetric Analysis (TGA) and Differential Thermal Analysis (DTA) of Form 2.

TG/DTA shows an initial mass loss of 0.1% until an endothermic event with onset of 64.4° C., and peak at 74.3° C. (See, FIG. 28). A mass loss of 11.6% was observed to be associated with this event, likely corresponding to solvent loss.

Figure 29:
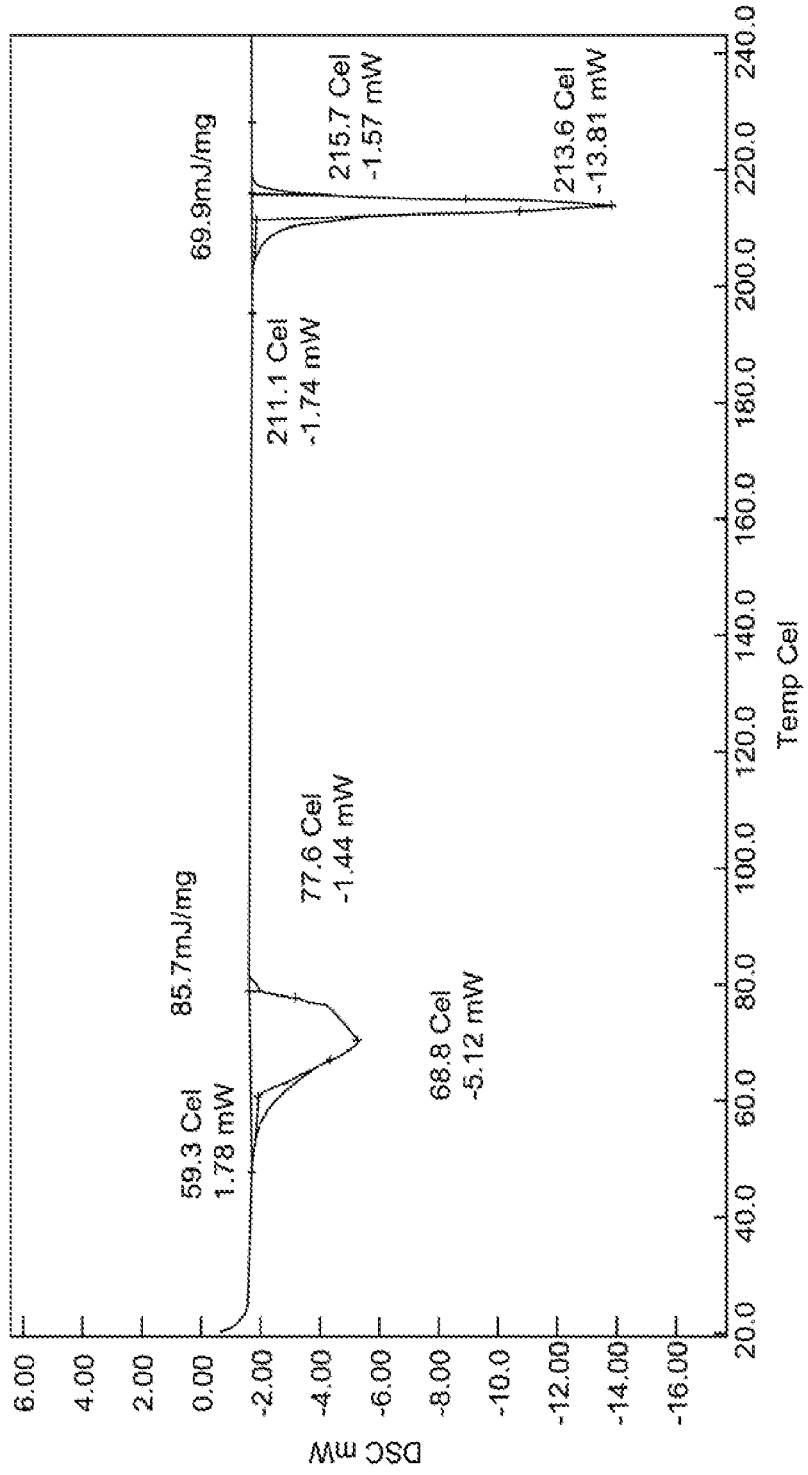
FIG. 29 depicts the Differential Scanning Calorimetry (DSC) thermogram ($1^{st}$ heating cycle) of Form 2.

A second endotherm was then observed with onset at 210.1° C., and peak at 213.3° C., indicative of the melt of Compound (I). DSC analysis of the first heating cycle illustrated an initial exothermic event with onset of 59.3° C., and peak at 68.8° C., when compared to TGA trace this is anticipated to correspond to the de-solvation of Form 2 (See, FIG. 29).

A second exothermic event was observed with onset at 211.1° C., and peak at 213.6° C.

Figure 30:
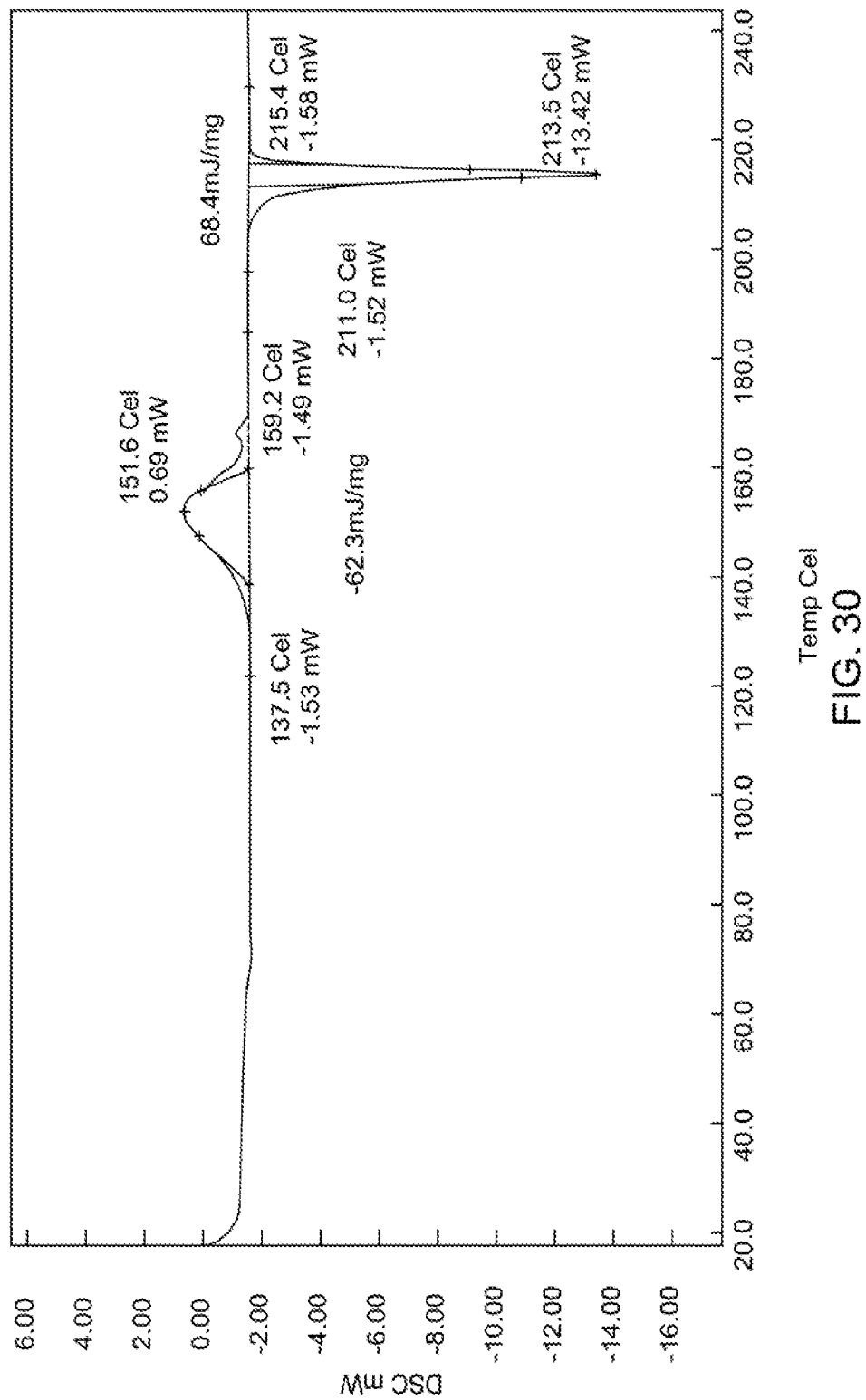
FIG. 30 depicts the Differential Scanning Calorimetry (DSC) thermogram ($2^{nd}$ heating cycle) of Form 2.

On second heating cycle, an exothermic event was observed with onset at 138.5° C., and peak at 151.6° C., likely associated with the re-crystallization of Compound (I) (See, FIG. 30). This lead into an endothermic event with onset of 211° C. and peak at 213° C., attributed to the melt of Compound (I).

Figure 31:
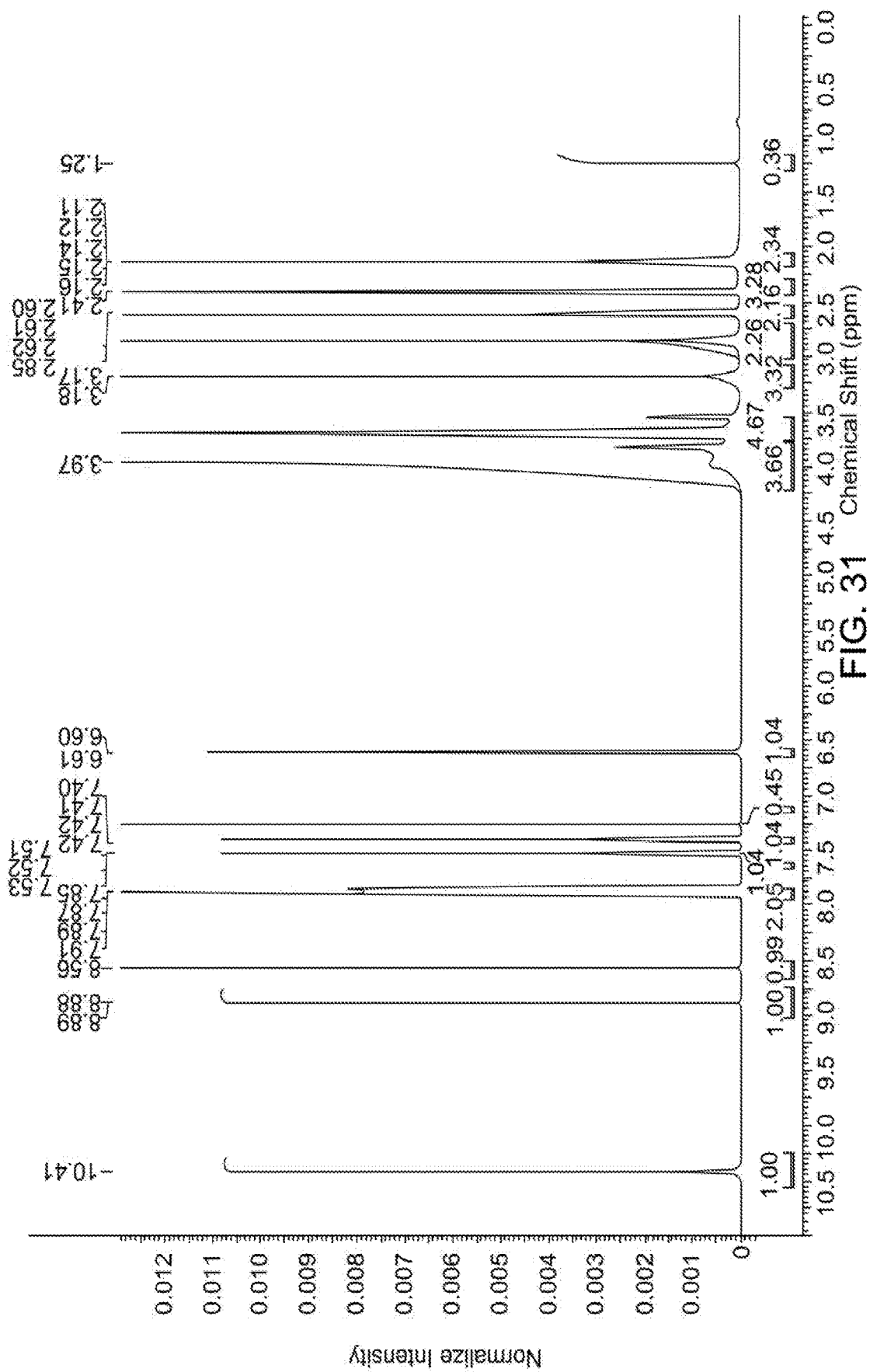
FIG. 31 depicts the $^1$H NMR analysis (CDCl$_3$, 500 MHz) of Form 2.

¹H NMR analysis confirmed the structural integrity of Compound (I) in Form 2 (See, FIG. 31). The presence of 1,4-dioxane may be seen at 3.64 ppm.

Figure 52:
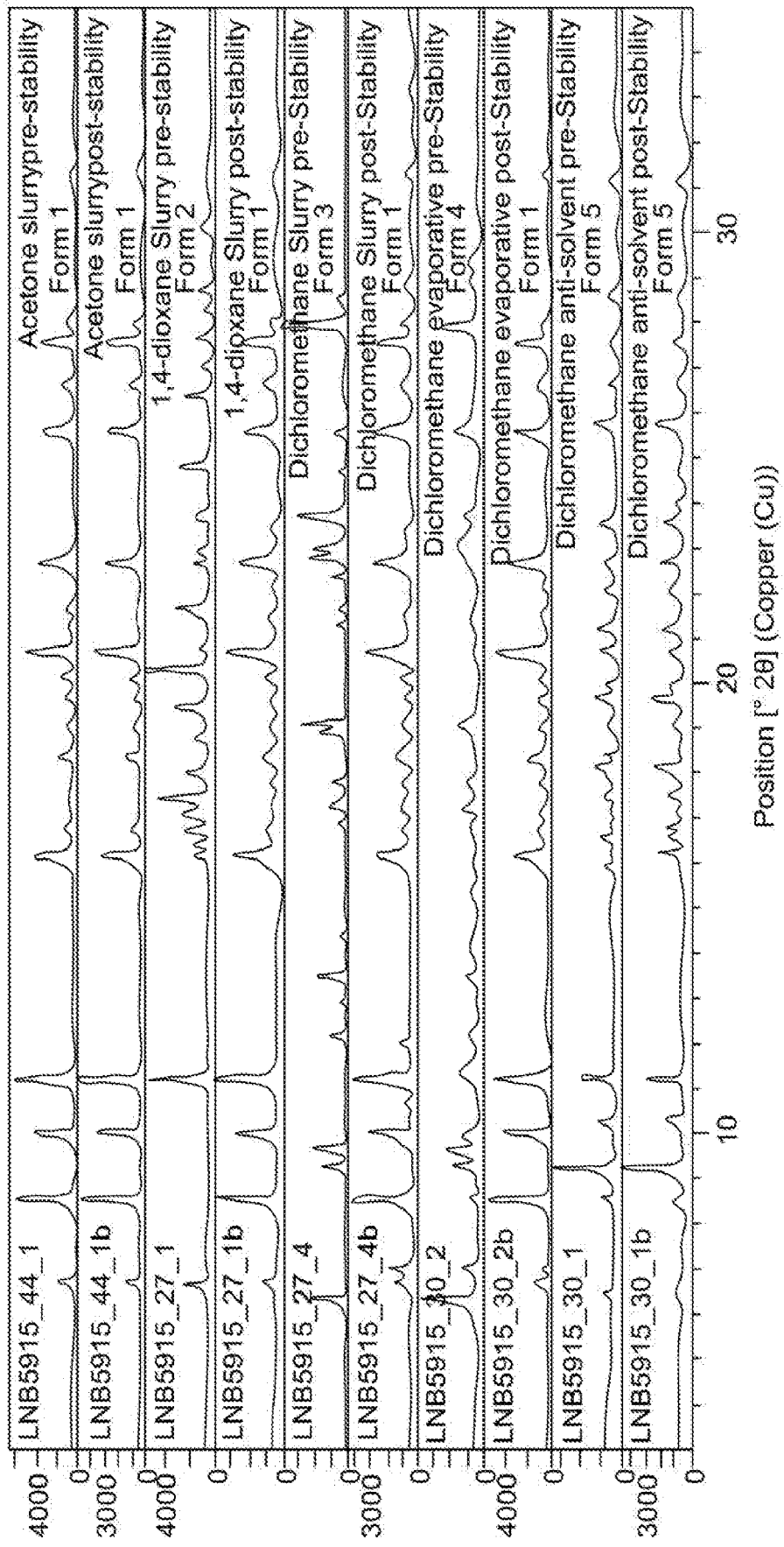
FIG. 52 depicts the powder X-ray diffraction pattern (PXRD) of Forms 1-5 pre and post stability testing.

Form 2 is stable and maintains its form after 7-day storage under ambient conditions (closed vial). After 7-day storage under 40° C./75% RH (closed vial), Form 2 transitions to Form 1. Results of a post-storage PXRD analysis of Form 2 are shown in FIG. 52.

Crystalline Form 3 of N-Methyl-2-(4-Methyl-1,4-Diazepan-1-Yl)Benzo[4,5]Imidazo[1,2-A][1,8]Naphthyridine-6-Carbaxomide (Compound I)

The Form 3 of Compound (I) was made by preparing a mixture (e.g., slurry) of Compound (I) in dichloromethane by adding 200 mg of Compound (I) to 400 microliters of dichloromethane. The resulting slurry was then temperature cycled from about 5° C. to 25° C. for a period of about 72 hours.

Figure 12:
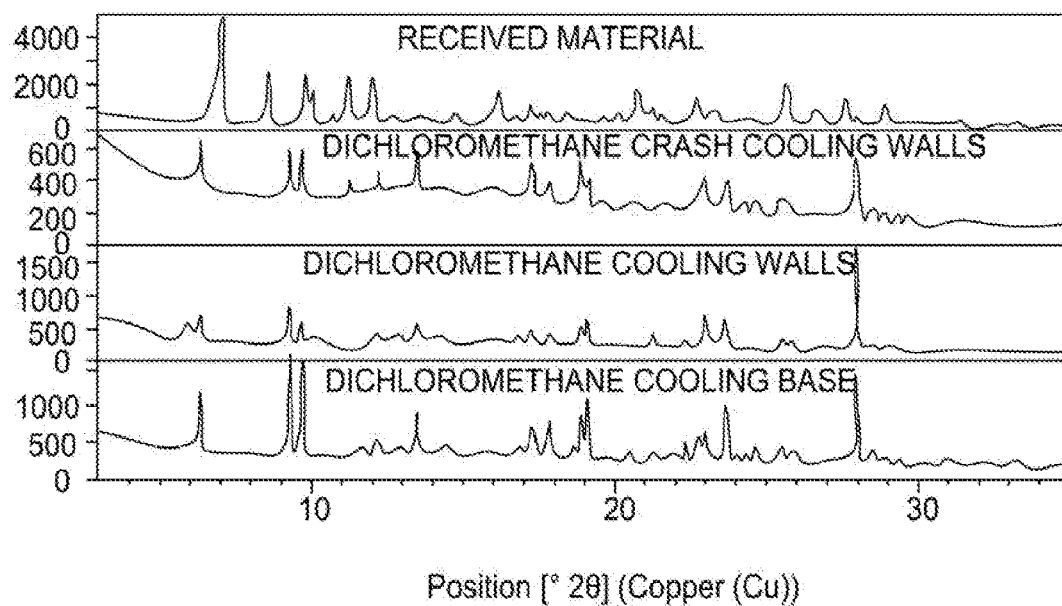
FIG. 12 depicts the powder X-ray diffraction pattern (PXRD) of N-methyl-2-(4-methyl-1,4-diazepan-1-yl)benzo[4,5]imidazo[1,2-a][1,8]naphthyridine-6-carbaxomide (Compound (I)) in multiphasic form (starting material); and Form 3 from the dichloromethane cooling crystallizations, which had evaporated.
Figure 82:
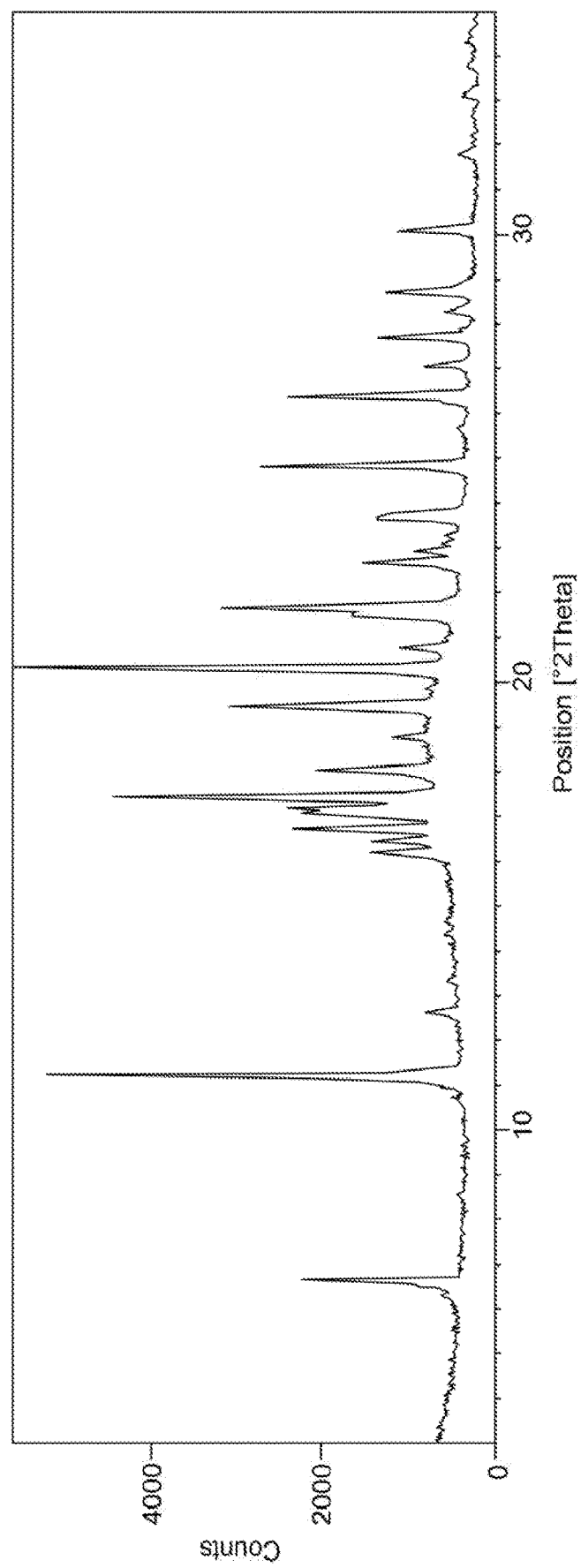
FIG. 82 depicts the powder X-ray diffraction pattern (PXRD) of Form 2.
Figure 83:
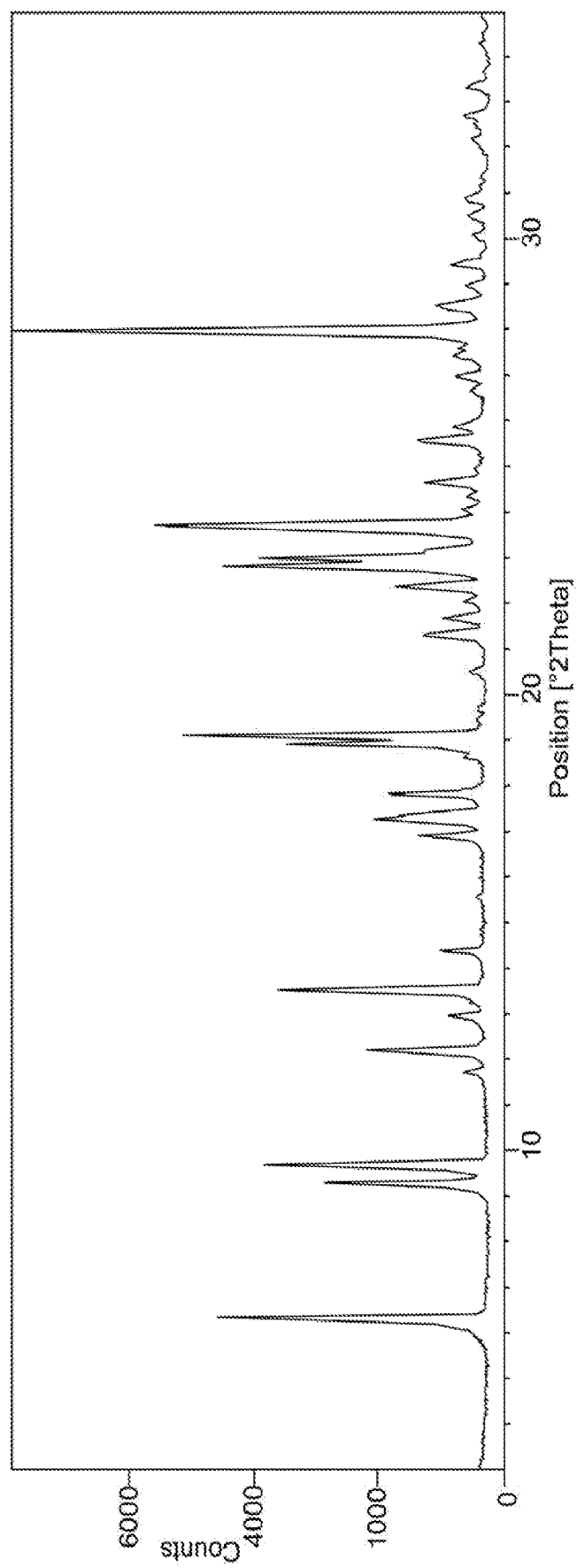
FIG. 83 depicts the powder X-ray diffraction pattern (PXRD) of Form 3.
Figure 84:
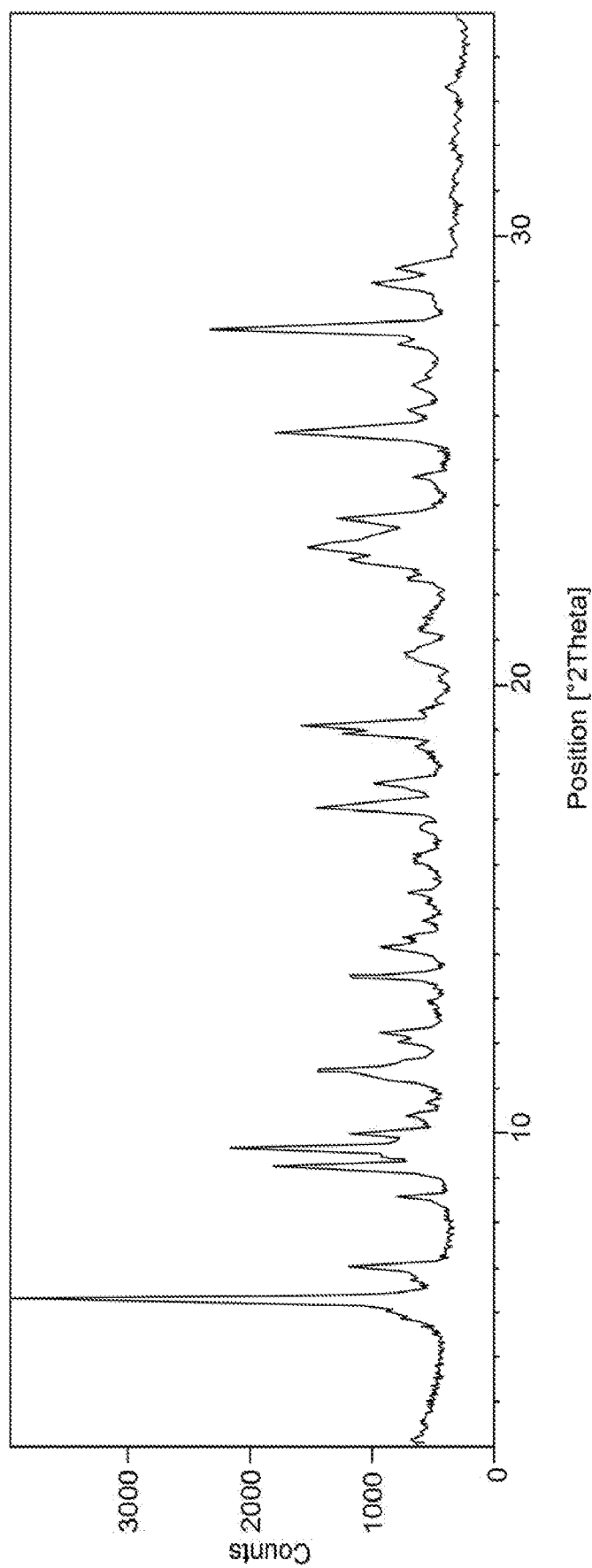
FIG. 84 depicts the powder X-ray diffraction pattern (PXRD) of Form 4.
Figure 85:
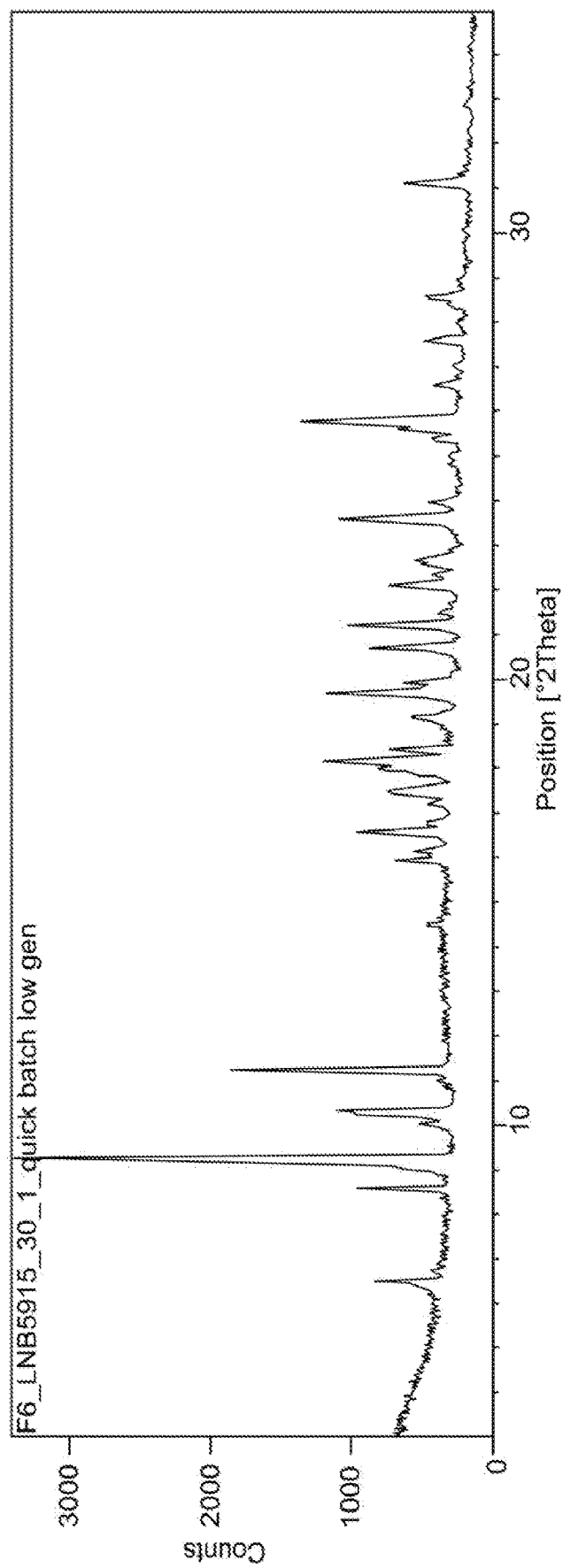
FIG. 85 depicts the powder X-ray diffraction pattern (PXRD) of Form 5.

PXRD analysis of Form 3 is shown in FIG. 82. FIG. 12 shows PXRD analysis of dichloromethane cooling crystallizations which had evaporated leaving Form 3.

Figure 13:
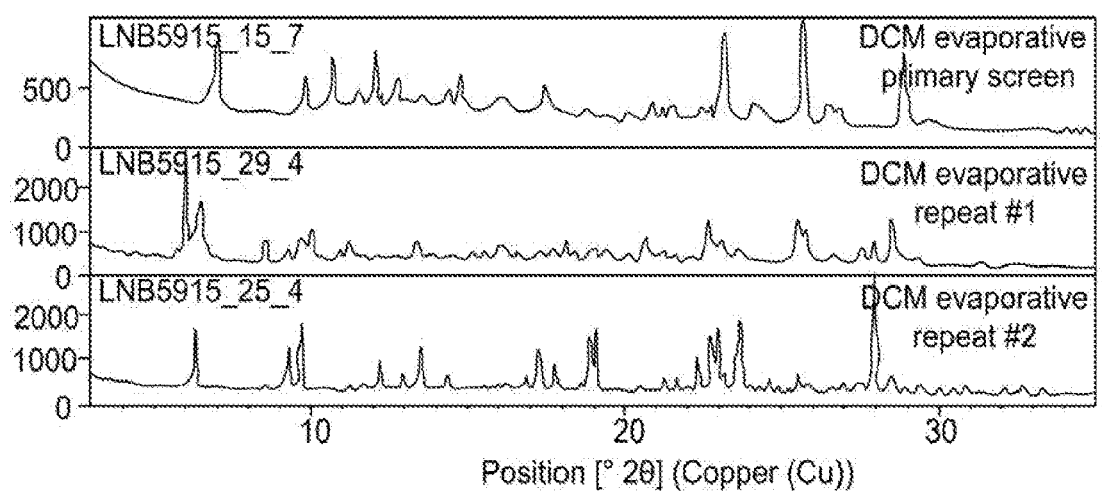
FIG. 13 depicts the powder X-ray diffraction pattern (PXRD) of N-methyl-2-(4-methyl-1,4-diazepan-1-yl)benzo[4,5]imidazo[1,2-a][1,8]naphthyridine-6-carbaxomide (Compound (I)) in multiphasic form after repeat dichloromethane evaporative crystallization experiments.

Initially, the production of Form 3 did not appear reproducible (See, FIG. 13). As illustrated in FIG. 13, Different forms were produced on subsequent repeats. A sufficient quantity of Form 3 was prepared in a primary crystal form screen to allow for TG/DTA and DSC analysis to be conducted prior to the commencement of a secondary crystal form screen.

Figure 14:
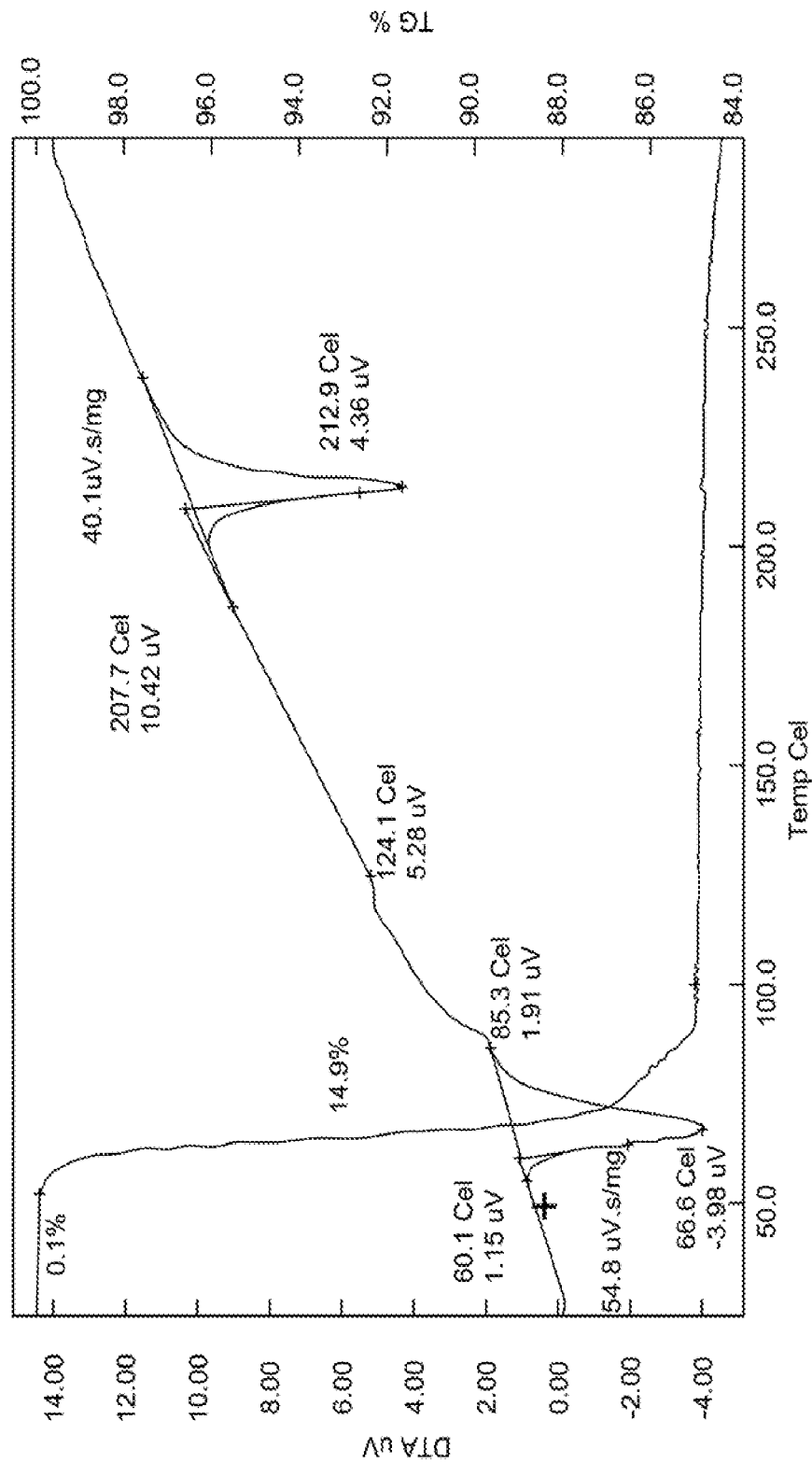
FIG. 14 depicts the Thermogravimetric Analysis (TGA) and Differential Thermal Analysis (DTA) of Form 3 from the primary screen.

TG/DTA shows an initial mass loss of 0.1% prior to an endotherm (DTA trace) with onset of 60.1° C., and a peak at 66.6° C., which coincides with a weight loss of 14.9% thereby indicative of desolvation of material (See, FIG. 14). A shallow exothermic event occurs between 85.3° C. and 124.1° C. followed by an endothermic event with onset of 207.7° C., and peak at 212.9° C. This is anticipated to be associated with the melt of the crystallized Compound (I).

Figure 15:
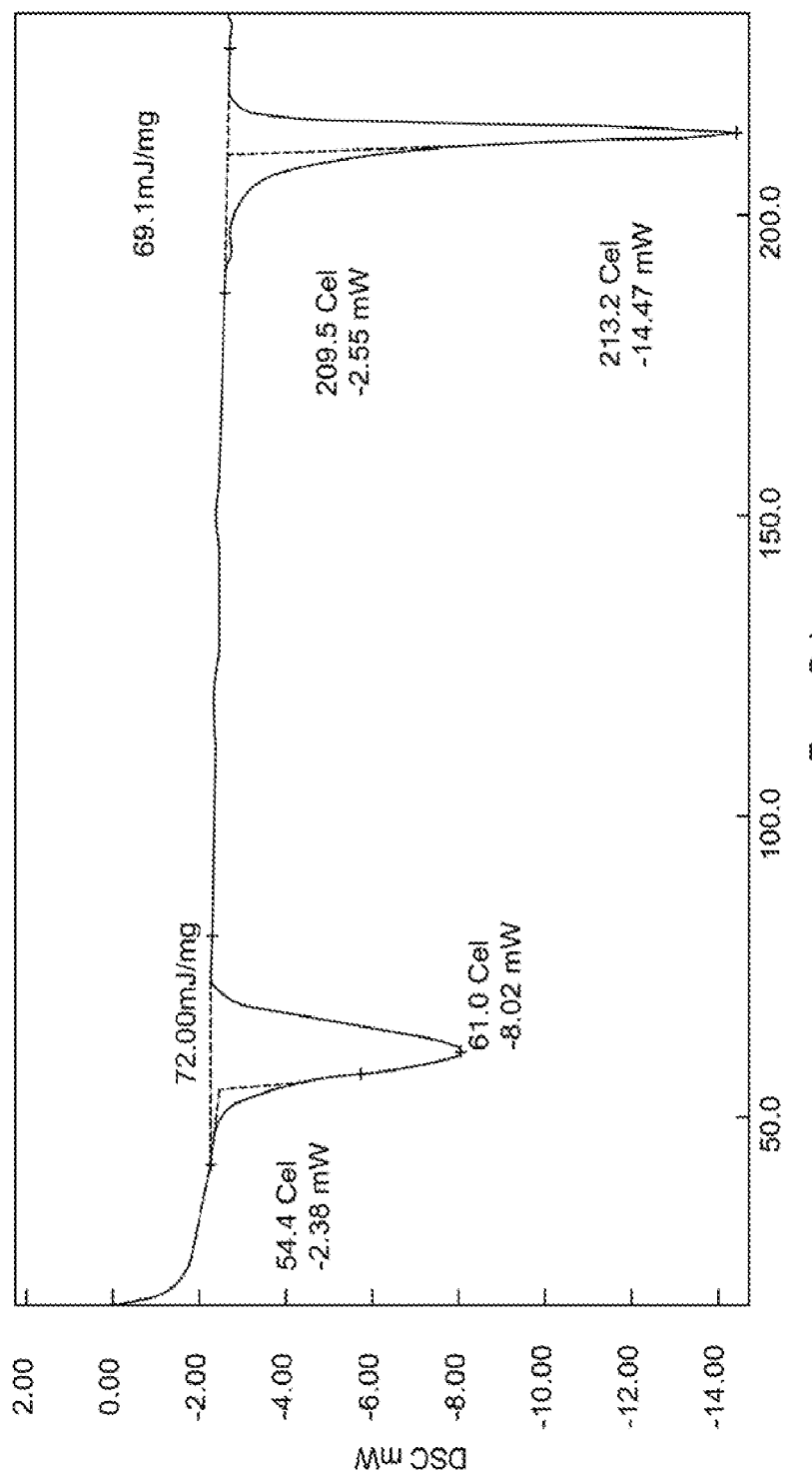
FIG. 15 depicts the Differential Scanning Calorimetry (DSC) thermogram ($1^{st}$ heating cycle) of Form 3 from the primary crystal form screen.

DSC analysis of first heating cycle shows a broad endothermic event with an onset of 54.4° C. and a peak at 61° C. (See, FIG. 15).

Figure 16:
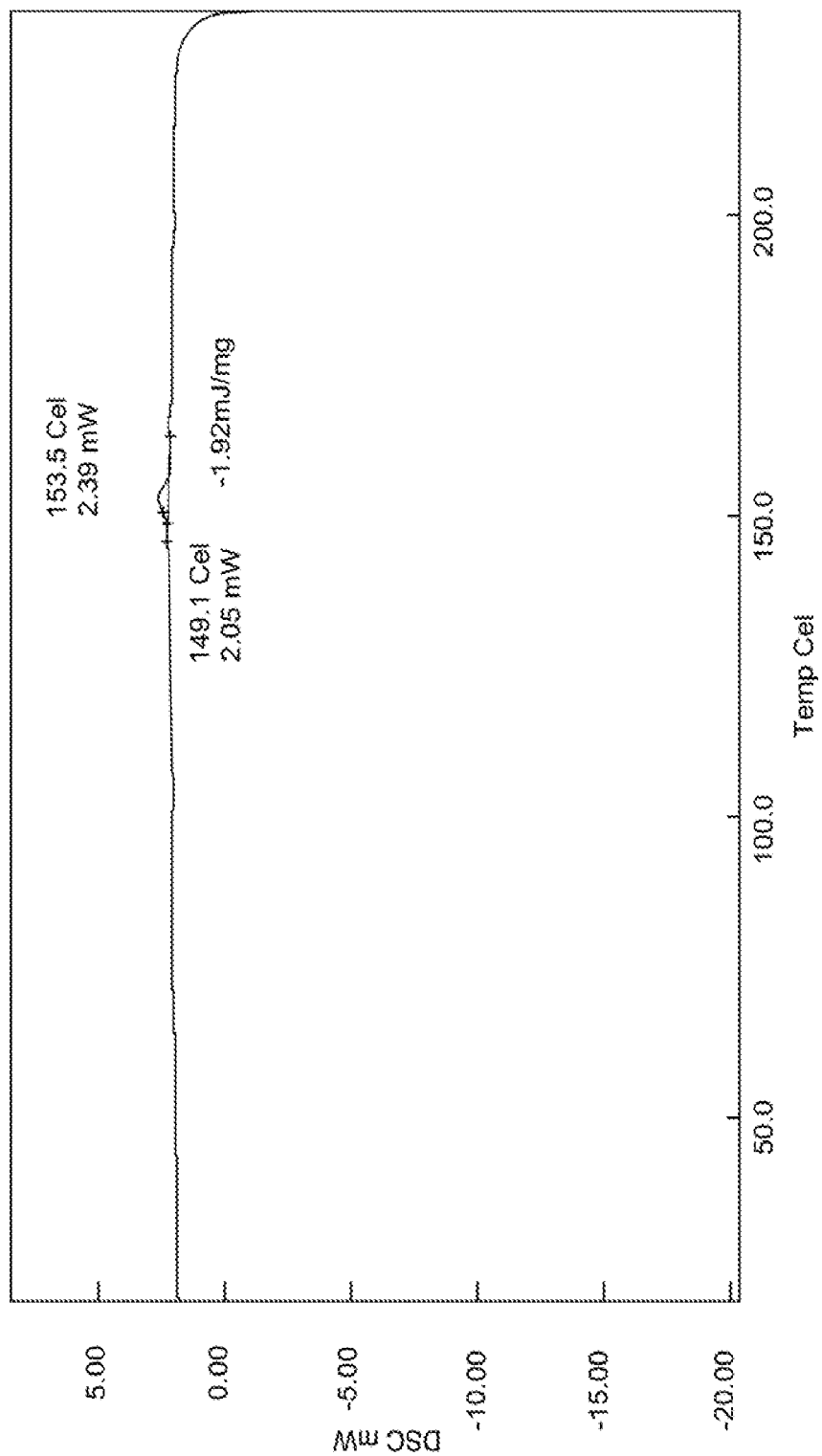
FIG. 16 depicts the Differential Scanning Calorimetry (DSC) thermogram (cooling cycle) of Form 3 from the primary crystal form screen.

A second endothermic event follows beginning at 209.5° C. reaching a peak at 213.2° C. On the cooling cycle a small exotherm is observed with onset at 149.1° C., and peak at 153.5° C., potentially due to recrystallization of Compound (I) (See, FIG. 16).

Figure 17:
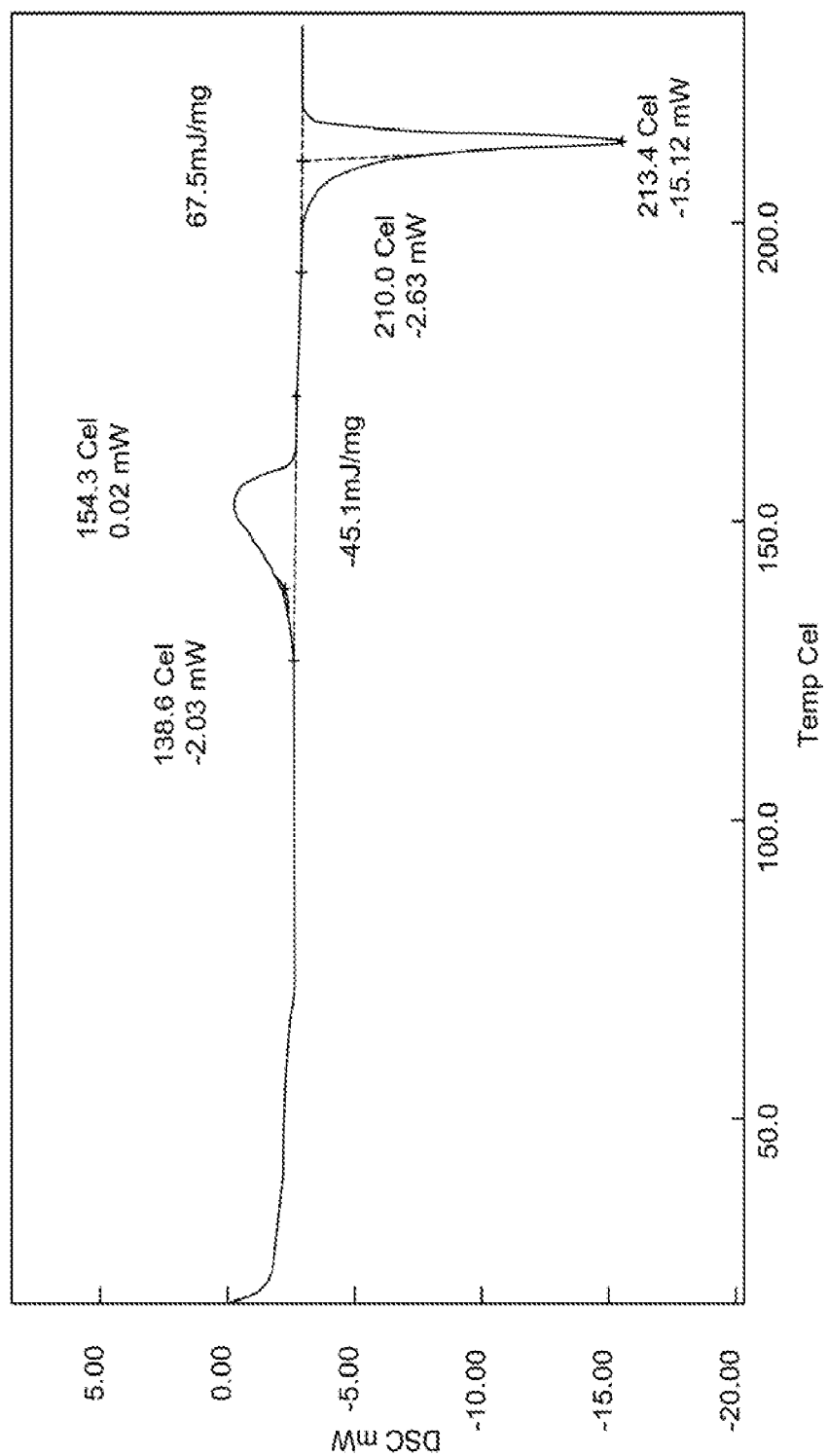
FIG. 17 depicts the Differential Scanning Calorimetry (DSC) thermogram ($2^{nd}$ heating cycle) of Form 3 from the primary crystal form screen.

The second heating cycle exhibited an exothermic event, with onset of 138.6° C. and a peak at 154.3° C. This leads into a second endothermic event with onset of 210° C. and a peak at 213.4° C., anticipated to correspond to the melting of Form 3. FIG. 17 shows DSC analysis of a second heating cycle of Form 3 material from a primary crystal form screen.

Figure 32:
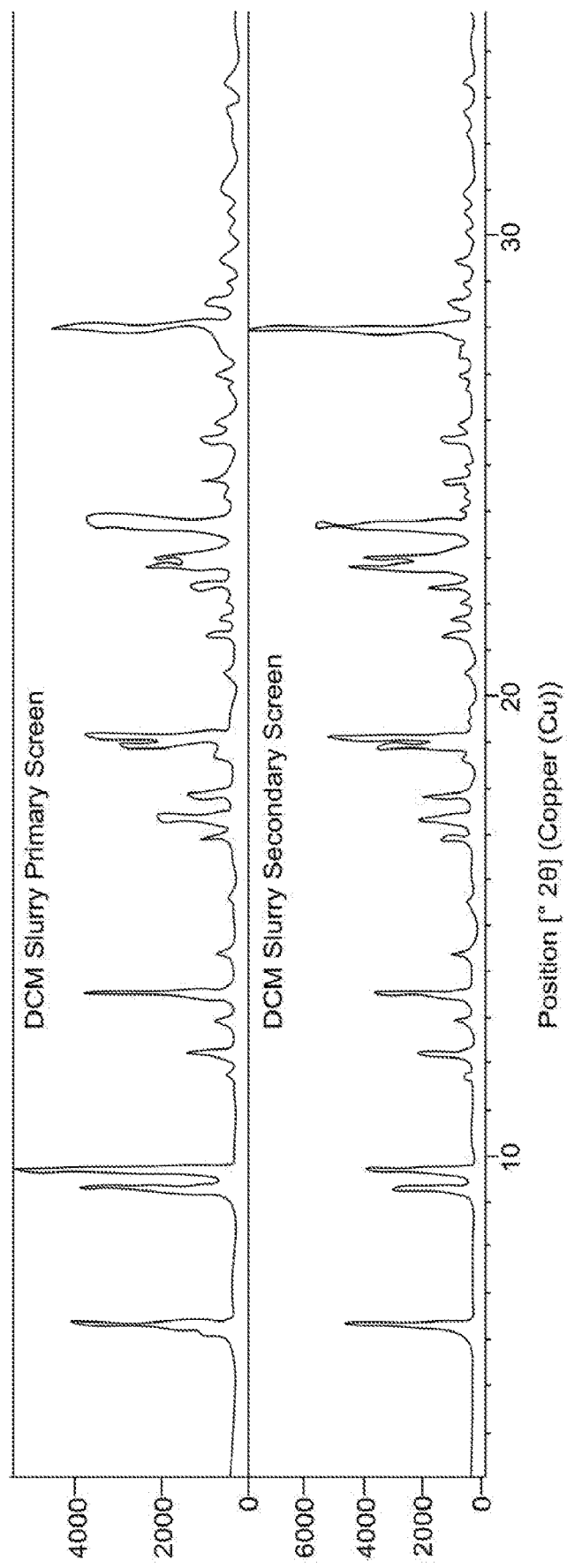
FIG. 32 depicts the powder X-ray diffraction pattern (PXRD) of Form 3 produced from the DCM slurry in the primary screen (top); and the powder X-ray diffraction pattern (PXRD) of Form 3 produced from the DCM slurry in the secondary screen (bottom).

Form 3 was produced on a large scale from a dichloromethane slurry. PXRD analysis shows the clean formation of Form 3 is reproducible (See, FIG. 32).

Figure 33:
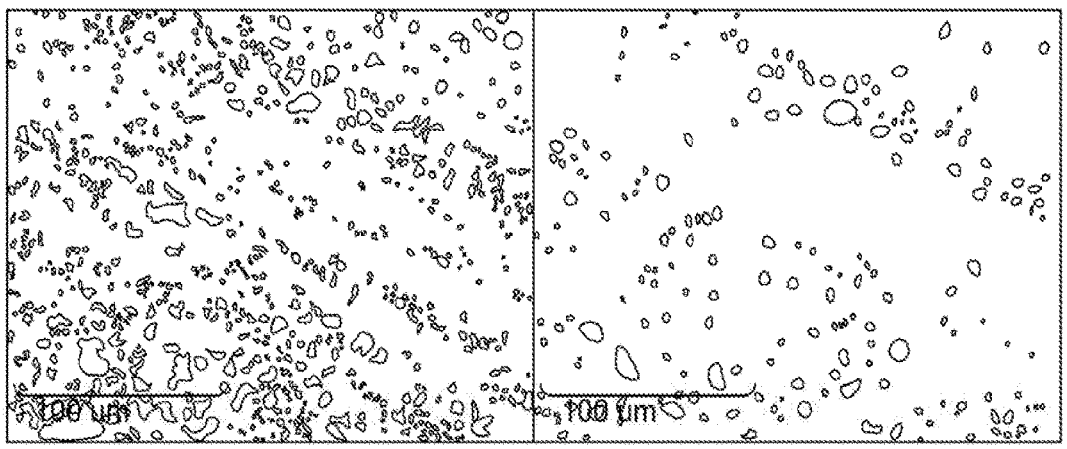
FIG. 33 depicts Polarized Light Microscopy (PLM) results of Form 3 pre-drying.
Figure 34:
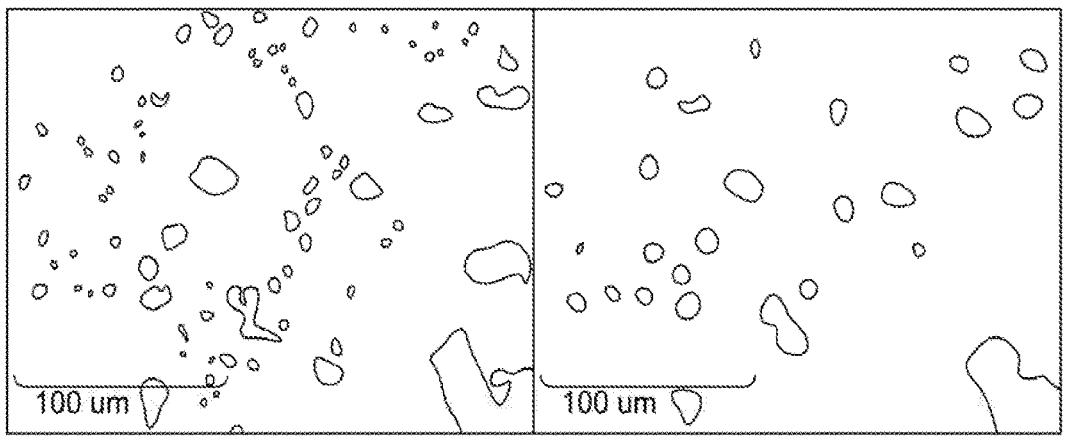
FIG. 34 depicts Polarized Light Microscopy (PLM) results of Form 3 post-drying.
Figure 35:
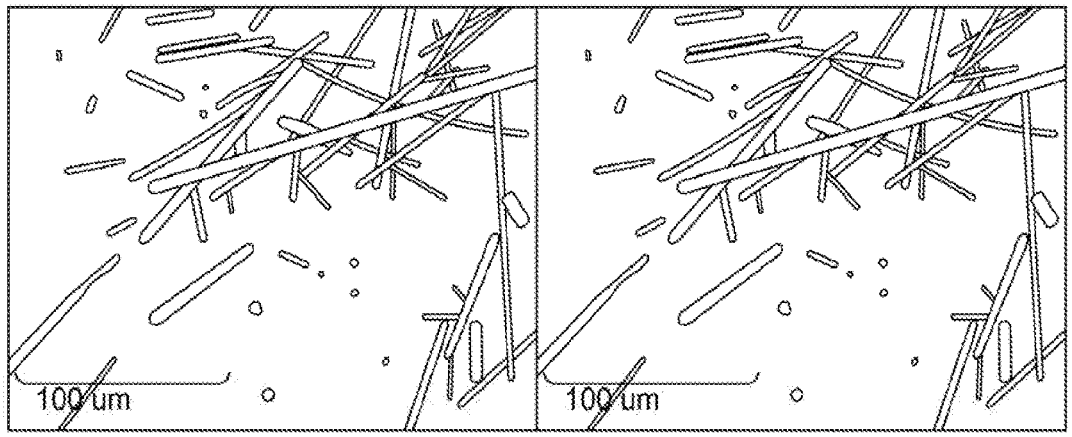
FIG. 35 depicts Polarized Light Microscopy (PLM) results of Form 3 post-drying.

PLM analysis shows Form 3 to consist of small birefringent particles pre-drying, and to consist of a mixture of particles of no defined morphology along with large rod-shaped particles post-drying (See, FIG. 33, FIG. 34 and FIG. 35).

Figure 36:
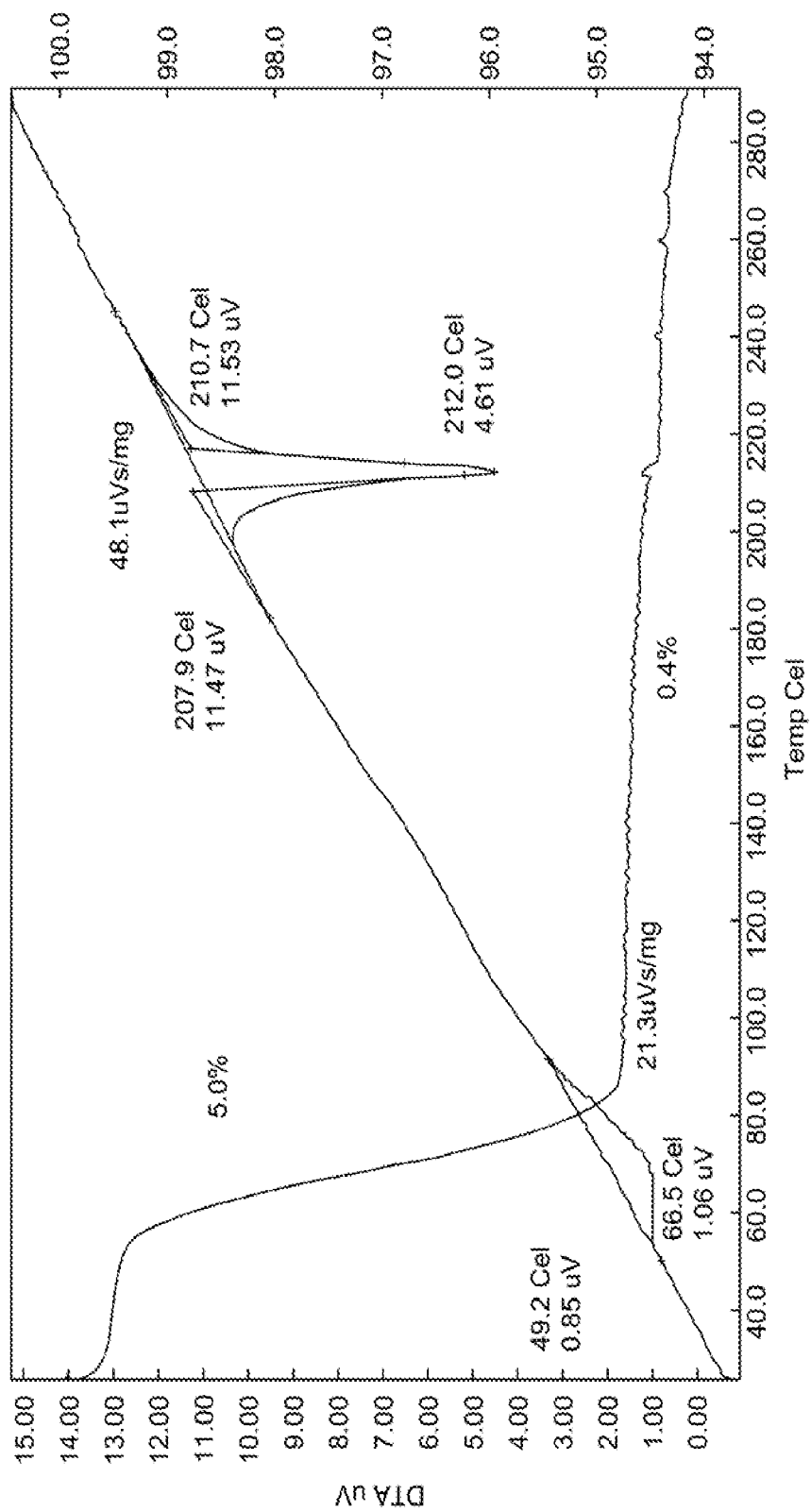
FIG. 36 is a TG/DTA thermogram of Form 3.

TG/DTA shows an initial mass loss of ca. 0.5% up to the onset of an endothermic event with onset of 49.2° C., and peak at 68.5° C. (See, FIG. 36). A further mass loss of ca. 4.5% is observed to be associated with this event, likely corresponding to solvent loss. A second endothermic event is observed with an onset of 207.7° C., and peak at 212° C., indicative of the melt of Compound (I).

Figure 37:
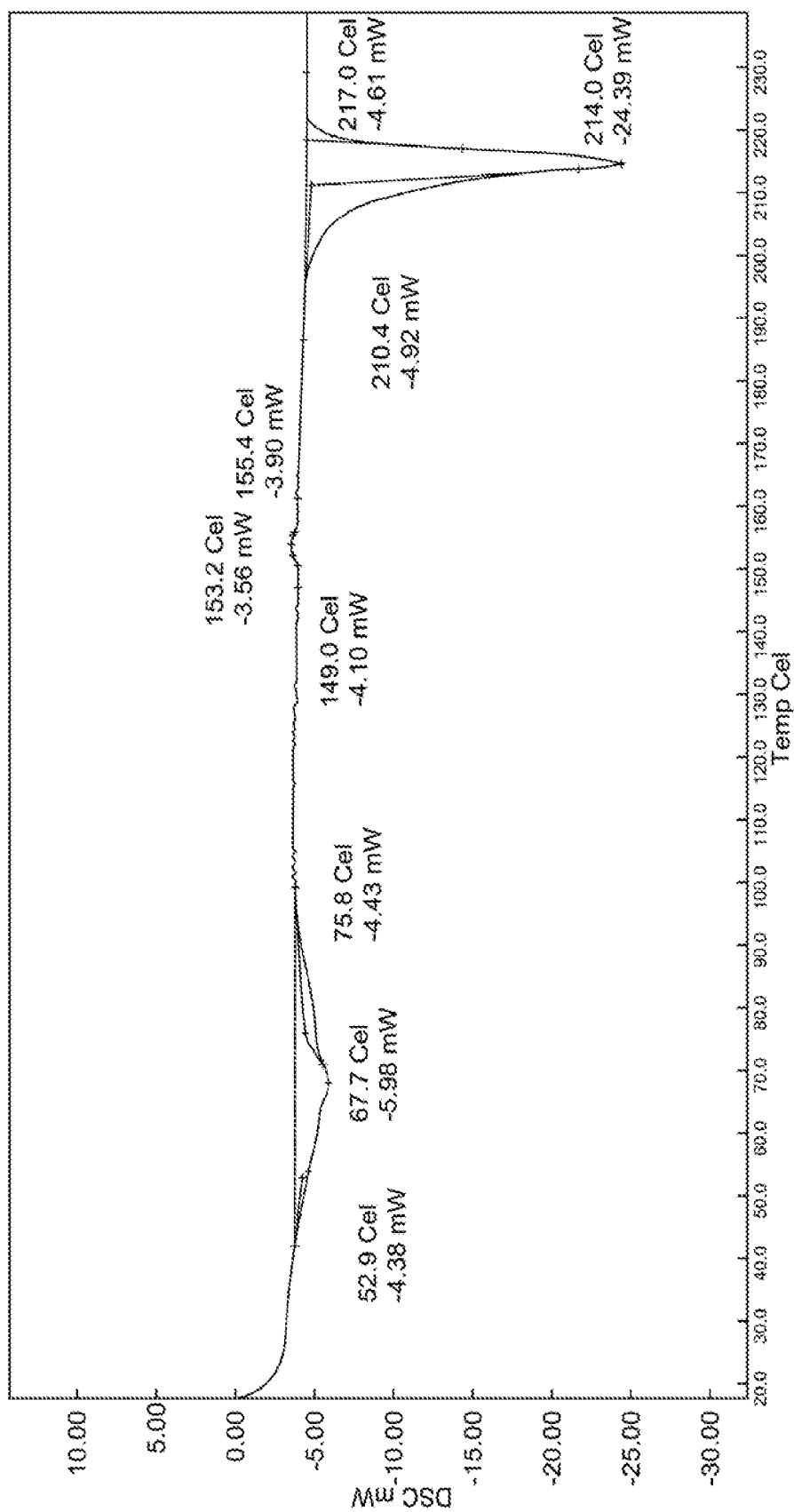
FIG. 37 depicts the Differential Scanning Calorimetry (DSC) thermogram (1$^{st}$ heating cycle) of Form 3.

DSC analysis of first heating cycle, shows an initial broad endothermic event with onset of 52.9° C., and peak at 67.7° C., when compared to TGA trace this is predicted to correspond to desolvation of Form 3 (See, FIG. 37). A small exothermic event with onset 149.6° C., and peak at 153.2° C. A final endothermic event due to a melt has an onset of 210.4° C., and peak at 214.0° C.

Figure 38:
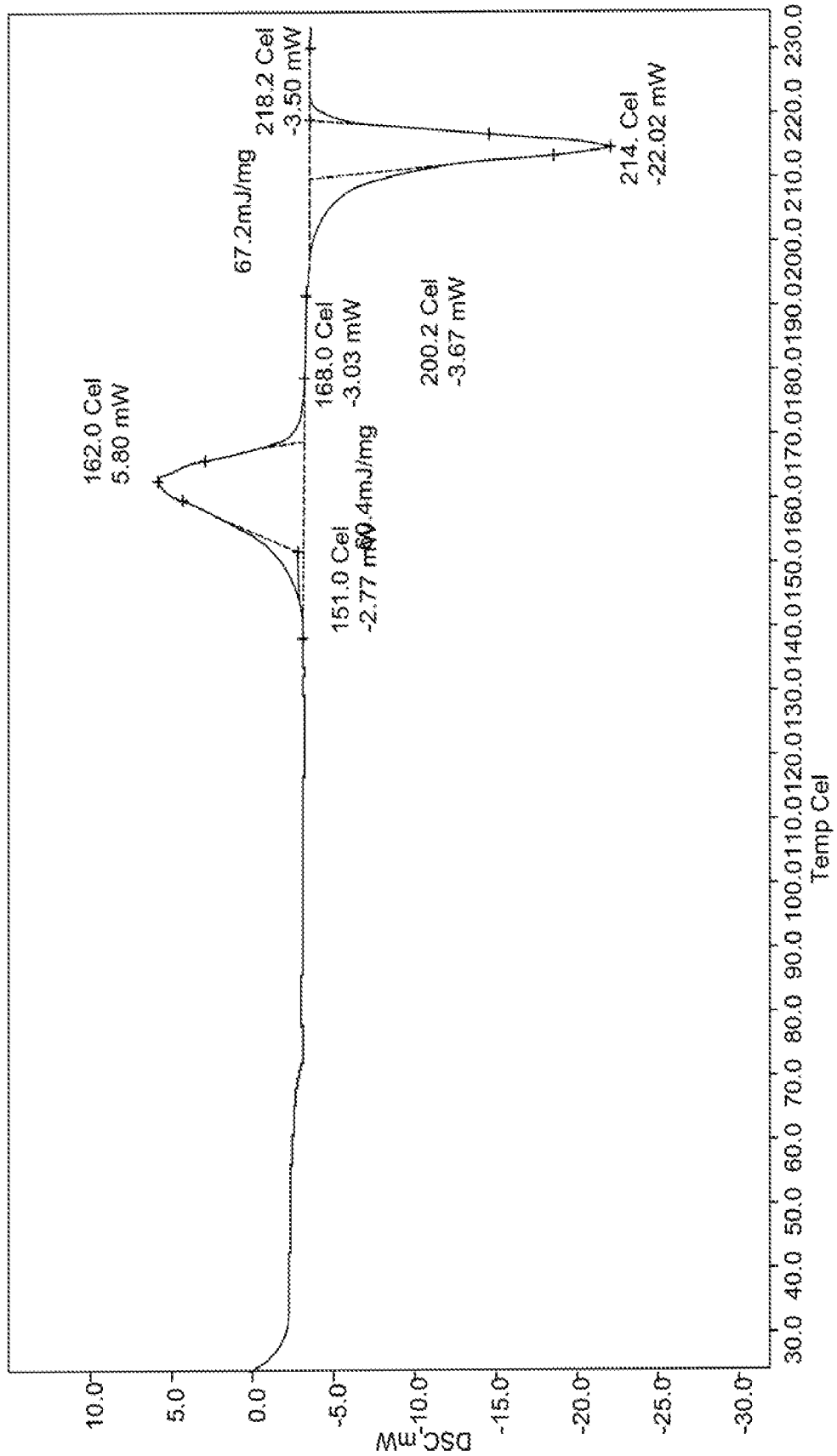
FIG. 38 depicts the Differential Scanning Calorimetry (DSC) thermogram (2$^{nd}$ heating cycle) of Form 3.

On second heating cycle, an exothermic event was observed with onset of 151° C., and peak at 162° C., likely associated with the re-crystallization of Form 3 (See, FIG. 38). This leads into an endothermic event with onset of 209.2° C. and a peak at 214° C., indicative of a melt of the crystallized Form 3.

Figure 39:
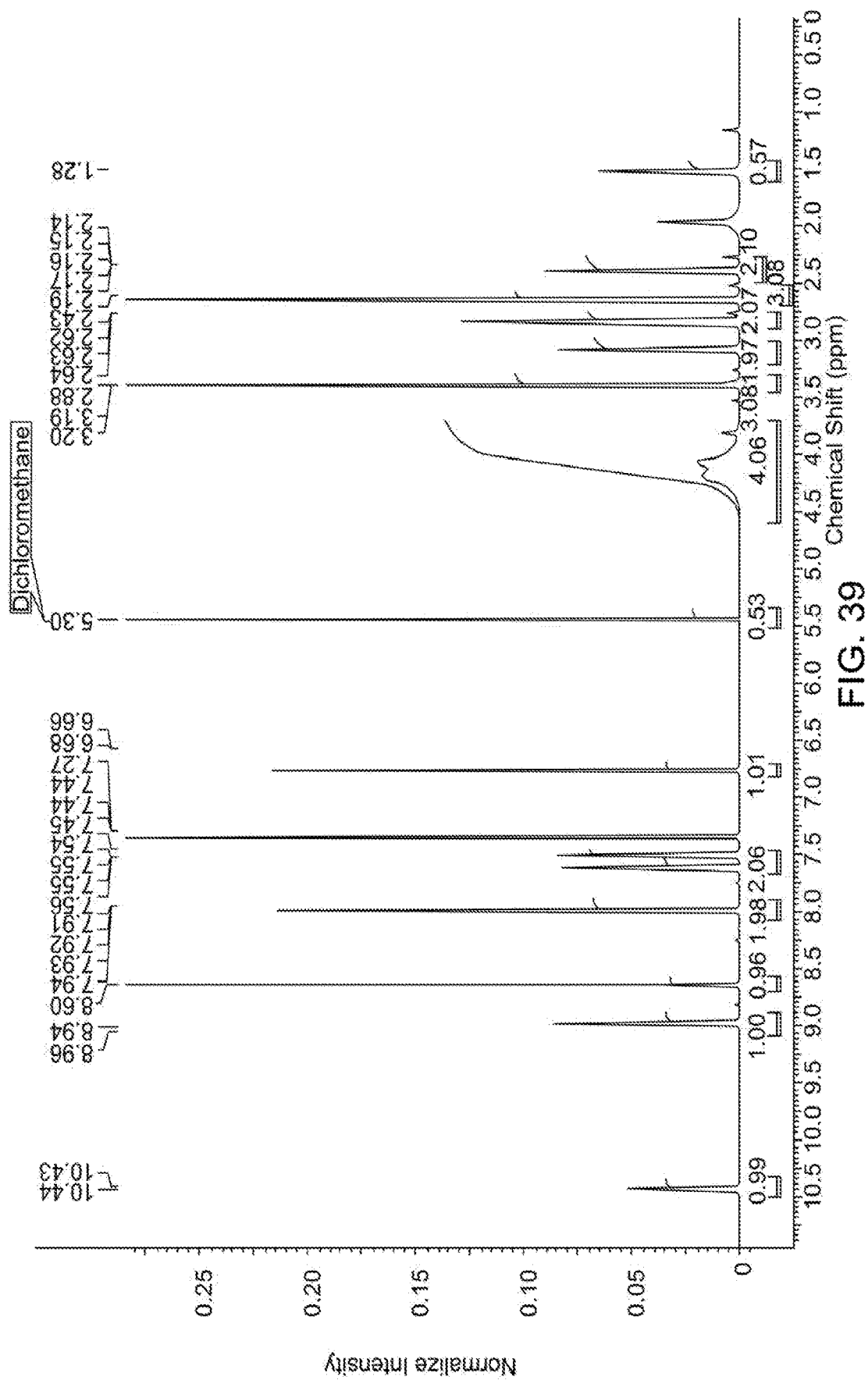
FIG. 39 depicts the $^1$H NMR analysis (CDCl$_3$, 500 MHz) of Form 3.

¹H NMR analysis shows the structural integrity of Compound (I) in Form 3 (See, FIG. 39). The presence of dichloromethane may be seen at 5.30 ppm.

Form 3 is stable and maintains its form after 7-day storage under ambient conditions (closed vial). After 7-day storage under 40° C./75% RH (closed vial), Form 3 transitions to Form 1. FIG. 52 provides the results of a post-storage PXRD analysis of Form 3.

Crystalline Form 4 of N-Methyl-2-(4-Methyl-1,4-Diazepan-1-Yl)Benzo[4,5]Imidazo[1,2-A][1,8]Naphthyridine-6-Carbaxomide (Compound I)

Figure 10:
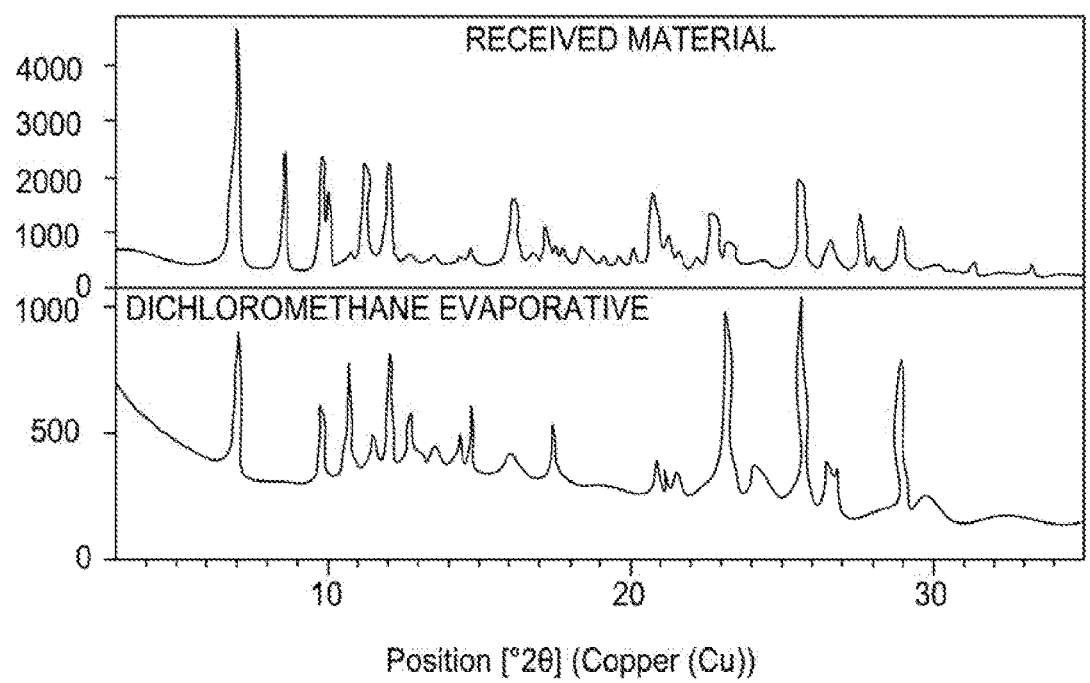
FIG. 10 depicts the powder X-ray diffraction pattern (PXRD) of N-methyl-2-(4-methyl-1,4-diazepan-1-yl)benzo[4,5]imidazo[1,2-a][1,8]naphthyridine-6-carbaxomide (Compound (I)) in multiphasic form (starting material); and Form 4 as produced by the dichloromethane evaporative crystallization process.

Form 4 of Compound (I) was made by dissolving 200 mg Compound (I) in 2.2 mL of dichloromethane. The resulting suspension was filtered and allowed to undergo evaporative crystallization at ambient conditions in an uncapped vial. PXRD analysis of Form 4 is shown in FIG. 10.

Form 4 was produced on a large scale from evaporative crystallization from Compound (I) in dichloromethane.

Figure 40:
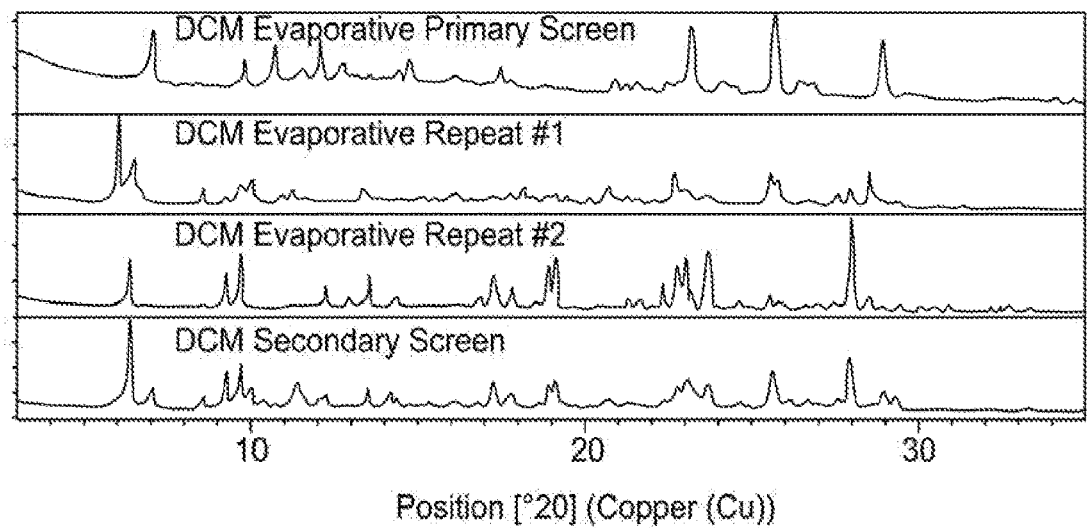
FIG. 40 depicts the powder X-ray diffraction pattern (PXRD) of Form 4 produced from the DCM evaporative in the primary screen and repeats (top 3); and the powder X-ray diffraction pattern (PXRD) of Form 4 produced from the DCM slurry in the secondary screen (bottom).

PXRD analysis showed the form produced from a primary screen as un-reproducible (See, FIG. 40). However, a secondary screen produced the same form as a repetition of the primary screen (See, FIG. 39, DCM evaporative repeat #1). This crystal form appears to be a mixture of material produced in two repeats of this experiment (See, FIG. 39, repeat #1 and repeat #2).

Figure 41:
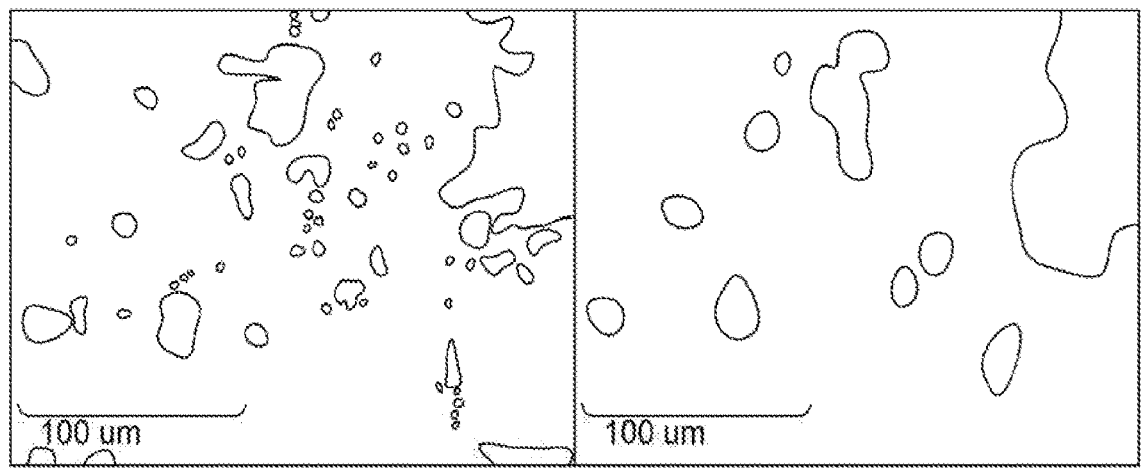
FIG. 41 depicts Polarized Light Microscopy (PLM) results of Form 4.

PLM images show Form 4 to consist of small birefringent particles of no defined morphology (See, FIG. 41).

Figure 42:
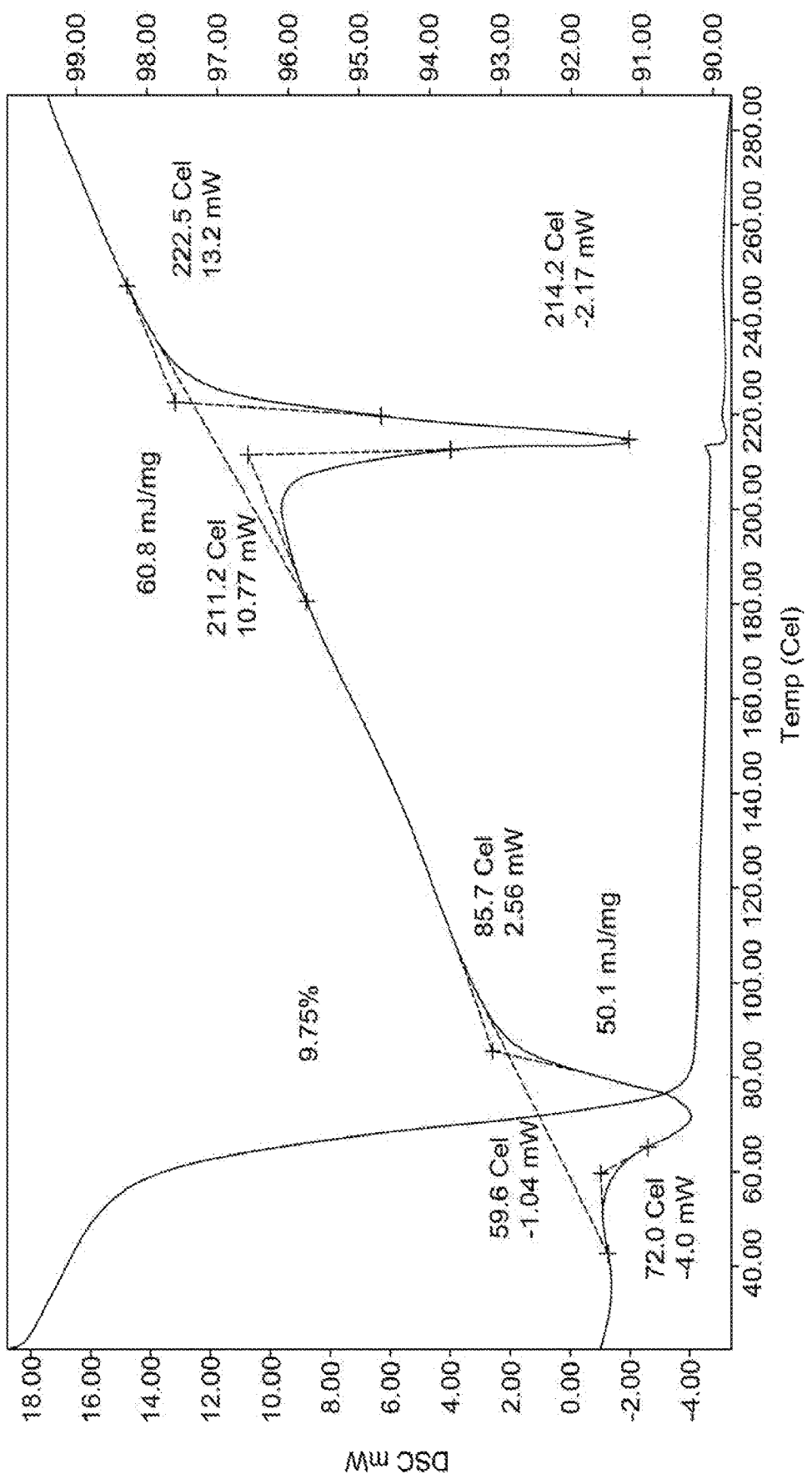
FIG. 42 depicts the Thermogravimetric Analysis (TGA) and Differential Thermal Analysis (DTA) of Form 4.

TG/DTA of Form 4 shows a mass loss of 9.75%, which coincides with an endothermic event with an onset of 59.6° C., and peak at 72° C. (See, FIG. 42). These events are indicative of desolvation of material.

Figure 43:
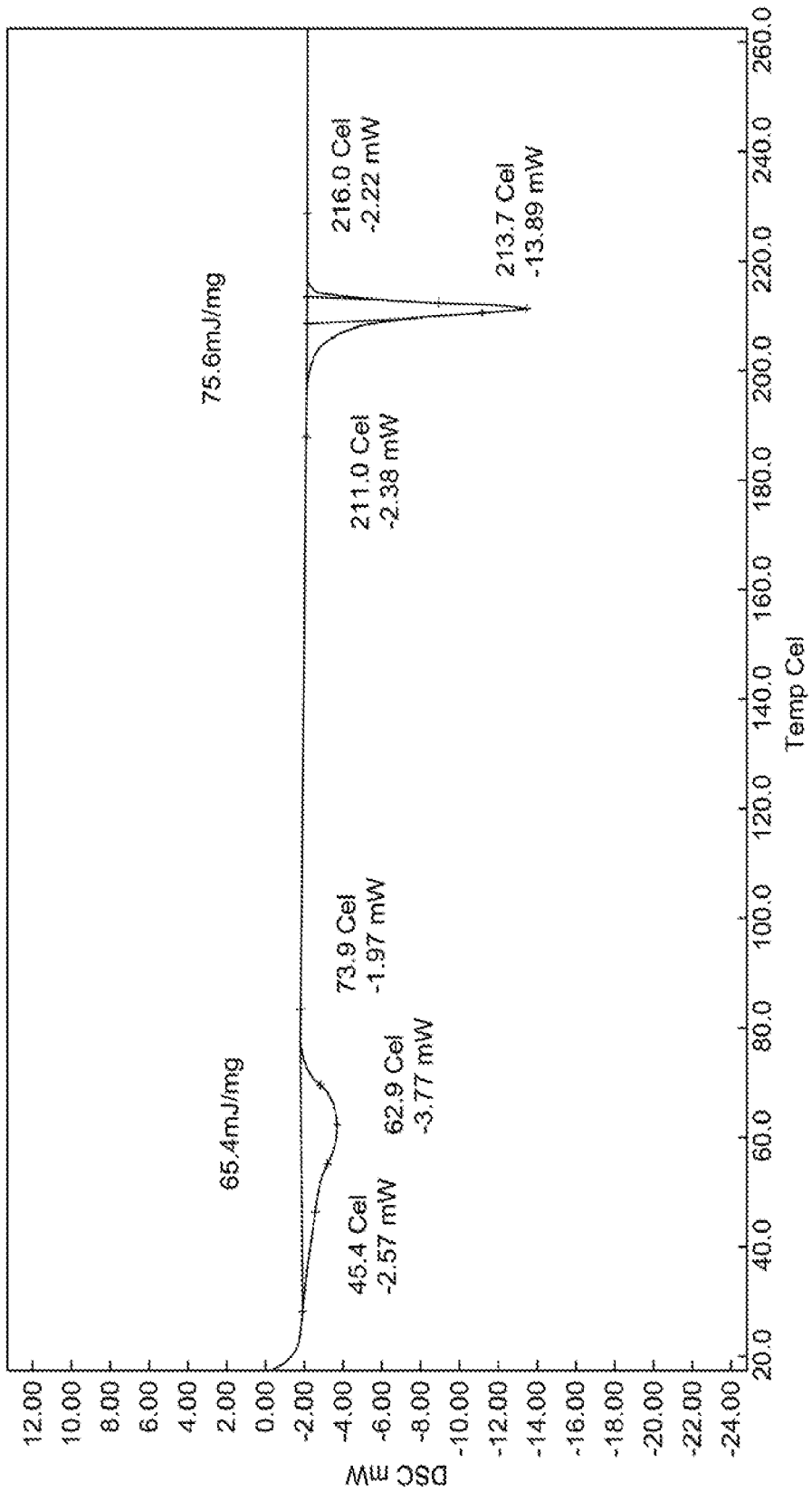
FIG. 43 depicts the Differential Scanning Calorimetry (DSC) thermogram (1$^{st}$ heating cycle) of Form 4.

A second endothermic event, likely due to melt of material onsets at 211.2° C., and peak at 214.2° C. DSC analysis of first heating cycle shows a small endothermic event at 46.4° C., and peak at 62.9° C. (See, FIG. 43). On comparison to TGA trace, it is predicted to correspond to desolvation of Form 4. A second endothermic event, due to melt of Compound (I) has an onset of 211° C., and peak at 213.7° C.

Figure 44:
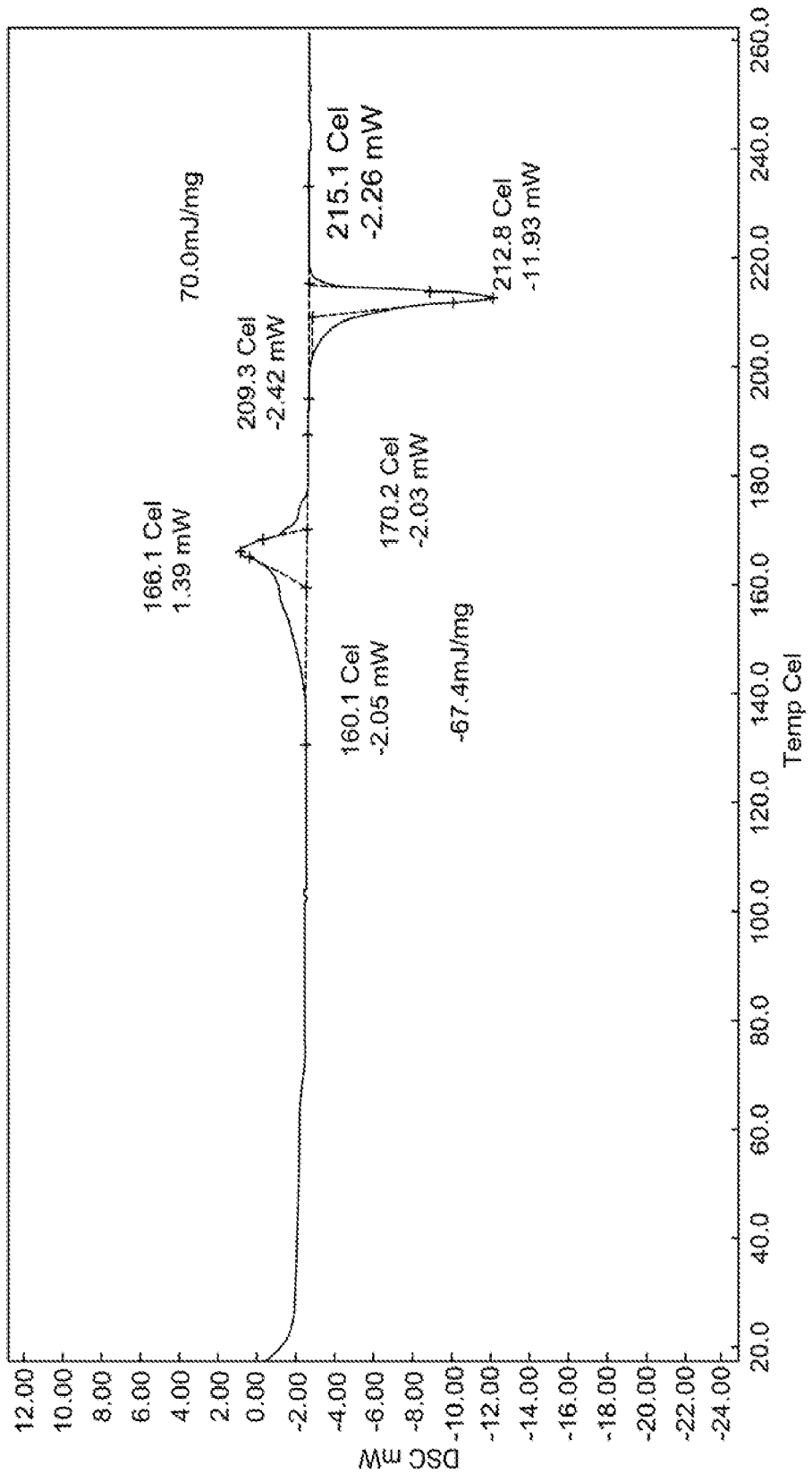
FIG. 44 depicts the Differential Scanning Calorimetry (DSC) thermogram (2$^{nd}$ heating cycle) of Form 4.

On second heating cycle, an exothermic event is observed with onset of 160.1° C., and peak at 166.1° C., likely associated with re-crystallization of Form 4 (See, FIG. 44). This leads into an endothermic event which with onset of 209.3° C., and peak at 213.8° C., corresponding to the melt of Compound (I).

Figure 45:
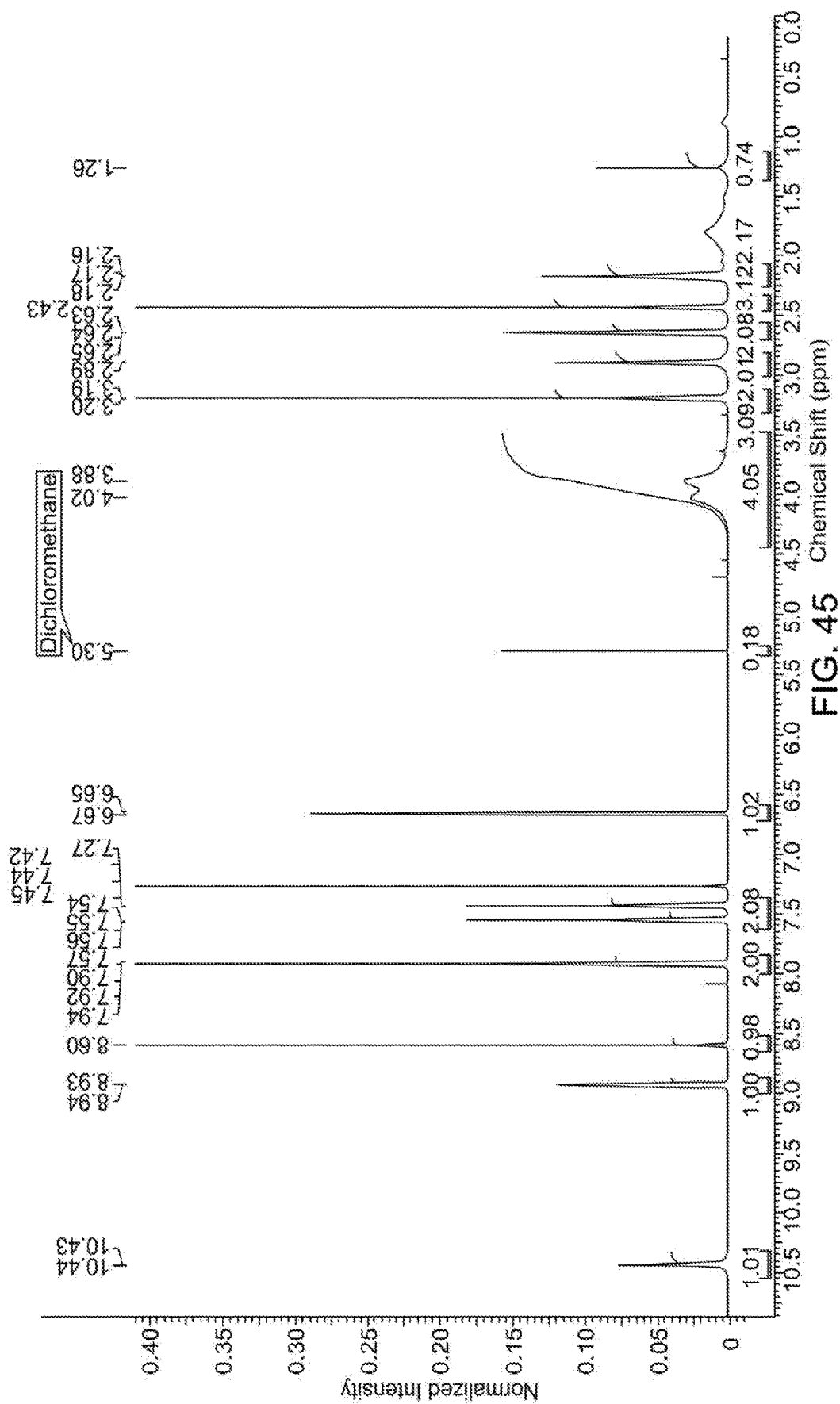
FIG. 45 depicts the $^1$H NMR analysis (CDCl$_3$, 500 MHz) of Form 4.

¹H NMR spectra shows the chemical integrity of Compound (I) within Form 4 (See, FIG. 45). Presence of dichloromethane may be seen at 5.3 ppm.

Form 4 is stable and maintains its form after 7-day storage under ambient conditions (closed vial). After 7-day storage under 40° C./75% RH (closed vial), Form 4 transitions to Form 1. FIG. 52 provides the results of a post-storage PXRD analysis of Form 4.

Crystalline Form 5 of N-Methyl-2-(4-Methyl-1,4-Diazepan-1-Yl)Benzo[4,5]Imidazo[1,2-A][1,8]Naphthyridine-6-Carbaxomide (Compound I)

Figure 11:
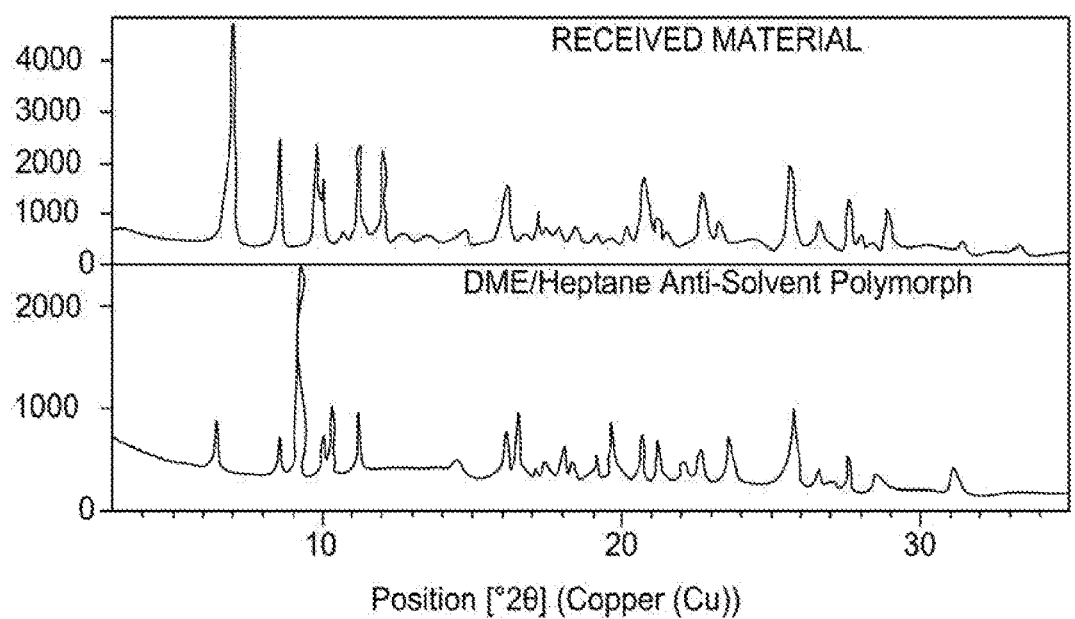
FIG. 11 depicts the powder X-ray diffraction pattern (PXRD) of N-methyl-2-(4-methyl-1,4-diazepan-1-yl)benzo[4,5]imidazo[1,2-a][1,8]naphthyridine-6-carbaxomide (Compound (I)) in multiphasic form (starting material); and Form 5 as produced by the dichloromethane/heptane antisolvent combination process.

Form 5 of Compound (I) was made by dissolving 200 mg of Compound (I) in 2.2 mL of dichloromethane. 20 mL of heptane was added to the resulting suspension to precipitate the material back out of the solution. PXRD analysis of Form 5 is shown in FIG. 11.

Figure 46:
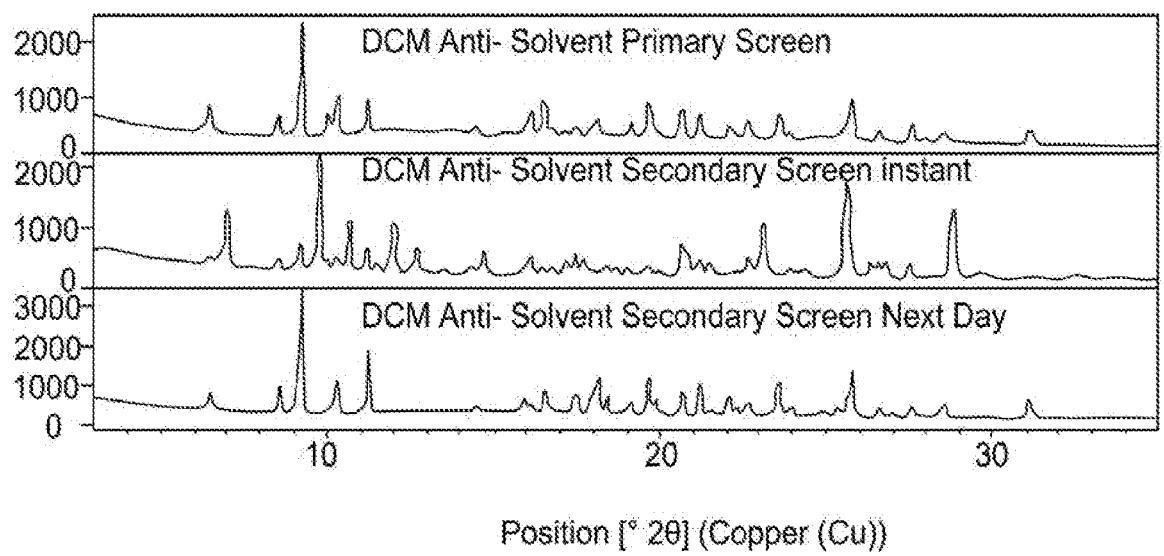
FIG. 46 depicts the powder X-ray diffraction pattern (PXRD) of Form 5 produced from the DCM anti-solvent primary screen and repeats (top); the powder X-ray diffraction pattern (PXRD) of Form 5 produced from the DCM anti-solvent secondary screen (middle); and the powder X-ray diffraction pattern (PXRD) of Form 5 produced from the DCM anti-solvent secondary screen the following day (bottom).

Form 5 was produced on a large scale. PXRD analysis confirms Form 5 was not initially reproducible on a larger scale. (See, FIG. 46, DCM anti-solvent instant).

The dichloromethane/heptanes solution was left overnight and a transition into Form 5 was observed on analysis (DCM-Anti-solvent secondary screen next day).

Figure 47:
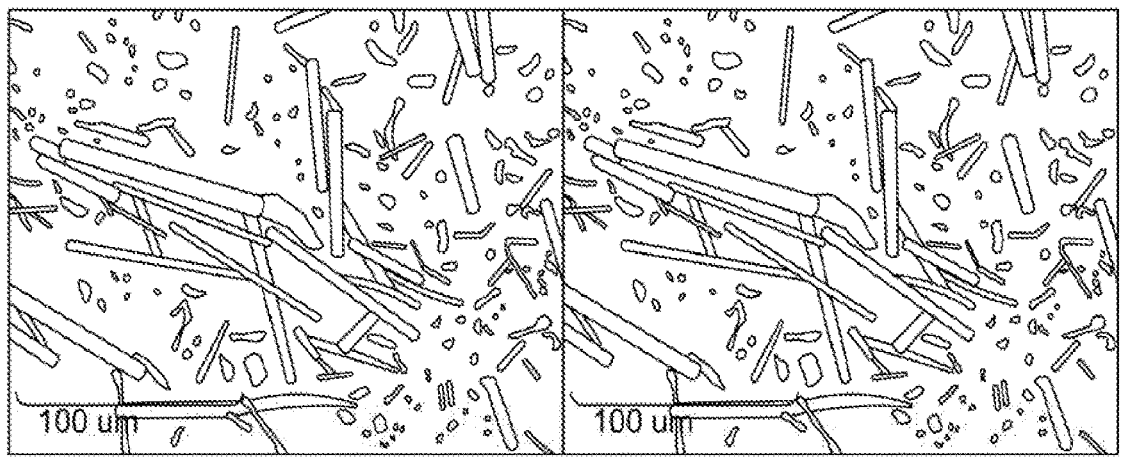
FIG. 47 depicts Polarized Light Microscopy (PLM) results of Form 5 post drying.

PLM analysis shows Form 5 to consist of large rod-shaped particles which display birefringence post drying (See, FIG. 47).

Figure 48:
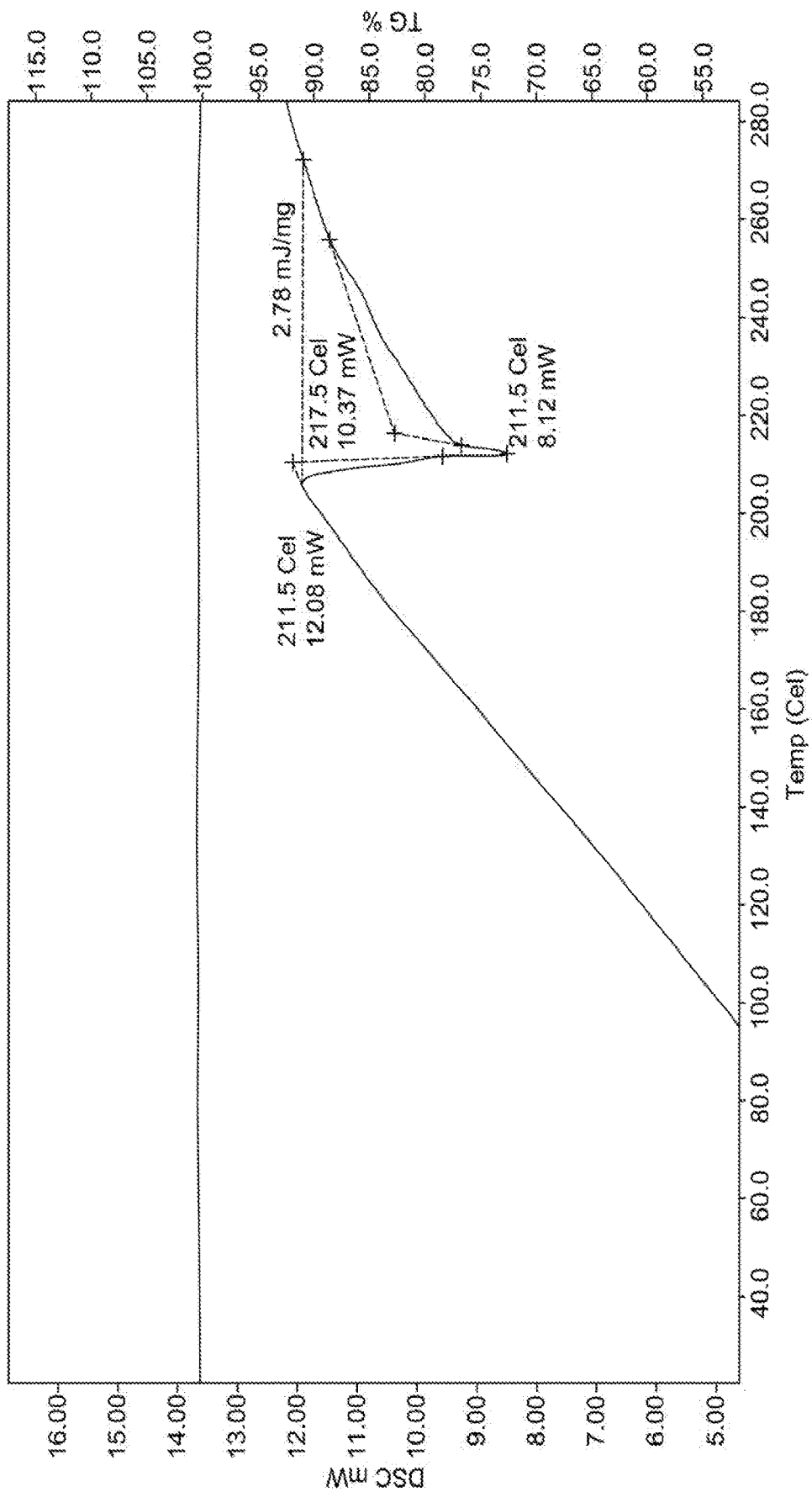
FIG. 48 depicts the Thermogravimetric Analysis (TGA) and Differential Thermal Analysis (DTA) of Form 5.

TGA trace shows Form 5 displays a mass loss of 0.2% up to 300° C., however this is likely due to events occurring in the pan as Form 5 melts rather than a true event (See, FIG. 48). An endothermic event is observed with onset of 211.5° C., and peak at 213.5° C. indicative of the melt of Compound (I).

Figure 49:
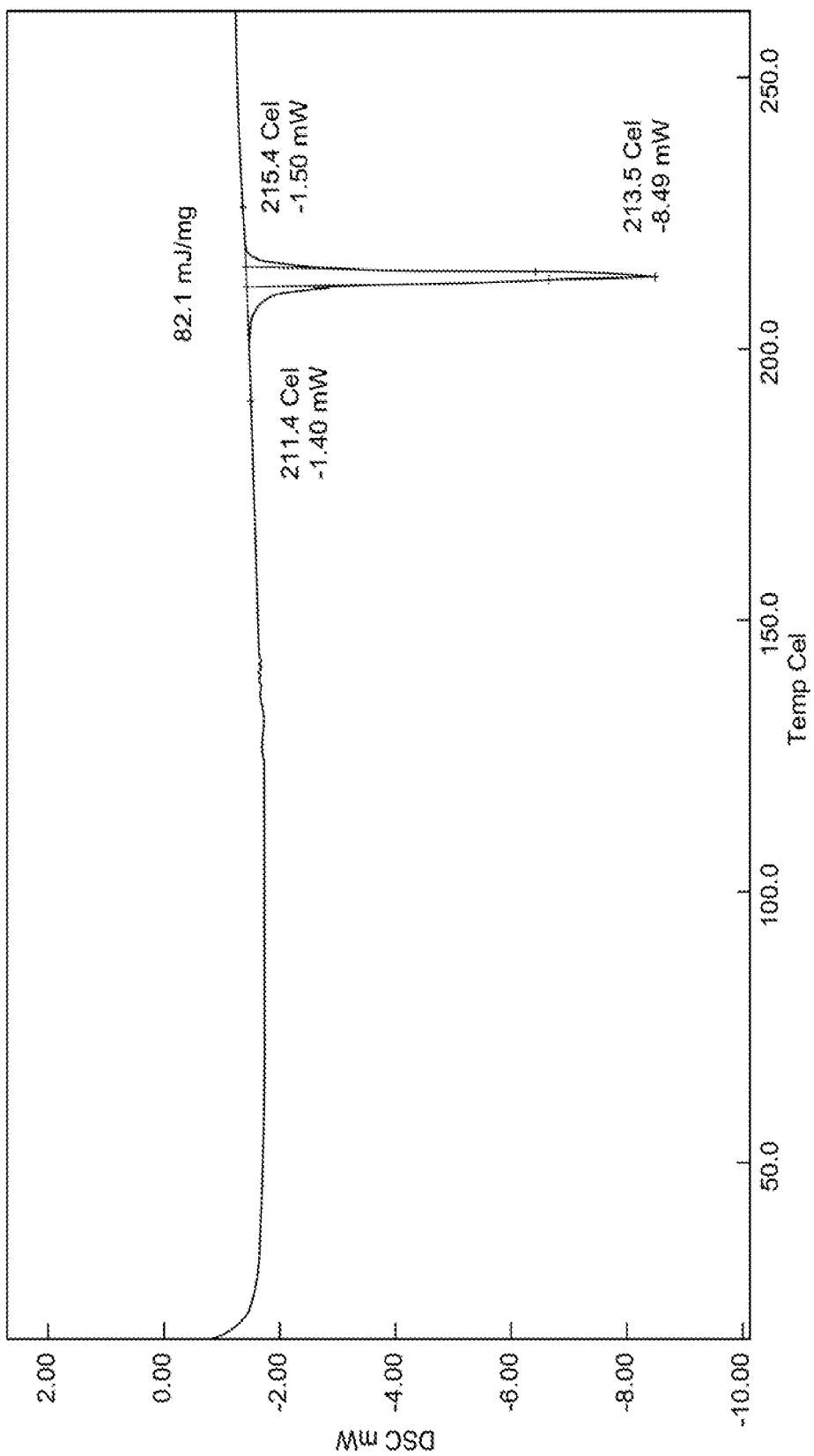
FIG. 49 depicts the Differential Scanning Calorimetry (DSC) thermogram (1$^{st}$ heating cycle) of Form 5.
Figure 50:
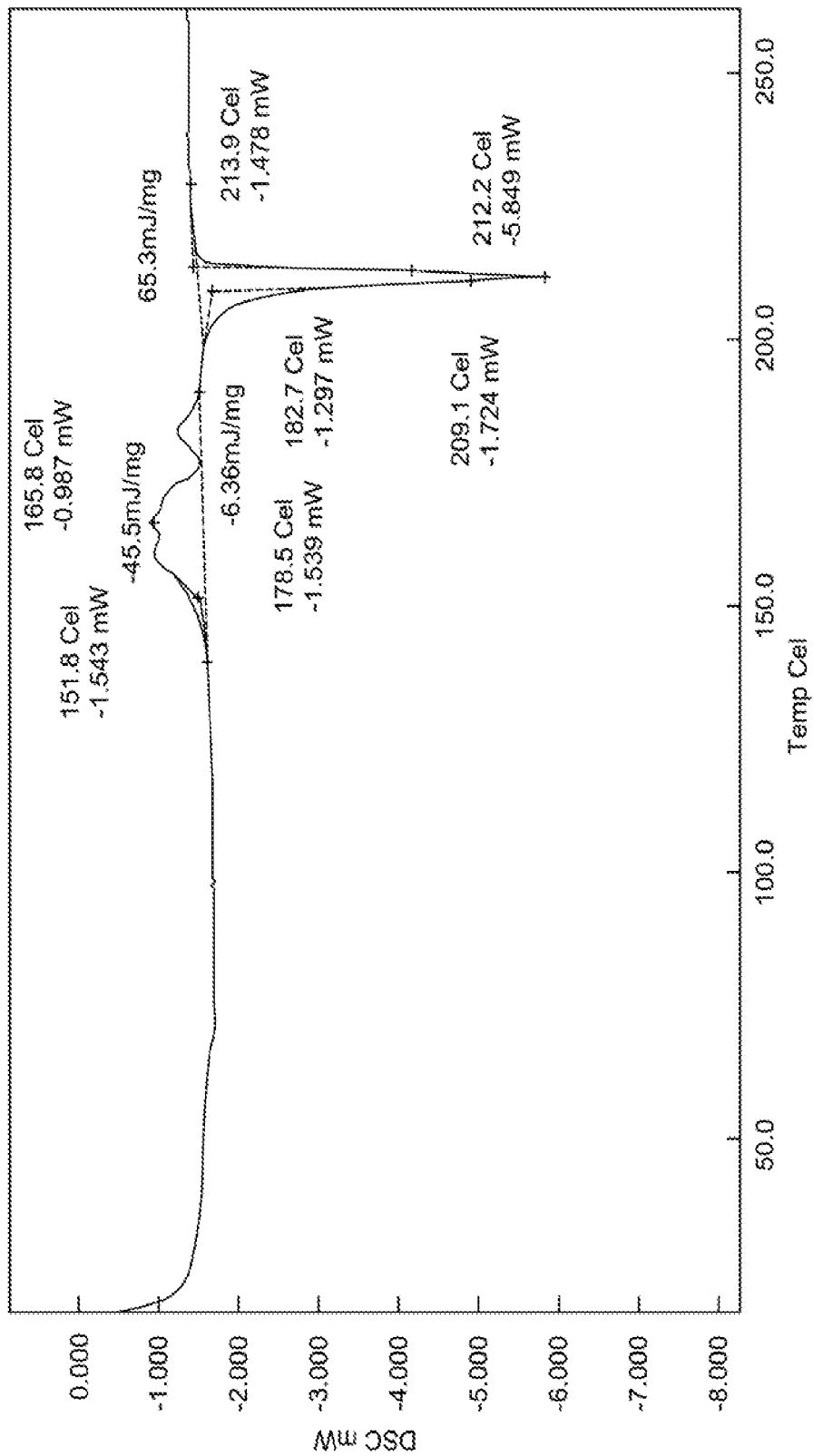
FIG. 50 depicts the Differential Scanning Calorimetry (DSC) thermogram (2$^{nd}$ heating cycle) of Form 5.

DSC analysis of first heating cycle is clean with one endothermic event with onset of 211.4° C., and peak at 213.5° C., indicative of melt of material (See, FIG. 49). The second heating cycle shows two exothermic peaks. The first exothermic event has an onset of 151.8° C., and peak at 165.8° C., this leads directly into the smaller exothermic event with an onset of 178.5° C., and peak at 182.7° C. An endothermic event was observed with onset of 209.1° C., and peak at 212.2° C., likely due to melt of Compound (I).

Figure 51:
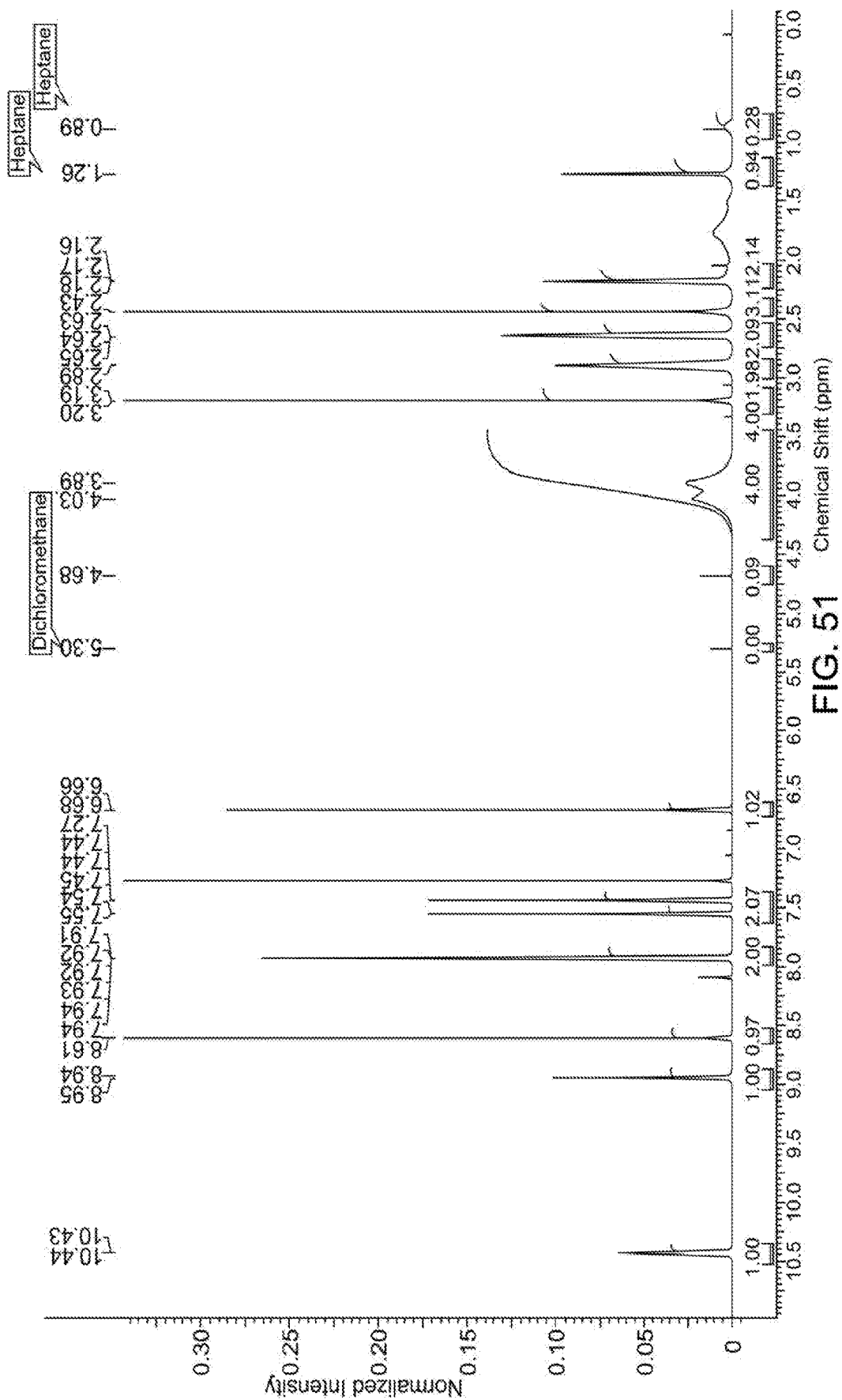
FIG. 51 depicts the $^1$H NMR analysis (CDCl$_3$, 500 MHz) of Form 5.

$^1$H NMR spectra shows the chemical structure of Form 5 (See, FIG. 51). Presence of dichloromethane may be seen at 5.30 ppm.

Form 5 is stable and maintains its form after 7-day storage under ambient conditions and under 40° C./75% RH (closed vial).

Pharmaceutical Compositions

The crystalline forms described herein (e.g., the crystalline Forms 1, 2, 3, 4, and 5) may be used in the preparation of a composition, such as a pharmaceutical composition, by combining the described crystalline form with one or more pharmaceutical acceptable carriers, excipients, stabilizing agents and/or other agents, which are known in the art, for use in the methods of treatment, methods of administration, and dosage regimes described herein.

The compositions may vary or be tailored according to the condition to be treated, the amount of compound to be administered, the condition of the individual, and other variables that will readily be apparent to one of ordinary skill in the art in view of the teachings provided herein. The crystalline forms may be formulated, for example, as a solid, semi-solid, and liquid dosage forms, such as tablets, pills, powders, liquid solutions or suspensions (e.g., when formulated with a surface interaction inhibitor), suppositories, injectable and infusible solutions, and sprays. The preferred form depends on the intended mode of administration and therapeutic application. The following compositions, additives, and methods are merely exemplary and are in no way limiting.

Additives used with crystalline forms described herein (e.g., the crystalline Forms 1, 2, 3, 4, and 5) include, for example, one or more excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents, viscosity-increasing agents (e.g., one or more viscosity-increasing agents), surface interaction inhibitors, and the like, either alone or together with one or more additional pharmaceutical agents, provided that the additional components are pharmaceutically acceptable for the particular disease to be treated (e.g., cancer). In some embodiments, the composition may include combinations of two or more of the additional components as described herein (e.g., 2, 3, 4, 5, 6, 7, 8, or more additional components). In some embodiments, the composition may comprise a crystalline form combined with a surface interaction inhibitor, which creates a physical barrier between adjacent particles. In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-.beta.-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Merck Pub. Co., New Jersey 18$^{th}$ edition (1996), and REMINGTON: THE SCIENCE AND PRACTICE OF PHARMACY, Lippincott Williams & Wilkins, Philadelphia, 20$^{th}$ edition (2003) and 21st edition (2005); Rowe, Raymond C; Sheskey, Paul J; Cook, Walter G; Fenton, Marian E., Handbook of Pharmaceutical Excipients, Seventh edition.

Compositions suitable for oral administration may comprise, for example, (a) liquid solutions (e.g., a crystalline form combined with one or more solvents with a surface interaction inhibitor), such as an effective amount of the compound dissolved in diluents, such as water, saline, or orange juice, (b) capsules, sachets or tablets, each containing a predetermined amount of the active ingredient, as solids or granules, (c) suspensions (including microsuspensions) in an appropriate liquid, (d) suitable emulsions, and (e) powders. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The crystalline forms described herein (e.g., the crystalline Forms 1, 2, 3, 4, and 5) may be enclosed in a hard or soft capsule, may be compressed into tablets, or may be incorporated with beverages or food or otherwise incorporated into the diet. Capsules may be formulated by mixing the crystalline form with an inert pharmaceutical diluent and inserting the mixture into a hard gelatin capsule of the appropriate size. If soft capsules are desired, a slurry of the crystalline form with an acceptable vegetable oil, light petroleum or other inert oil can be encapsulated by machine into a gelatin capsule.

Liquid dosage forms for oral administration may include pharmaceutically acceptable emulsions, solutions, suspensions, syrups, and elixirs containing inert diluents commonly used in the art, such as water. Such formulations may also comprise adjuvants, such as surface interaction inhibitors, wetting agents, emulsifying and suspending agents, cyclodextrins, and sweetening, flavoring, and perfuming agents. The skilled artisan will appreciate that complete solvation of crystalline or amorphous solids is not encompassed by the instant invention and the crystalline form should be insoluble in the carrier to preserve the crystalline form that is to be employed in the specific composition.

Compositions suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The compositions may be presented in unit-dose or multi-dose sealed containers, such as ampules and vials, and can be stored in a freeze-dried (lyophilized) condition requiring only the addition of the sterile liquid excipient methods of treatment, methods of administration, and dosage regimes described herein (i.e., water) for injection, immediately prior to use. Extemporaneous injection solutions and suspensions may be prepared from sterile powders, granules, and tablets of the kind previously described.

Injectable preparations (for example, sterile injectable aqueous or oleaginous suspensions) may be formulated according to the known art using suitable dispersing or wetting agents and suspending agents. In some embodiments, the crystalline forms described herein, such as an amorphous salt form or crystalline forms described herein (e.g., the crystalline Forms 1, 2, 3, 4, and 5) is formulated as a microsuspension (e.g., for parenteral administration, oral administration, or otherwise). Microsuspensions are thermodynamically stable dispersions of microcrystals, which may be stabilized by an interfacial film of surfactant molecules functioning as a dispersing agent (Encyclopedia of Pharmaceutical Technology (New York: Marcel Dekker, 1992), volume 9, the content of which is hereby incorporated by reference).

The sterile injectable preparation may also be a sterile injectable solution or suspension in a nontoxic parenterally acceptable diluent or solvent, for example, as a solution in propylene glycol. The sterile injectable preparation may also be a sterile powder to be reconstituted using acceptable vehicles prior to administration. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables.

Compositions derived from the crystalline forms described herein (e.g., the crystalline Forms 1, 2, 3, 4, and 5) formulated in liquid form (for oral administration, parenteral administration, or otherwise) may have a pH in the range of about 3.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (e.g., about 8). The composition can also be made to be isotonic with blood by the addition of a suitable tonicity modifier, such as glycerol.

The crystalline forms described herein (e.g., the crystalline Forms 1, 2, 3, 4, and 5) may also be formulated for administration by inhalation. Compositions suitable for aerosol administration which comprise the crystalline form may include, for example, aqueous and non-aqueous, isotonic sterile solutions, which can contain anti-oxidants, buffers, bacteriostats, and solutes, as well as aqueous and non-aqueous sterile suspensions that can include suspending agents, solubilizers, thickening agents, stabilizing agents, and preservatives, alone or in combination with other suitable components, which can be made into aerosol compositions to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Various sustained release systems for drugs have also been devised, and can be applied to Salt forms of the invention. See, for example, U.S. Pat. No. 5,624,677, the methods of which are incorporated herein by reference.

The crystalline forms described herein (e.g., the crystalline Forms 1, 2, 3, 4, and 5) may also be formulated in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The crystalline forms described herein (e.g., the crystalline Forms 1, 2, 3, 4, and 5) may also be formulated for topical administration, especially when the target of treatment includes areas or organs readily accessible by topical application, including diseases of the eye, the skin, or the lower intestinal tract. Suitable topical compositions are readily prepared for each of these areas or organs.

Topical application for the lower intestinal tract can be effected in a rectal suppository formulation (see above) or in a suitable enema formulation. Topically-transdermal patches may also be used.

Also provided are unit dosage forms comprising the compositions described herein (e.g., compositions comprising a crystalline form described herein (e.g., the crystalline Forms 1, 2, 3, 4, and 5). These unit dosage forms can be stored in a suitable packaging in single or multiple unit dosages and may also be further sterilized and sealed. For example, the pharmaceutical formulation (e.g., a dosage or unit dosage form of a pharmaceutical composition) may include (i) a crystalline form and (ii) a pharmaceutically acceptable carrier. In some embodiments, the pharmaceutical composition also includes one or more other compounds (or pharmaceutically acceptable salts thereof) that are useful for treating a particular condition (e.g., cancer).

In various variations, the amount of crystalline form in the composition is included in any of the following ranges: about 5 to about 50 mg, about 20 to about 50 mg, about 50 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of crystalline form in the composition (e.g., a dosage or unit dosage form) is in the range of about 5 mg to about 500 mg, such as about 30 mg to about 300 mg or about 50 mg to about 200 mg. In some embodiments, the composition and carrier are suitable for oral administration. In some embodiments, the crystalline form is the only pharmaceutically active agent for the treatment of the condition (e.g., cancer) that is contained in the composition.

Kits

Also provided are kits containing materials useful for the treatment of a disease (e.g., cancer) that is responsive to a crystalline form described herein (e.g., the crystalline Forms 1, 2, 3, 4, and 5). The kits may contain a crystalline form described herein (e.g., the crystalline Forms 1, 2, 3, 4, and 5) and optionally contain instructions for use (e.g., instructions for preparation and/or administration of a composition comprising the crystalline form). Information detailing possible side effects of the composition, and any other relevant information may also be enclosed. The instructions may be in any suitable format, including, but not limited to, printed matter, videotape, computer readable disk, optical disc or directions to internet-based instructions.

In one aspect, is provided a kit for treating an individual who suffers from or is susceptible to the disease or conditions described herein (e.g., cancer), comprising a first container comprising a dosage amount of a formulation as disclosed herein, and instructions for use. The container may be any of those known in the art and appropriate for storage and delivery of intravenous formulation. In certain embodiments the kit further comprises a second container comprising a pharmaceutically acceptable carrier, diluent, adjuvant, etc. for preparation of the formulation to be administered to the individual.

In some embodiments, the kits comprise a container with a label. Suitable containers include, for example, bottles, vials, and test tubes. The containers may be formed from a variety of materials such as glass or plastic. The containers may hold a crystalline form described herein (e.g., the crystalline Forms 1, 2, 3, 4, and 5) or a composition thereof. The label on the container may indicate that the crystalline form, the composition, or the pharmaceutically active agent (compound (I)) is used for treating or suppressing a condition that is responsive to compound (I) (e.g., cancer), and may also indicate directions for either in vivo or in vitro use, such as those described herein.

The kit may further include other materials desirable from a commercial and user standpoint, including other buffers, diluents, filters, needles, syringes, and package inserts with instructions for performing any methods described herein. In some embodiments, the kit comprises the container described above and a second container comprising a buffer.

The kits may include additional pharmaceutical agents for use in conjunction with the formulation described herein. In some variations, the additional pharmaceutical agent(s) may be one or more anticancer drug(s). These agents may be provided in a separate form, or mixed with the crystalline forms described herein, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein (e.g., cancer).

Kits may also be provided that contain sufficient dosages of the compounds described herein (including compositions thereof) to provide effective treatment for an individual for an extended period, such as 1-3 days, 1-5 days, 1 week, 2 weeks, 3, weeks, 4 weeks, 6 weeks, 8 weeks, 3 months, 4 months, 5 months, 6 months, 7 months, 8 months, 9 months or more.

The kits may include the composition as described herein packaged in either a unit dosage form or in a multi-use form. The kits may also include multiple units of the unit dose form. The kits may be used for any of the methods described herein, including, for example, to treat an individual with cancer, or to delay cancer. In certain embodiments the kits may include a dosage amount of at least one formulation as disclosed herein. Kits may also comprise a means for the delivery of the composition thereof.

Methods of Treatment

The crystalline forms described herein (e.g., the crystalline Forms 1, 2, 3, 4, and 5) may described herein, or a pharmaceutically acceptable salt thereof, are used in the preparation of medicaments for the treatment of diseases or conditions in a mammal that would benefit from inhibiting POL1 transcription. Methods for treating any of the diseases or conditions described herein in a mammal in need of such treatment, involves administration of pharmaceutical compositions that include at least one crystalline form described herein or a pharmaceutically acceptable salt, active metabolite, prodrug, or pharmaceutically acceptable solvate thereof, in therapeutically effective amounts to said mammal.

In some embodiments, the invention provides methods of treating conditions associated with polymerase I transcription, comprising: administering to a patient in need thereof an effective amount of a crystalline form of the invention. In another embodiment, the invention provides a method of inhibiting polymerase I transcription: comprising, contacting the enzyme with an active form of the invention. In a further embodiment, the invention provides a method of inhibiting polymerase I transcription: comprising, administering a first crystalline form to a subject that is converted in vivo to an active form of the invention.

"Conditions associated with polymerase I transcription" include disorders and diseases in which the inhibition of polymerase I transcription provides a therapeutic benefit, such as cancer, allergy/asthma, diseases and conditions of the immune system, inflammation, disease and conditions of the central nervous system (CNS), cardiovascular disease, viral infections, dermatological disease, and diseases and conditions related to uncontrolled angiogenesis, and the like. Where general terms are used herein to describe conditions associated with polymerase I transcription it is understood that the more specifically described conditions mentioned in the various diagnostic manuals and other materials are included within the scope of this invention.

The term "cancer," as used herein refers to an abnormal growth of cells, which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias). See, Ding X Z et al., Anticancer Drugs. 2005 June; 16(5):467-73. Review; Chen X et al., Clin Cancer Res. 2004 Oct. 1; 10(19):6703-9, each of which are incorporated by reference herein in their entirety.

For example, it is understood that the treatment of cancer includes treatment of all neoplasia, regardless of their histopathological appearance. Particularly, the cancers that can be treated include, but are not limited to, cancer of blood, including myelofibrosis, leukemia (including acute myelogenous leukemia, chronic myelogenous leukemia, acute lymphocytic leukemia, chronic lymphocytic leukemia), cancer of the skin, including melanoma, basal cell carcinoma, and squamous cell carcinoma, bone, liver, lung (including small-cell lung tumor, non small-cell lung cancer and bronchioalveolar cancer), brain, breast, prostate, larynx, gall bladder, pancreas, rectum, bile duct, parathyroid, thyroid, adrenal, neural tissue, bladder, spleen, head and neck, included the jaw, mouth, and nose, colon, stomach, testes, esophagus, uterus, cervix and vulva, colorectal, bronchi, bile duct, bladder, kidney, ovary, pancreas, multiple myeloma, lymphomas, basal cell carcinoma, squamous cell carcinoma of both ulcerating and papillary type, osteo sarcoma, Ewing's sarcoma, veticulum cell sarcoma, myeloma, giant cell tumor, islet cell tumor, acute and chronic lymphocytic and granulocytic tumors, hairy-cell tumor, adenoma, hyperplasia, medullary carcinoma, pheochromocytoma, mucosal neuroma, intestinal ganglioneuromas, hyperplastic corneal nerve tumor, marfanoid habitus tumor, Wilm's tumor, seminoma, ovarian tumor, leiomyomata tumor, cervical dysplasia and in situ carcinoma, neuroblastoma, retinoblastoma, myelodysplastic syndrome, mycosis fungicide, rhabdomyosarcoma, astrocytoma, non-Hodgkin's lymphoma, Kaposi's sarcoma, osteogenic and other sarcoma, malignant hypercalcemia, polycythermia vera, adenocarcinoma, glioblastoma multiforma, glioma, lymphomas, epidermoid carcinomas, and other carcinomas and sarcomas.

Benign tumors may also be treated by the crystalline forms of the present invention and include, but are not limited to, hemangiomas, hepatocellular adenoma, cavernous hemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, and the like, and hamartoma conditions such as Peutz-Jeghers Syndrome (PJS), Cowden disease, Bannayan-Riley-Ruvalcaba Syndrome (BRRS), *Proteus* syndrome, Lhermitte-Duclos disease and Tuberous Sclerosis (TSC).

The crystalline forms described herein (e.g., the crystalline Forms 1, 2, 3, 4, and 5) may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome.

The crystalline forms described herein (e.g., the crystalline Forms 1, 2, 3, 4, and 5) may also be useful in the prevention of restenosis that is the control of undesired proliferation of normal cells in the vasculature in response to the introduction of stents in the treatment of vasculature disease.

Proliferative responses associated with organ transplantation that may be treated using Pol I transcription inhibitors of the invention include proliferative responses contributing to potential organ rejections or associated complications. Specifically, these proliferative responses may occur during transplantation of the heart, lung, liver, kidney, and other body organs or organ systems.

The crystalline forms described herein (e.g., Forms 1, 2, 3, 4, and 5) may also be useful the treatment of abnormal angiogenesis including the abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroblastic), macular degeneration, corneal graft rejection, neuroscular glaucoma, Oster Webber syndrome, retinal/choroidal neuvascularization and corneal neovascularization, Best's disease, myopia, optic pits, Stargart's diseases, Pagets disease, vein occlusion, artery occlusion, sickle cell anemia, sarcoid, syphilis, pseudoxanthoma elasticum carotid obstructive diseases, chronic uveitis/vitritis, mycobacterial infections, Lyme's disease, systemic lupus erythematosis, retinopathy of prematurity, Eales disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle), diseases caused by the abnormal proliferation of fibrovascular or fibrous tissue including all forms of proliferative vitreoretinopathy, atopic keratitis, superior limbic keratitis, pterygium keratitis sicca, sjogrens, acne rosacea, phylectenulosis, diabetic retinopathy, retinopathy of prematurity, corneal graft rejection, Mooren's ulcer, Terrien's marginal degeneration, marginal keratolysis, polyarteritis, Wegener sarcoidosis, scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections, and Kaposi sarcoma, Alzheimer's disease, Parkinson's disease amyotrophic lateral sclerosis (ALS), epilepsy, seizures, Huntington's disease, polyglutamine diseases, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

For example, it is understood that treatments of inflammation include, but are not limited to, acute pancreatitis, chronic pancreatitis, asthma, allergies, chronic obstructive pulmonary disease, adult respiratory distress syndrome and chronic inflammatory diseases associated with uncontrolled angiogenesis, inflammatory bowel diseases such as Crohn's disease and ulcerative colitis, psoriasis, sarcoidosis, and rheumatoid arthritis, sarcoidosis, and multisystem granulomatous disorder.

For example, it is understood that treatment of autoimmune includes, but is not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, or Sjogren's syndrome.

In certain embodiments, the compositions containing the crystalline form(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the crystalline forms described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal that previously experienced at least one symptom of the disease being treated and is currently in remission, a pharmaceutical composition comprising a crystalline form described herein, or a pharmaceutically acceptable salt thereof, in order to prevent a return of the symptoms of the disease or condition.

In certain embodiments wherein the patient's condition does not improve, upon the doctor's discretion the administration of the crystalline forms are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular crystalline form, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg to 5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the crystalline form described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the crystalline form used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the crystalline forms described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the crystalline forms described herein (e.g., Forms 1, 2, 3, 4, and 5), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the crystalline forms described herein (e.g., Forms 1, 2, 3, 4, and 5), including further embodiments in which (i) the crystalline forms described herein (e.g., Forms 1, 2, 3, 4, and 5) is administered once a day; or (ii) the crystalline forms described herein (e.g., Forms 1, 2, 3, 4, and 5) is administered to the mammal multiple times over the span of one day.

In any of the aforementioned aspects are further embodiments comprising multiple administrations of the effective amount of the crystalline forms described herein (e.g., the crystalline Forms 1, 2, 3, 4, and 5), including further embodiments in which (i) the crystalline forms described herein (e.g., the crystalline Forms 1, 2, 3, 4, and 5) is administered continuously or intermittently: as in a single dose; (ii) the time between multiple administrations is every 6 hours; (iii) the crystalline forms described herein (e.g., the crystalline Forms 1, 2, 3, 4, and 5) is administered to the mammal every 8 hours; (iv) the crystalline forms described herein (e.g., the crystalline Forms 1, 2, 3, 4, and 5) is administered to the mammal every 12 hours; (v) the crystalline forms described herein (e.g., the crystalline Forms 1, 2, 3, 4, and 5) is administered to the mammal every 24 hours. In further or alternative embodiments, the method comprises a drug holiday, wherein the administration of the crystalline forms described herein (e.g., the crystalline Forms 1, 2, 3, 4, and 5) is temporarily suspended or the dose of the being administered is temporarily reduced; at the end of the drug holiday, dosing is resumed. In one embodiment, the length of the drug holiday varies from 2 days to 1 year.

In certain instances, it is appropriate to administer at least one crystalline form described herein (e.g., the crystalline Forms 1, 2, 3, 4, and 5), or a pharmaceutically acceptable salt thereof, in combination with one or more other therapeutic agents. In certain embodiments, the pharmaceutical composition further comprises one or more anticancer agents.

In one embodiment, the therapeutic effectiveness of one of the crystalline forms described herein (e.g., the crystalline Forms 1, 2, 3, 4, and 5), is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the forms described herein with another agent (which also includes a therapeutic regimen) that also has therapeutic benefit.

A wide variety of therapeutic agents may have a therapeutic additive or synergistic effect with the crystalline forms described herein (e.g., the crystalline Forms 1, 2, 3, 4, and 5). Combination therapies that comprise one or more crystalline forms described herein (e.g., Form 1, 2, 3, 4, and 5) with one or more other therapeutic agents can be used, for example, to: (1) enhance the therapeutic effect(s) of the crystalline forms described herein (e.g., the crystalline Forms 1, 2, 3, 4, and 5), and/or the one or more other therapeutic agents; (2) reduce the side effects exhibited by the crystalline forms described herein (e.g., the crystalline Forms 1, 2, 3, 4, and 5), and/or the one or more other therapeutic agents; and/or (3) reduce the effective dose of the crystalline forms described herein (e.g., the crystalline Forms 1, 2, 3, 4, and 5), and/or the one or more other therapeutic agents. It is noted that combination therapy is intended to cover when agents are administered before or after each other (sequential therapy) as well as when the agents are administered at the same time.

Examples of such therapeutic agents that may be used in combination with the crystalline forms described herein (e.g., the crystalline Forms 1, 2, 3, 4, and 5), include, but are not limited to, anti-cell proliferation agents, anticancer agents, alkylating agents, antibiotic agents, antimetabolic agents, hormonal agents, plant-derived agents, and biologic agents.

Anti-cell proliferation agents useful in combination with the crystalline forms described herein (e.g., the crystalline Forms 1, 2, 3, 4, and 5), but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,1-3,4-dehydroproline, thiaproline, beta-aminopropionitrile fumarate, 4-propyl-5-(4-pyridinyl)-2(3H)-oxazolone, methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide, angostatic steroid, cargboxynaminolmidazole, metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2.

Inhibitors of mTOR, PI3K, MEK, MAPK, PIM or ERK kinases are useful in combination with the crystalline forms described herein (e.g., the crystalline Forms 1, 2, 3, 4, and 5). Specifically, (R)-3-(2,3-Dihydroxypropyl)-6-fluoro-5-(2-fluoro-4-iodophenylamino)-8-methylpyrido[2,3d]pyrimidine-4,7(3H,8H)-dione. Inhibitors of Hedgehog kinase are useful in combination with the crystalline forms described herein (e.g., the crystalline Forms 1, 2, 3, 4, and 5). Proteasome inhibitors, in particular bortezomib is useful in combination with the crystalline forms described herein (e.g., the crystalline Forms 1, 2, 3, 4, and 5).

NAE inhibitors, VPS34 inhibitors, Aurora kinase, including Aurora A inhibitors, and EGFR inhibitors (both antibodies and kinase inhibitors) are useful in combination with the crystalline forms described herein (e.g., the crystalline Forms 1, 2, 3, 4, and 5).

Alkylating agents useful in combination with the crystalline forms described herein (e.g., the crystalline Forms 1, 2, 3, 4, and 5), include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum Compounds (carboplastin and cisplatin). Combination therapy including a polymerase I inhibitor and an alkylating agent is expected to have therapeutic synergistic effects in the treatment of cancer and reduce sides affects associated with these chemotherapeutic agents.

Examples of antibiotic agents useful in combination with the crystalline forms described herein (e.g., the crystalline Forms 1, 2, 3, 4, and 5), include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components.

Antimetabolic agents useful in combination with the crystalline forms described herein (e.g., the crystalline Forms 1, 2, 3, 4, and 5), include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy with an antimetabolic agent is expected to have therapeutic synergistic effects on cancer and reduce sides affects associated with these chemotherapeutic agents.

Hormonal agents useful in combination with the crystalline forms described herein (e.g., the crystalline Forms 1, 2, 3, 4, and 5), include synthetic estrogens (e.g. diethylstibestrol), antiestrogens (e.g. tamoxifen, toremifene, fluoxymesterol and raloxifene), antiandrogens (bicalutamide, nilutamide, and flutamide), aromatase inhibitors (e.g., aminoglutethimide, anastrozole and tetrazole), ketoconazole, goserelin acetate, leuprolide, megestrol acetate and mifepristone. Combination therapy including a crystalline form disclosed herein and a hormonal agent is expected to have therapeutic synergistic effects on cancer and reduce sides affects associated with these chemotherapeutic agents.

Plant-derived agents useful in combination with the crystalline forms described herein (e.g., the crystalline Forms 1, 2, 3, 4, and 5) include, but are not limited to, *vinca* alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a crystalline form described herein (e.g., the crystalline Forms 1, 2, 3, 4, and 5) and a plant-derived agent is expected to have therapeutic synergistic effects on cancer and reduce sides affects associated with these chemotherapeutic agents.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the crystalline forms described herein (e.g., the crystalline Forms 1, 2, 3, 4, and 5) will be utilized in formulating pharmaceutical composition and/or in treatment regimens when administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a crystalline forms described herein (e.g., the crystalline Forms 1, 2, 3, 4, and 5), or a pharmaceutically acceptable salt thereof, is initiated prior to, during, or after treatment with a second agent described herein, and continues until any time during treatment with the second agent or after termination of treatment with the second agent. It also includes treatments in which a crystalline forms described herein (e.g., the crystalline Forms 1, 2, 3, 4, and 5), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered Compounds vary depending on the type of co-drug employed, on the specific drug employed, on the disease or condition being treated and so forth. In additional embodiments, when co-administered with one or more other therapeutic agents, the crystalline form provided herein is administered either simultaneously with the one or more other therapeutic agents, or sequentially.

In combination therapies, the multiple therapeutic agents (one of which is a crystalline form described herein) are administered in any order or even simultaneously. If administration is simultaneous, the multiple therapeutic agents are, by way of example only, provided in a single, unified form, or in multiple forms (e.g., as a single pill or as two separate pills).

The crystalline forms described herein (e.g., the crystalline Forms 1, 2, 3, 4, and 5), or a pharmaceutically acceptable salt thereof, as well as combination therapies, are administered before, during or after the occurrence of a disease or condition, and the timing of administering the composition containing a crystalline form varies. Thus, in one embodiment, the crystalline forms described herein (e.g., the crystalline Forms 1, 2, 3, 4, and 5) are used as a prophylactic and are administered continuously to subjects with a propensity to develop conditions or diseases in order to prevent the occurrence of the disease or condition. In another embodiment, the crystalline forms described herein (e.g., the crystalline Forms 1, 2, 3, 4, and 5) and compositions are administered to a subject during or as soon as possible after the onset of the symptoms. In specific embodiments, a crystalline form described herein (e.g., the crystalline Forms 1, 2, 3, 4, and 5) is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, crystalline forms described herein (e.g., the crystalline Forms 1, 2, 3, 4, and 5) or a formulation containing the crystalline form is administered for at least 2 weeks, about 1 month to about 5 years.

In some embodiments, the crystalline forms described herein (e.g., the crystalline Forms 1, 2, 3, 4, and 5), or a pharmaceutically acceptable salt thereof, is administered in combination with chemotherapy, hormone blocking therapy, radiation therapy, monoclonal antibodies, or combinations thereof.

The present invention will be understood more readily by reference to the following examples which are provided by way of illustration and are not intended to be limiting of the present invention.

EXAMPLES

Example 1: Synthesis of Compound (I)—Multiphasic Form

Synthesis of Ethyl 1H-Benzimidazol-2-Yl Acetate

A mixture of SM1 (40 g, 370 mmol) and SM2 (73 g, 373 mmol) in ethanol (200 ml) was stirred at 90° C. overnight. The reaction was cooled to room temperature and the solvent was removed in vacuo. Water (300 ml) and DCM (500 ml) were added to the residue. The organic layer was separated, dried over $Na_2SO_4$ and the solvent removed to give Ethyl 1H-benzimidazol-2-yl acetate (40 g, 53% yield) as a pale yellow solid.

Synthesis of Ethyl 2-(4-Methyl-[1,4]Diazepan-1-yl)-1,7,11b-Triazabenzo[c]Fluorene-6-Carboxylic Acid To a suspension of SM1 (25.9 g, 148 mmol) and SM2 (30 g, 147 mmol) in ethanol (400 mL) was added SM3 (33.5 g, 394 mmol) and the mixture was stirred at room temperature for 20 min. The reaction mixture was heated to reflux for 6 h. The mixture was then cooled to 20° C. and the precipitate collected by filtration to give Ethyl 2-(4-methyl-[1,4]diazepan-1-yl)-1,7,11b-triazabenzo[c]fluorene-6-carboxylic acid (40 g, 68% yield) as a pale yellow solid.

Synthesis of Compound I

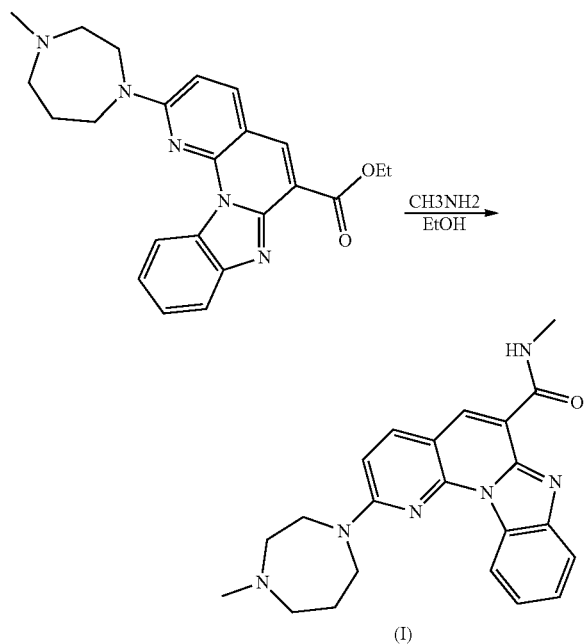

A suspension of Ethyl 2-(4-methyl-[1,4]diazepan-1-yl)-1,7,11b-triazabenzo[c]fluorene-6-carboxylic acid (40 g, 99 mmol) in $CH_3NH_2$/EtOH (2M, 400 ml, 800 mmol) was heated to reflux for 6 h. The mixture was then cooled to 20° C. and the precipitate was collected by filtration to give crude 2 G as a pale yellow solid (35 g, 86% yield). The crude product was dissolved in DCM (500 ml) and washed with water (3 times), brine, dried and concentrated to give Compound I (30.2 g, yield=78%) as a pale yellow solid.

$^1$H NMR (400 MHz, DMSO-d6) δ 10.18 (1H, d, J=4.8 Hz), 8.91 (1H, d, J=6.0 Hz), 8.58 (1H, s), 8.25 (1H, d, J=8.8 Hz), 7.91 (1H, d, J=8.0 Hz), 7.55 (1H, t, J=7.6 Hz), 7.47 (1H, t, J=7.6 Hz), 6.99 (1H, d, J=88 Hz), 4.06~3.95 (4H, m), 3.03 (3H, d, J=4.8 Hz), 2.79~2.76 (2H, m), 2.50 (2H, m), 2.28 (3H, s), 2.02 (2H, br s). LC-MS: Rt=9.160 min, 389.5[M+H]$^+$.

Example 2: Methods of Analysis

Powder X-ray Diffraction (PXRD

PXRD analysis was carried out on a PANalytical X'pert pro, scanning the samples between 3 and 35° 2θ.

The material was loaded onto a multi well plate with Kapton polymer film to support the sample. The multi well plate was then loaded into a PANalytical diffractometer running in transmission mode and analyzed, using the following experimental conditions:

| | |
|---|---|
| Raw Data Origin: XRD measurement (*.XRDML) | PSD Length [°2θ]: 3.35 |
| Scan Axis: Gonio | Offset [°2θ]: 0.0000 |
| Start Position [°2θ]: 3.0066 | Divergence Slit Type: Fixed |
| End Position [°2θ]: 34.9866 | Divergence Slit Size [°]: 1.0000 |
| Step Size [°2θ]: 0.0130 | Anode Material: Cu |
| Scan Step Time [s]: 18.8700 | K-Alpha1 [Å]: 1.54060 |
| Goniometer Radius [mm]: 240.00 | K-Alpha2 [Å]: 1.54443 |
| PSD Mode: Scanning | K-Beta [Å]: 1.39225 |
| Incident Beam Monochromator: No | K-A2/K-A1 Ratio: 0.50000 |
| Measurement Temperature [° C.]: 25.00 | Scan Type: Continuous |
| Generator Settings: 40 mA, 40 kV | Spinning: No |
| Dist. Focus-Diverg. Slit [mm]: 91.00 | |

Polarized Light Microscopy (PLM)

The presence of crystallinity (birefringence) was determined using an Olympus BX50 polarizing microscope, equipped with a Motic camera and image capture software (Motic Images Plus 2.0). Unless otherwise stated, all images were recorded using the 20x objective.

Thermogravimetric Analysis (TGA)

Approximately 5 mg of material was weighed into an open aluminum pan and loaded into a simultaneous thermogravimetric/differential thermal analyzer (TG/DTA) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 300 cm$^3$/min.

Differential Scanning Calorimetry (DSC)

Approximately 5 mg of material was weighed into an aluminum DSC pan and sealed nonhermetically with a pierced aluminum lid. The sample pan was then loaded into a Seiko DSC6200 (equipped with a cooler) cooled and held at 25° C. Once a stable heat-flow response was obtained, the sample and reference were heated to a maximum of 280° C. at a scan rate of 10° C./min and the resulting heat flow response monitored.

$^1$H Nuclear Magnetic Resonance ($^1$H NMR)

$^1$H-NMR experiments were performed on a Bruker PRO500 (frequency: 500 MHz). Experiments were performed in deuterated chloroform and each sample was prepared to ca. 10 mM concentration.

Gravimetric Vapor Sorption (GVS)

Approximately 10-20 mg of sample was placed into a mesh vapor sorption balance pan and loaded into an IGAsorp Moisture Sorption Analyzer balance by Hiden Analytical.

The sample was subjected to a ramping profile from 40% to 90% relative humidity (RH) at 10% increments, maintaining the sample at each step until a stable weight had been achieved (98% step completion). After completion of the sorption cycle, the sample was dried using the same procedure to 0% RH, and finally taken back to the starting point of 40% RH. The weight change during the sorption/desorption cycles was plotted, allowing for the hygroscopic nature of the sample to be determined.

High Performance Liquid Chromatography-Ultraviolet Detection (HPLC-UV)

Instrument: HPLC—Agilent 1100 with UV detector

Column: Waters X-Terra MSC18 (ISOx4.6x5 μm

Column Temperature: 30° C.

Autosampler Temperature: Ambient

UV wavelength: 220 nm

Injection Volume: 5 μm

Flow Rate: 1 mL/min
Mobile Phase A: 0.10% TFA in H$_2$O
Mobile Phase B: 0.1% TFA in MeCN
Gradient program:

| Time (minutes) | Solvent B [%] |
| --- | --- |
| 0 | 5 |
| 3 | 5 |
| 29 | 50 |
| 29.01 | 95 |
| 30 | 95 |
| 30.01 | 5 |
| 39 | 5 |

Example 3: Initial Characterization

Compound (I) prepared by the method described in Example 1 was characterized by PXRD, PLM, TG/DTA and DSC.

Example 4: Rapid Solvent Solubility Screen

Thirteen solvents were chosen for a rapid solvent solubility screen (See, Table 1). 10 mg of multiphasic Compound (I) prepared according to Example 1 was placed in each of 13 vials and 5 volume aliquots of the appropriate solvent systems were added to each vial.

Between each addition, the mixture was checked for dissolution and if no dissolution was apparent, the mixture was heated to 40° C. and checked again. This procedure was continued until dissolution was observed or until 100 volumes of solvent had been added.

TABLE 1

Solvents used in the rapid solvent solubility screen

| | Solvent | ICH Class |
| --- | --- | --- |
| 1 | Acetone | 3 |
| 2 | Acetonitrile | 2 |
| 3 | t-Butylmethyl Ether | 3 |
| 4 | Dichloromethane | 2 |
| 5 | Dimethylformamide | 2 |
| 6 | Ethanol | 3 |
| 7 | Ethyl Acetate | 3 |
| 8 | Heptane | 3 |
| 9 | Methanol | 2 |
| 10 | Propan-2-ol | 3 |
| 11 | Tetrahydrofuran | 2 |
| 12 | Toluene | 2 |
| 13 | Water | N/A |

Example 5: Primary Crystal Form Screen

The thirteen solvents investigated for the solubility screen were used for the primary crystal form screen. A saturated solution of Compound (I) prepared according to Example 1 was created by adding a volume of each solvent to 15 mg of the material.

These solutions were then split into four different vials for (1) cooling; (2) crash cooling; (3) evaporation; an (4) anti-solvent addition experiments. The resulting solids were analyzed by PXRD in the first instance.

Temperature Cycling

Based on the results from the solubility screen an appropriate volume of solvent was added to 15 mg of multiphasic Compound (I) prepared according to Example 1. The resulting slurries were temperature cycled between 5° C. and 25° C. on a hotplate for a period of 72 hours.

Post temperature cycling, solid material was separated from the solution and transferred onto an PXRD plate for analysis.

Cooling (4° C.)

A subsample was taken from each saturated solution vial from the primary crystal form screen and was cooled through storage in the fridge at 4° C.

Crash Cooling (−20° C.)

A subsample was taken from each saturated solution vial from the primary crystal form screen and was cooled through storage in a freezer at −20° C.

Evaporation

A subsample taken from each saturated solution vial from the primary crystal form screen was allowed to crystallize through evaporation in an uncapped vial at room temperature conditions.

Anti-Solvent Additions

A subsample was taken from each saturated solution vial from the primary crystal form screen and an anti-solvent (heptane or tBME) was added in 50 mL aliquots until precipitation halted or until the vials contained a maximum volume of 2.4 mL.

Example 6: Secondary Crystal Form Screen

Positive 'hits' from the primary crystal form screen were scaled up to test reproducibility. Full characterization of the solid materials was carried out on the dried solid through the use of PXRD, PLM, TG/DTA and DSC.

Example 7: 7 Day Stability Test at 40° C. and 75% Relative Humidity 10 mg of Forms 1, 2, 3, 4 and 5 were weighed out into separate vials.

Each vial was placed in an oven at 40° C. and 75% Relative Humidity for 7 days. After completion, PXRD analysis was performed on each of these samples.

Example 8: Competitive Slurrying of Form 1 and Form 5

Saturated solutions of Compound (I) in multiphasic form were created in two solutions each dichloromethane, heptane and methanol.

10 mg of Form 1 and Form 5 were added to each vial. Each vial was stirred at ambient conditions for a period of 24 hours, while the other heptane and methanol vials were stirred at 60° C. for 24 hours.

The remaining dichloromethane vial was stirred at 35° C. for 24 hours. The resulting material was analyzed by PXRD, before being dried with a vacuum pump overnight to dry before DSC analysis of samples.

Example 9: Large Scale-Up of Form 1

To create a slurry, Acetone (3.5 mL) was added to a vial containing 1.236 g of multiphasic Compound (I) prepared according to Example 1. The resulting solution was then temperature cycled for a period of 24 hours.

Crystallinity Form was then confirmed using PXRD, TGA, DSC and PLM.

Example 10: Further Stability Studies—Form 1

10 mg of Form 1 was weighed out into each of 12 vials. Four (4) vials were placed in each storage condition of: (1)

40° C. with an open cap; (2) 75% RH with an open cap; (3) 50° C. with a closed cap; and (4) room temperature with a closed cap.

Two (2) vials were extracted at each time point of 2 and 4 weeks and PXRD, NMR and HPLC analysis was performed.

Example 11: Rapid Solvent Solubility Screen

Compound (I) was found to be largely insoluble (<10 mg/mL) in the majority of solvents assessed. Only two solvents exhibited solubility>10 mg/mL wherein Compound (I) was very highly soluble in dichloromethane (200 mg/mL) and sparingly soluble in methanol (12.5 mg/mL).

PXRD analysis was carried out on the un-dissolved material of the solubility screen. PXRD of un-dissolved material from the solubility screen all show the same form with clear similarities to the multiphasic form (starting material). The solvents appear to 'clear' a peak at the 2θ=12 and 28.5°.

TABLE 2

Solubility of Compound (I) Determined from the Solvent Solubility Screen

| | Solvent | Solubility |
|---|---|---|
| 1 | Acetone | <10 mg/mL |
| 2 | Acetonitrile | <10 mg/mL |
| 3 | t-Butylmethyl Ether | <10 mg/mL |
| 4 | Dichloromethane | 200 mg/mL |
| 5 | Dimethylformamide | <10 mg/mL |
| 6 | Ethanol | <10 mg/mL |
| 7 | Ethyl Acetate | <10 mg/mL |
| 8 | Heptane | <10 mg/mL |
| 9 | Methanol | 12.5 mg/mL |
| 10 | Propan-2-ol | <10 mg/mL |
| 11 | Tetrahydrofuran | <10 mg/mL |
| 12 | Toluene | <10 mg/mL |
| 13 | Water | <10 mg/mL |

Figure 7:
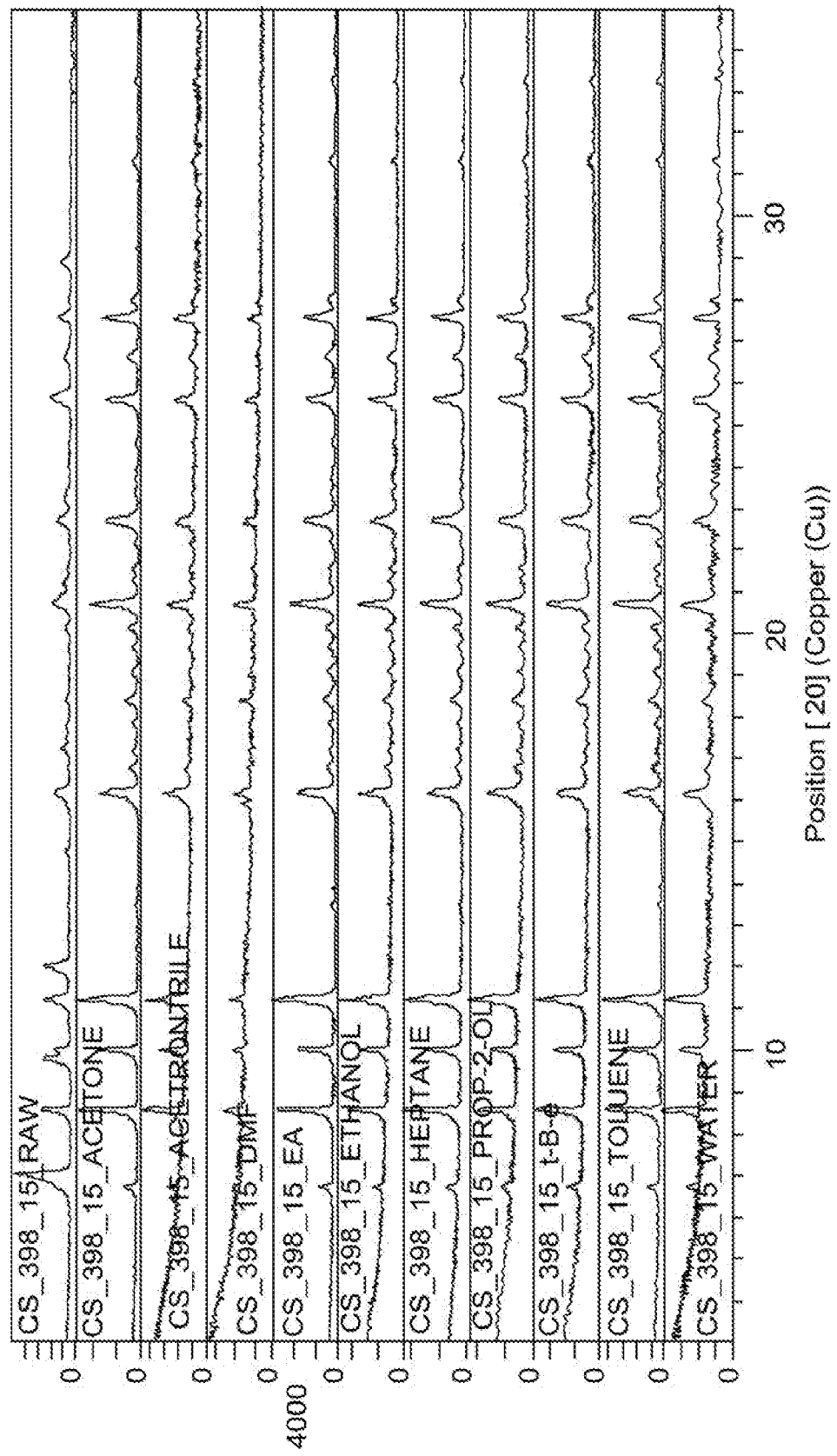
FIG. 7 depicts the powder X-ray diffraction pattern (PXRD) of un-dissolved material from the solubility screen described in Example 4.

FIG. 7 provides the results from the PXRD analysis of undissolved material from the solubility screen.

Example 12: Primary Crystal Form Screen

Five crystalline forms of Compound (I) were discovered during the primary screen (Table 3).

Figure 8:
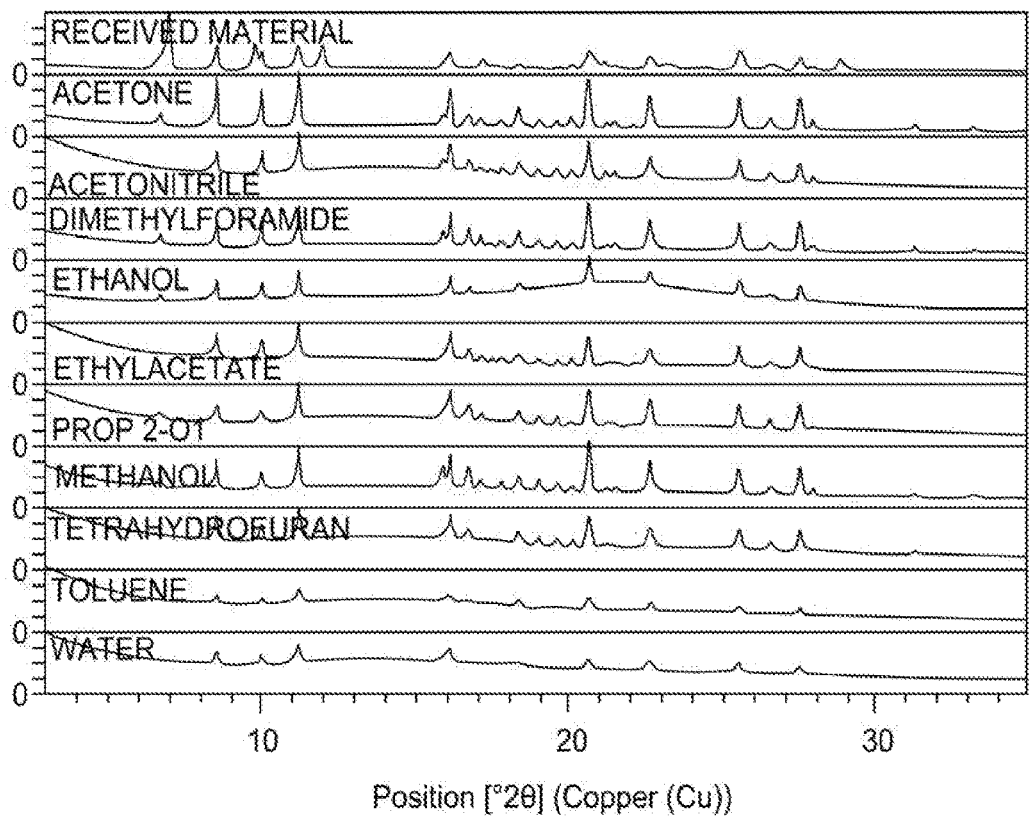
FIG. 8 depicts the powder X-ray diffraction pattern (PXRD) of solvent slurries of the multiphasic form of N-methyl-2-(4-methyl-1,4-diazepan-1-yl)benzo[4,5]imidazo[1,2-a][1,8]naphthyridine-6-carbaxomide (Compound (I)) that produced Form 1.

Form 1 was found to be the most commonly identified form and was isolated from slurries of acetone; acetonitrile; tBME; dimethylformamide; ethanol; ethyl acetate; heptane; methanol; propan-2-ol; tetrahydrofuran; and toluene (See, FIG. 8).

Form 2 was isolated from a slurry of 1,4-dioxane and Form 3 was isolated from a slurry of dichloromethane slurry (See, FIG. 9).

Form 4 was isolated from a slurry of dichloromethane evaporative (See, FIG. 10).

Form 5 was isolated from a slurry of dichloromethane anti-solvent (See, FIG. 11).

TABLE 3

Primary Crystal Form Screen Results Matrix

| Solvent | Temperature Cycling | Evaporation | Anti-solvent | Crash Cool |
|---|---|---|---|---|
| 1,4-Dioxane | Form 2 | WD | WD | WD |
| Acetone | Form 1 | WD | WD | WD |
| Acetonitrile | Form 1 | WD | WD | WD |
| t-Butylmethyl Ether | Form 1 | WD | WD | WD |
| Dichloromethane | Form 3 | Form 4 | Form 5 | WD |
| Dimethylformamide | Form 1 | WD | WD | WD |
| Ethanol | Form 1 | WD | WD | WD |
| Ethyl Acetate | Form 1 | WD | WD | WD |
| Heptane | Form 1 | WD | WD | WD |
| Methanol | Form 1 | WD | WD | WD |
| Propan-2-ol | Form 1 | WD | WD | WD |
| Tetrahydrofuran | Form 1 | WD | WD | WD |
| Toluene | Form 1 | WD | WD | WD |

No/Insufficient Solid
WD Weak Data

Due to the insolubility of Compound (I) in the vast majority of solvent systems, only dichloromethane produced sufficient material to analyze in the evaporation, anti-solvent addition and crash cooling experiments.

Example 13: Competitive Slurrying of Form 1 and Form 5

Figure 53:
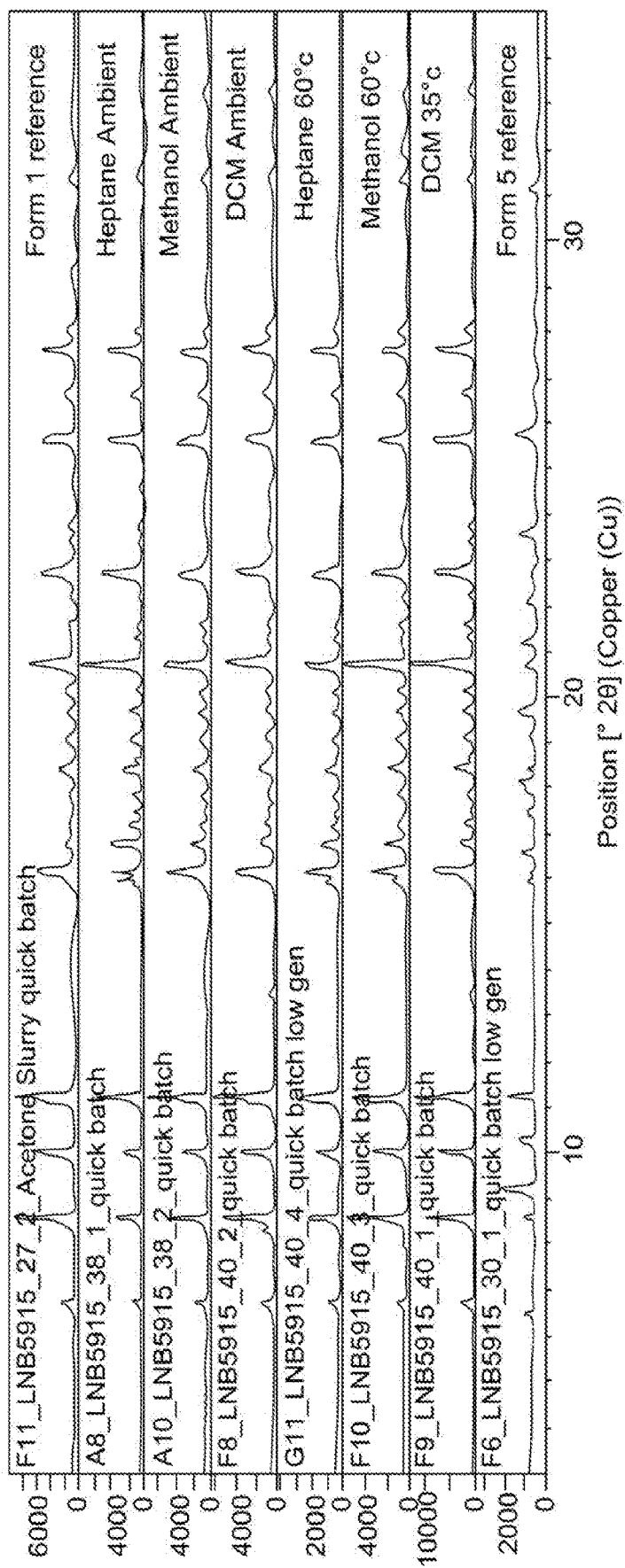
FIG. 53 depicts the powder X-ray diffraction pattern (PXRD) from the competitive slurry of Form 1 and Form 5.

PXRD analysis of the damp slurry residue indicated that all of the experiments promoted a transition from Form 5 towards Form 1 (See, FIG. 53).

Figure 22:
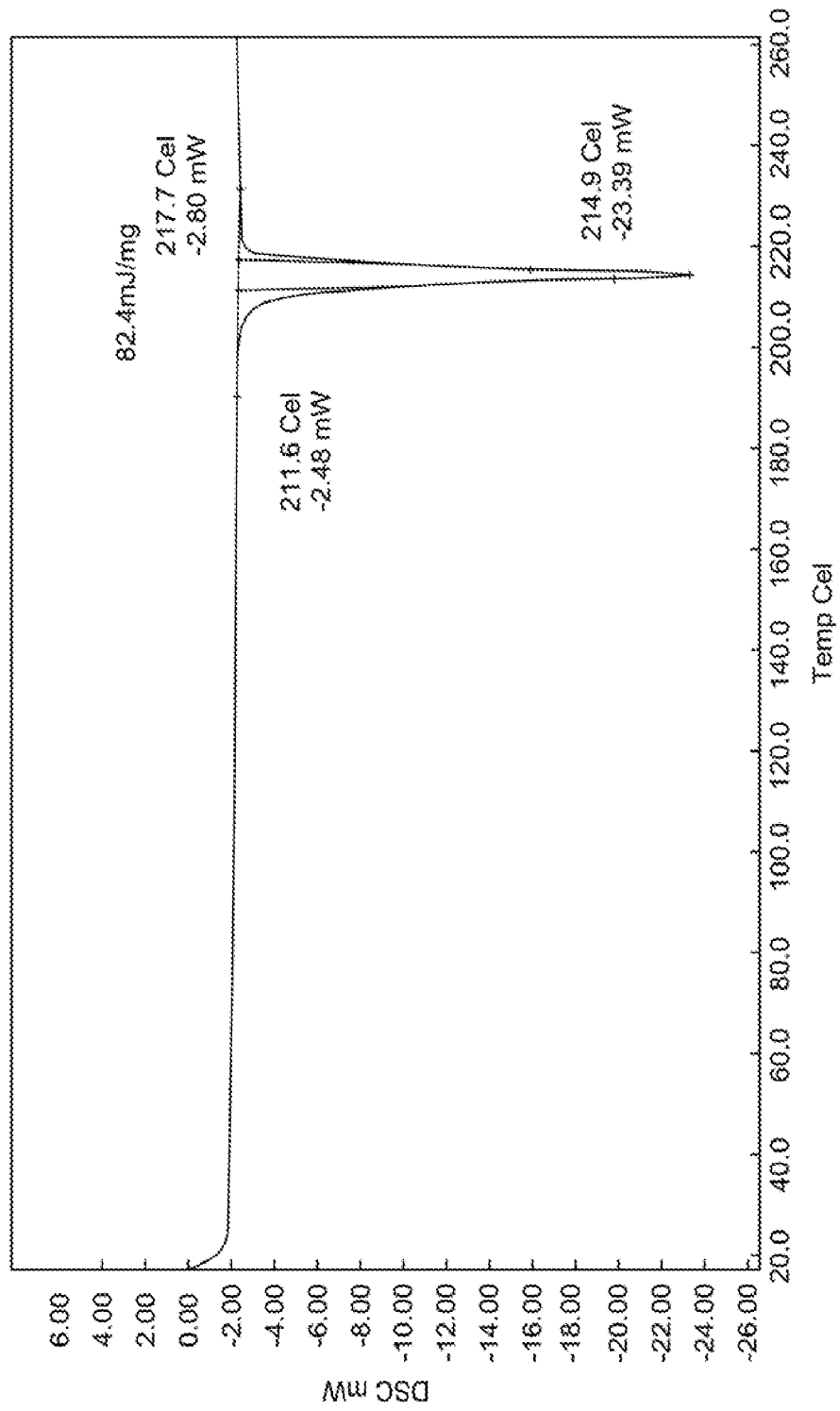
FIG. 22 depicts the Differential Scanning Calorimetry (DSC) thermogram ($1^{st}$ heating cycle) of Form 1.

Table 4 summarizes the DSC traces of competitive slurry material (see, FIGS. 54-59) in comparison to the DSC traces of Form 1 and Form 5 identified from the secondary screen (see, FIGS. 22 and 48, respectively).

FIG. 53 shows PXRDs of competitive slurrying of Form 1 and Form 5.

Figure 54:
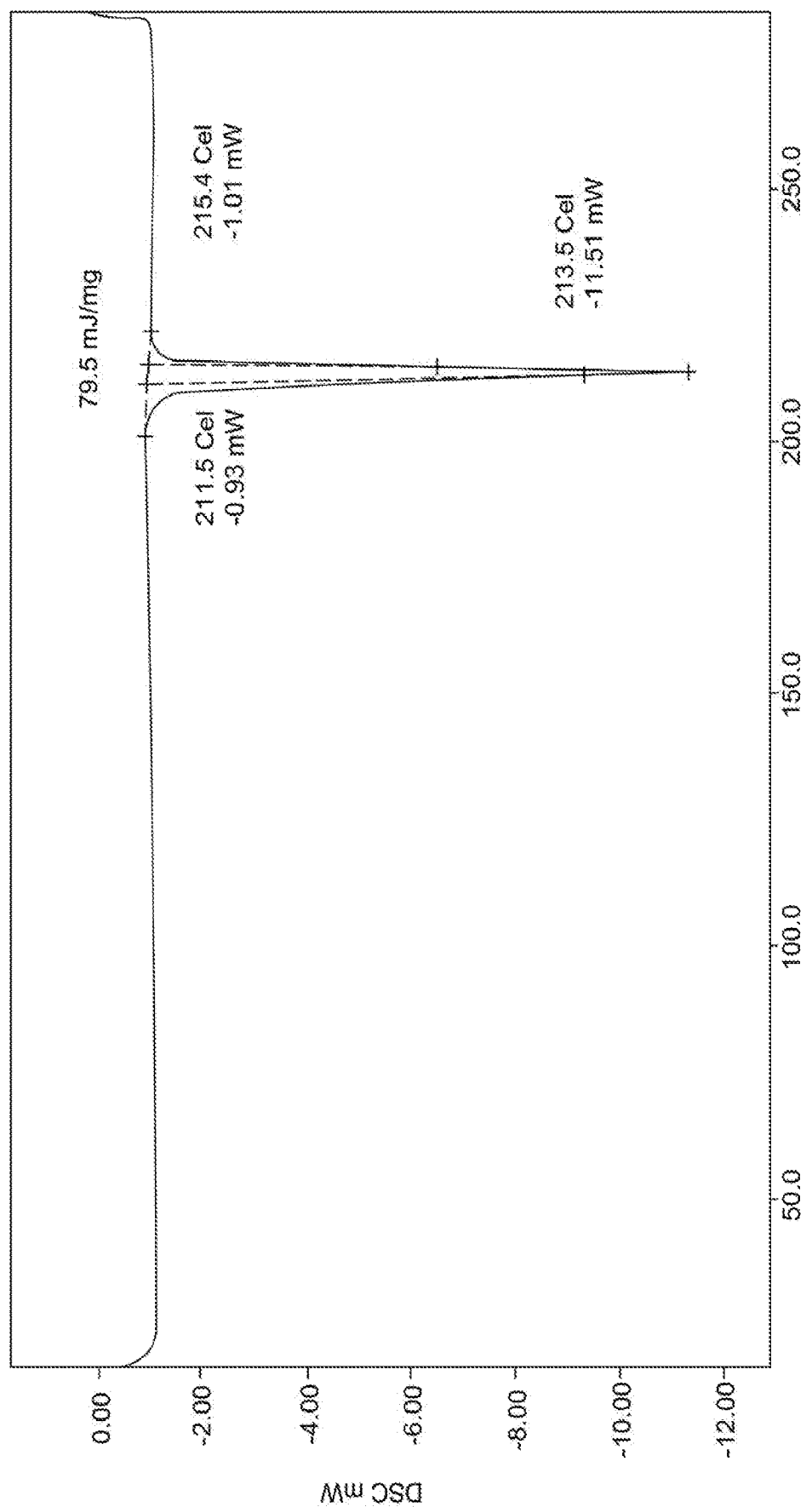
FIG. 54 depicts the Differential Scanning Calorimetry (DSC) thermogram when the competitive slurry material was heptane at room temperature.

FIG. 54 shows DCS analysis of material from heptane ambient competitive slurry.

Figure 55:
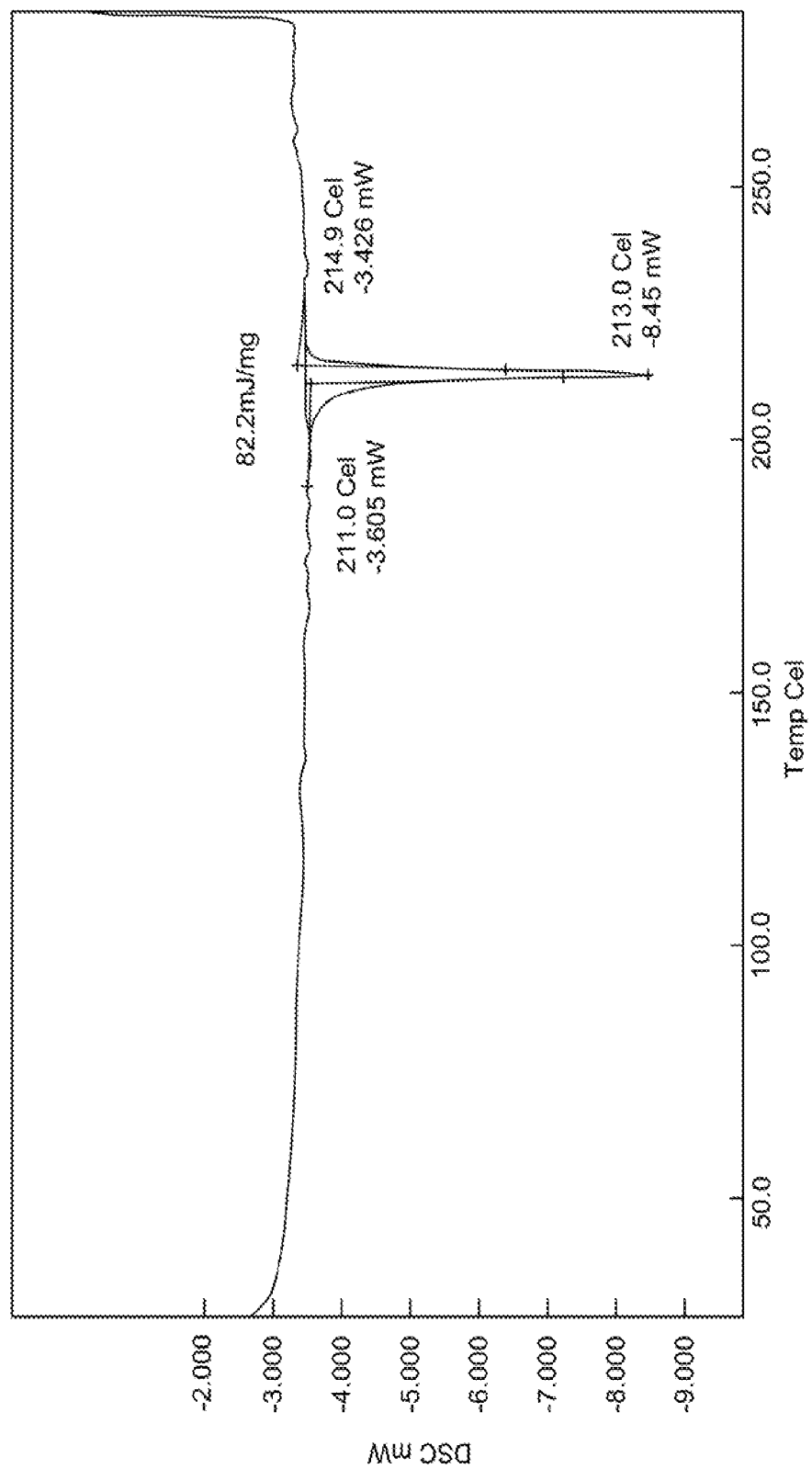
FIG. 55 depicts the Differential Scanning Calorimetry (DSC) thermogram when the competitive slurry material was heptane at 60° C.

FIG. 55 shows DSC analysis of material from heptane 60° C. competitive slurry.

Figure 56:
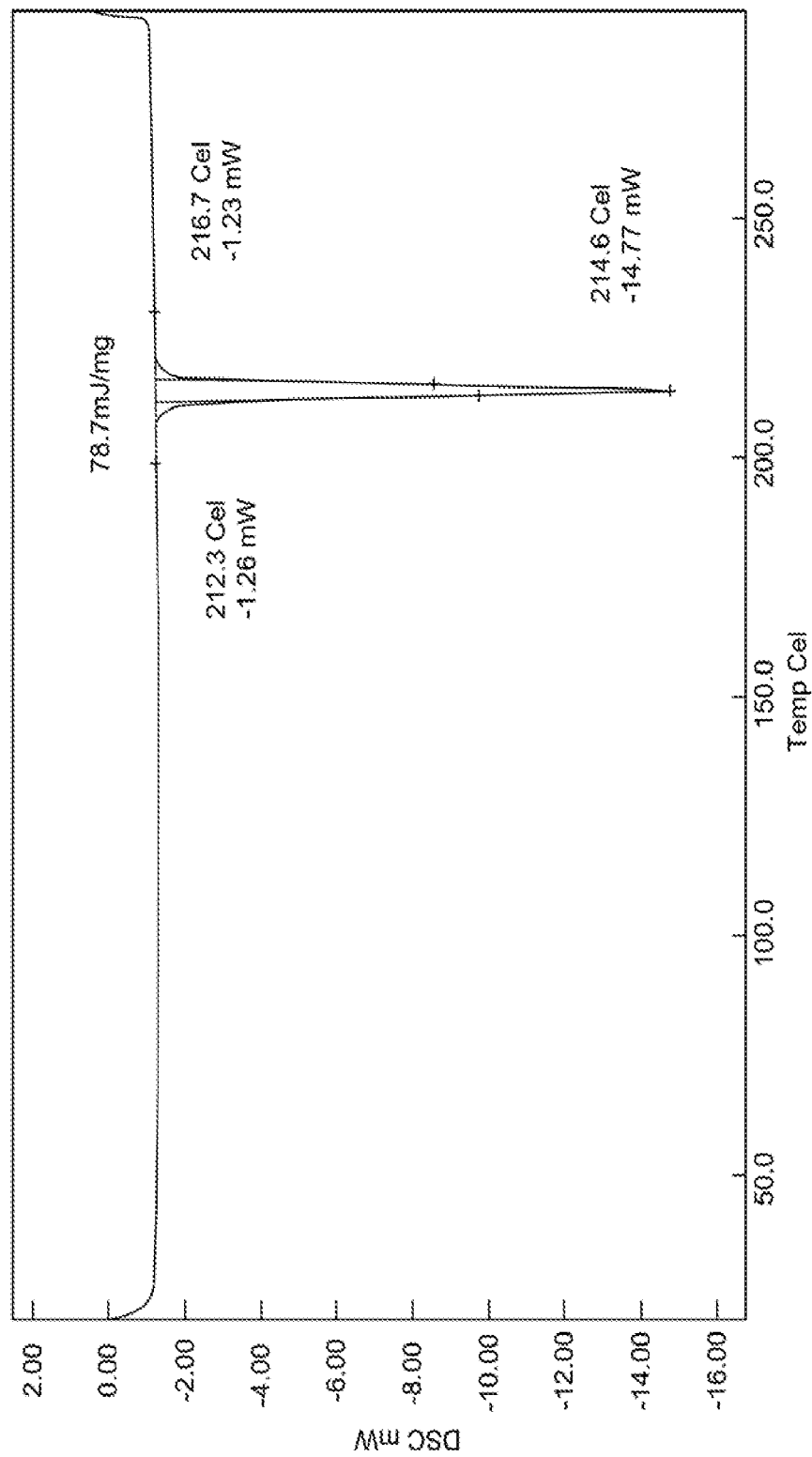
FIG. 56 depicts the Differential Scanning Calorimetry (DSC) thermogram when the competitive slurry material was methanol at room temperature.

FIG. 56 shows DSC analysis of material from methanol ambient competitive slurry.

Figure 57:
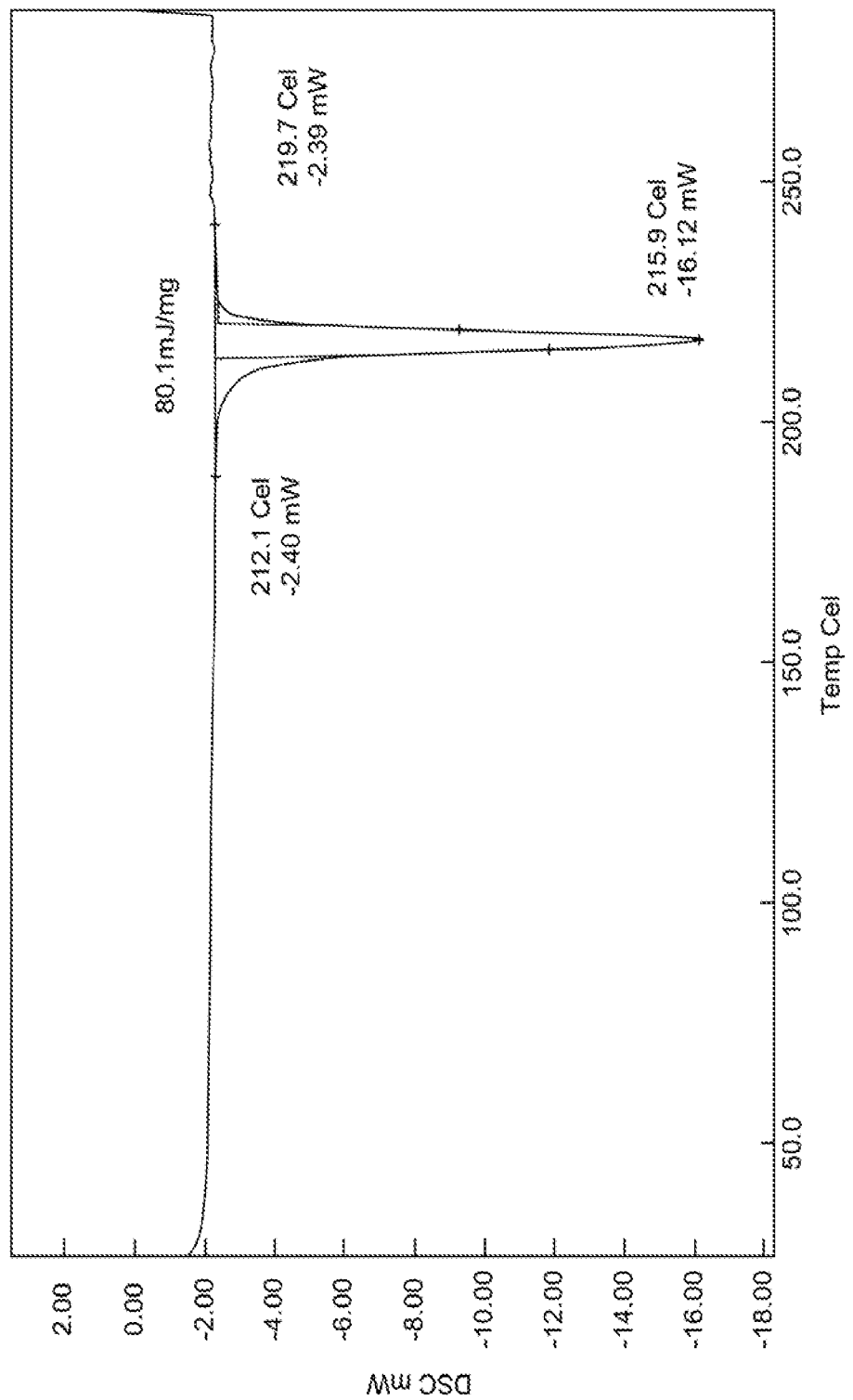
FIG. 57 depicts the Differential Scanning Calorimetry (DSC) thermogram when the competitive slurry material was methanol at 60° C.

FIG. 57 shows DSC analysis of material from methanol 60° C. competitive slurry.

Figure 58:
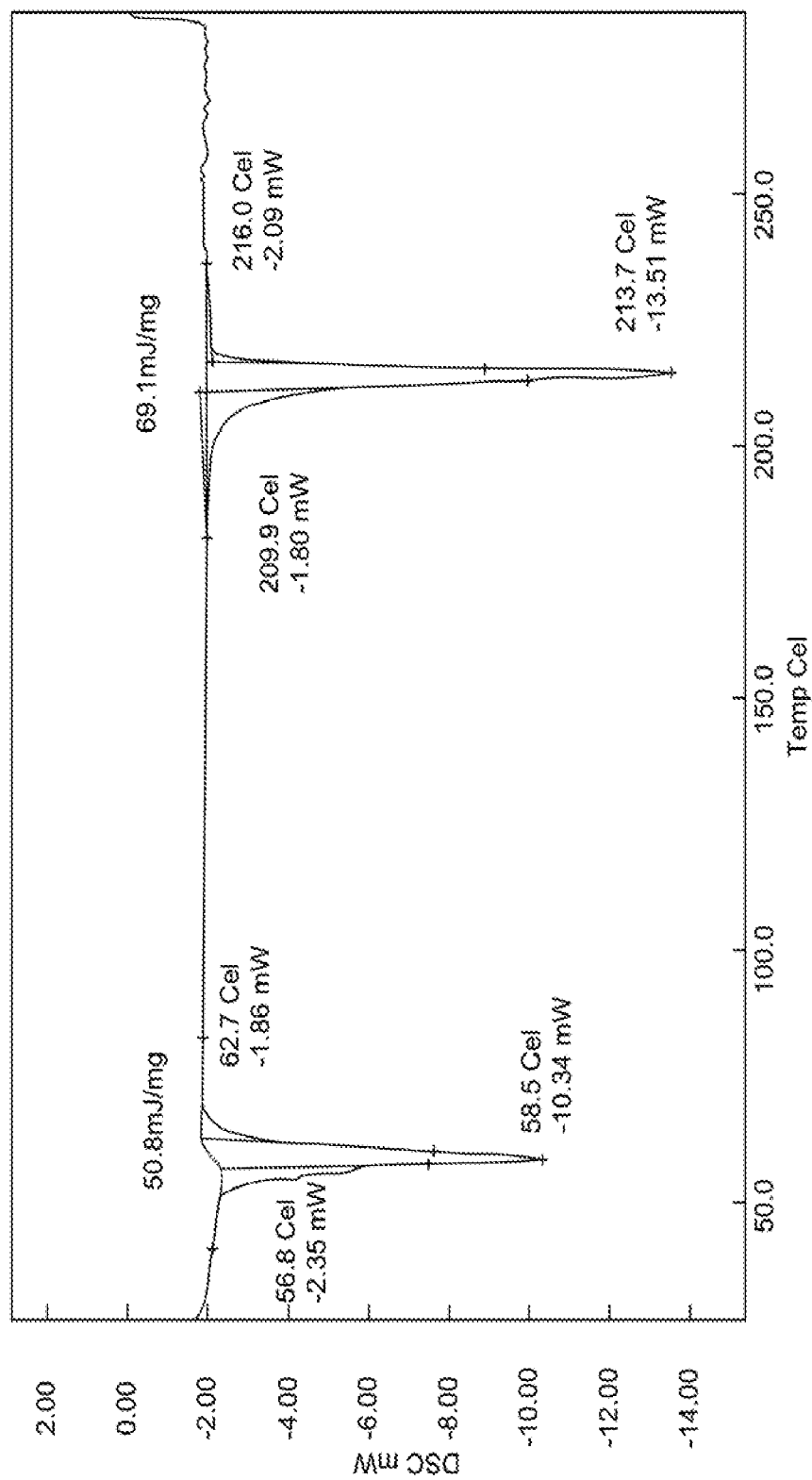
FIG. 58 depicts the Differential Scanning Calorimetry (DSC) thermogram when the competitive slurry material was dichloromethane (DCM) at room temperature.
Figure 59:
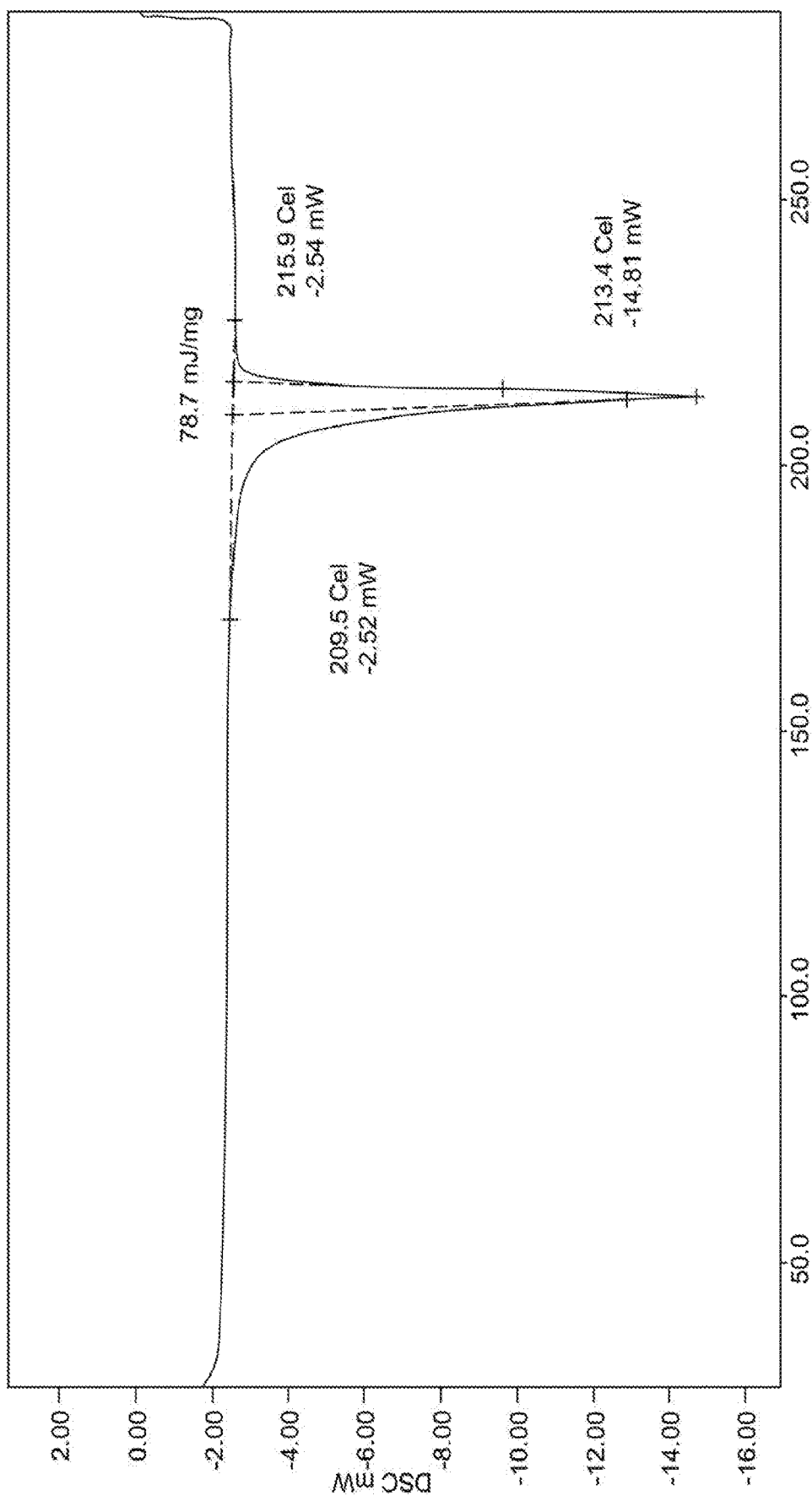
FIG. 59 depicts the Differential Scanning Calorimetry (DSC) thermogram when the competitive slurry material was dichloromethane (DCM) at 35° C.

FIG. 58 shows DSC analysis of material from DCM ambient slurry. It can be seen that the dichloromethane ambient DSC trace displays an initial endothermic event.

Figure 60:
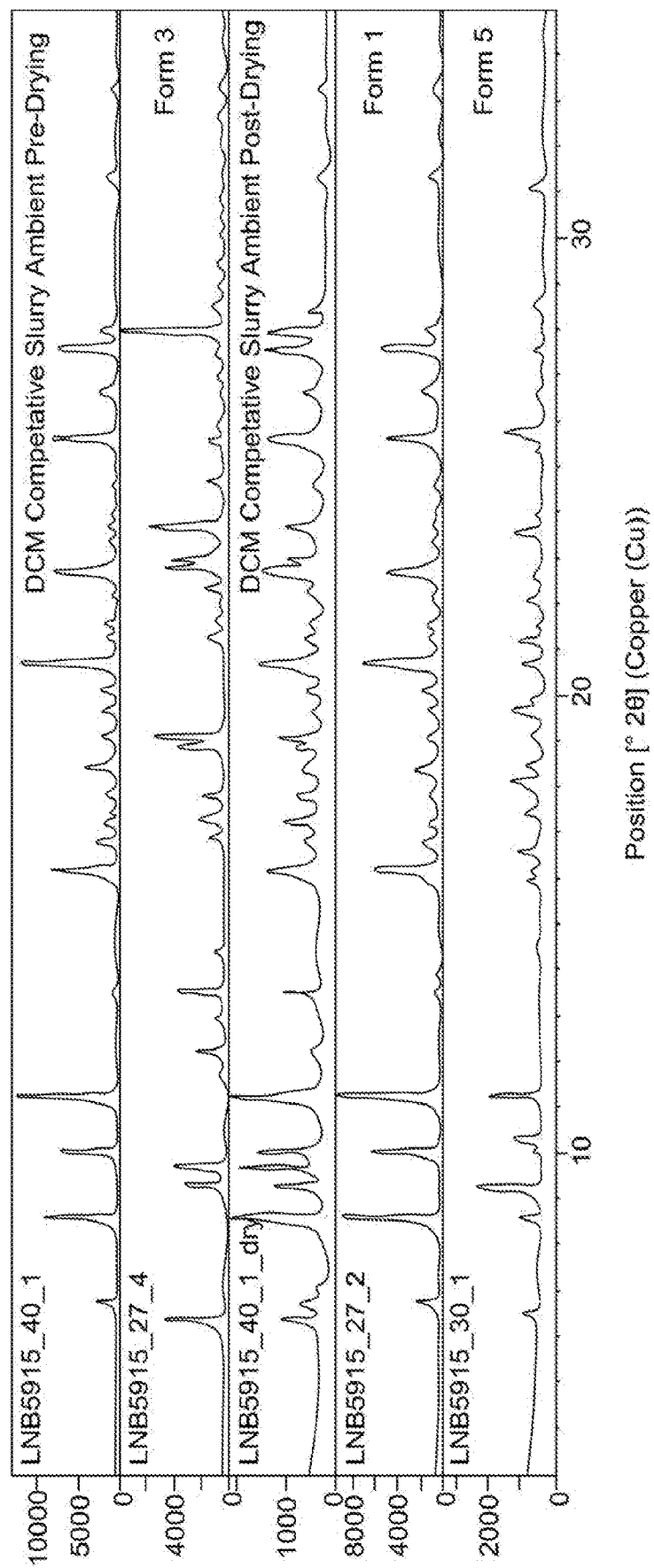
FIG. 60 depicts the powder X-ray diffraction pattern (PXRD) of the dichloromethane competitive slurry at room temperature before drying (top); the dichloromethane competitive slurry at room temperature after drying (3$^{rd}$ from top); and the crystalline Forms 1, 3 and 5 (2$^{nd}$ from bottom, 2$^{nd}$ from top, and bottom, respectively) as references.

Subsequent PXRD analysis of the dry material showed it had transitioned into a mixture of Form 1 and Form 3 during the drying process (See, FIG. 60).

TABLE 4

Summary of DSC Traces

| | Sample | Onset of melt | Peak of melt | Enthalpy of melt (mJ/mg) |
|---|---|---|---|---|
| 1 | Form 1 | 211.6 | 214.9 | 83 |
| 2 | Form 5 | 211.4 | 213.5 | 82 |
| 1 | Heptane Ambient | 211.5 | 213.5 | 80 |
| 2 | Heptane 60° C. | 211 | 213 | 82 |
| 3 | Methanol Ambient | 212.3 | 214.6 | 79 |
| 4 | Methanol 60° C. | 212.1 | 215.9 | 80 |
| 5 | Dichloromethane Ambient | 209.9 | 213.7 | 69 |
| 6 | Dichloromethane 35° C. | 209.5 | 213.4 | 79 |

The embodiments illustrated and discussed in this specification are intended only to teach those skilled in the art how to make and use the invention. In describing embodi-

What is claimed is:

1. A crystalline form of Compound (I):

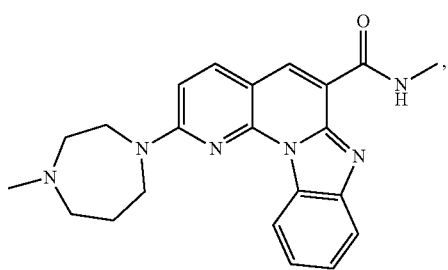

(I)

N-methyl-2-(4-methyl-1,4-diazepan-1-yl)benzo[4,5]imidazo[1,2-a][1,8]naphthyridine-6-carboxamide characterized by having a powder X-ray diffraction (PXRD) pattern peaks of 2-theta, at about 10.0° and 20.7°, the crystalline form being the crystalline Form 1.

2. The crystalline form of claim 1, wherein the crystalline Form 1 is characterized by having a powder X-ray diffraction pattern peaks of 2-theta, at about 6.7°, 8.6°, 10.0°, 11.2°, 16.2°, 20.7°, 22.7°, 25.6° and 27.6° (+0.2° 2θ).

Figure 81:
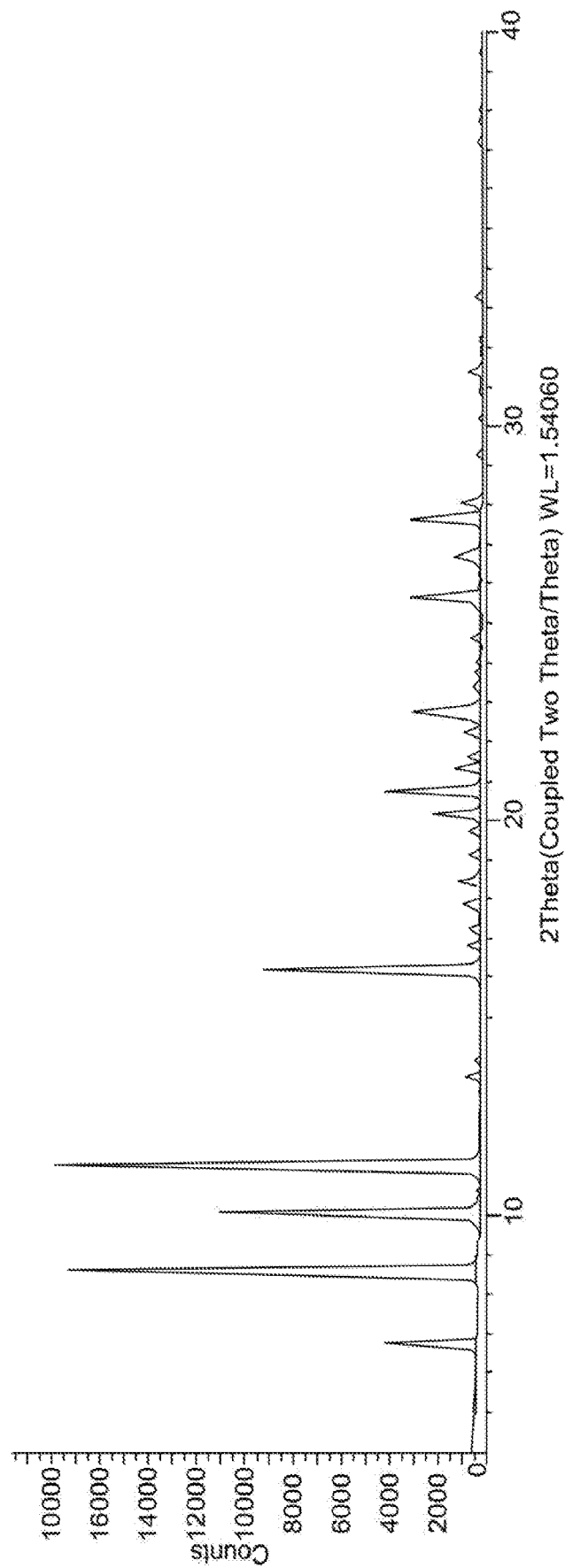
FIG. 81 depicts the powder X-ray diffraction pattern (PXRD) of Form 1.

3. The crystalline form of claim 1, wherein the crystalline Form 1 is characterized by having the powder X-ray diffraction pattern substantially as shown in FIG. 81.

4. The crystalline form of claim 1, wherein the crystalline Form 1 is further characterized as having an endotherm peak at about 212-216° C. as shown by DSC.

5. The crystalline form of claim 1, wherein the crystalline Form 1 is further characterized as having an endotherm onset at about 209-212° C. as shown by DSC.

6. A pharmaceutical composition comprising the crystalline form of claim 1, and a pharmaceutically acceptable carrier.

7. A method of treating cancer in a subject in need thereof, comprising administering a therapeutically effective amount of the composition of claim 6.

8. The method of claim 7, wherein the cancer is of the breast, lung, colorectum, liver, pancreas, lymph node, colon, prostate, brain, head and neck, skin, liver, kidney, blood or heart.